(12) United States Patent
McMahan et al.

(10) Patent No.: US 8,354,507 B2
(45) Date of Patent: Jan. 15, 2013

(54) HLA-DR SPECIFIC ANTIBODIES, COMPOSITIONS AND METHODS

(75) Inventors: Cathy McMahan, Seattle, WA (US); Lara Porter Stepan, Seattle, WA (US); Reiner Laus, Bellevue, WA (US); Damir Vidovic, Bellevue, WA (US)

(73) Assignee: Dendreon Corporation, Seattle, WA (US)

( * ) Notice: Subject to any disclaimer, the term of this patent is extended or adjusted under 35 U.S.C. 154(b) by 683 days.

(21) Appl. No.: 11/013,537

(22) Filed: Dec. 15, 2004

(65) Prior Publication Data
US 2005/0208048 A1  Sep. 22, 2005

Related U.S. Application Data

(60) Provisional application No. 60/608,944, filed on Dec. 15, 2003.

(51) Int. Cl.
*C07K 16/00* (2006.01)
*C07K 16/18* (2006.01)
*C07K 16/28* (2006.01)
*C07K 17/00* (2006.01)

(52) U.S. Cl. ............................ 530/388.1; 530/388.22

(58) Field of Classification Search .................. None
See application file for complete search history.

(56) References Cited

U.S. PATENT DOCUMENTS

| | | | |
|---|---|---|---|
| 6,416,958 B2 * | 7/2002 | Vidovic et al. | ............ 435/7.1 |
| 7,262,278 B2 | 8/2007 | Tawara et al. | |
| 2008/0200523 A1 * | 8/2008 | Murthi et al. | ............ 514/352 |

FOREIGN PATENT DOCUMENTS

| | | |
|---|---|---|
| EP | 0255694 A1 | 2/1988 |
| EP | 1 156 060 A1 | 11/2001 |
| EP | 1 369 431 A1 | 12/2003 |
| JP | 63-36796 A | 2/1988 |
| JP | 8-511421 T | 12/1996 |
| JP | 2000-517289 T | 12/2000 |
| WO | WO/94/29451 A1 | 12/1994 |
| WO | WO 97/26912 A2 | 7/1997 |
| WO | WO/0012560 A1 | 3/2000 |
| WO | WO 03/033538 A1 | 4/2003 |

OTHER PUBLICATIONS

De Pascalis et al (J. Immunol. 2002, 169: 3076-3084).*
Casset et al (2003, BBRC 307: 198-205).*
Rudikoff et al (PNAS USA 1982, 79: 1979).*
Worker, C. (IDrugs 2002, 5(2): 121-123).*
Joliffe (International Rev. Immunol. 1993, 10 (2-3): 241-250).*
Truman, Jean-Phillip, et al.; "HLA Class II—Mediate Death is Induced Via Fas/Fas Ligand Interactions in Human Splenic B Lymphocytes," *Blood*, vol. 89 No. 6, pp. 1996-2007 (Mar. 15, 1997).
Babbit, Bruce P., et al.; "Binding of Immunogenic Peptides to Ia Histocompatibility Molecules," *Nature*, vol. 317, No. 26, pp. 359-361 (Sep. 1985).
Newal, M. Karen, et al.; "Ligation of Major Histocompatibility Complex Class II Molecules Mediates Apoptotic Cell Death in Resting B. Lymphocytes," *Proc. Natl. Acad. Sci.*, vol. 90, pp. 10459-10463 (Nov. 1993).
Truman, Jean-Phillip, et al.; "Lymphocyte Programmed Cell Death is Mediated Via HLA Class II DR," *International Immunology*, vol. 6, No. 6, pp. 887-896 (1994).
Vidovic, Damir, et al.; "Down-regulation of Class II Major Histocompatibility Complex Molecules on Antigen-presenting Cells by Antibody Fragments," *Eur. J. Immunol.*, vol. 25, pp. 3349-3355 (1995).
Kozbor, Danuta, et al.; "The Production of Monoclonal Antibodies from Human Lymphocytes," *Immunology Today*, vol. 4, No. 3, pp. 72-79 (1998).
Mollick, Joseph, et al.; "Staphylococcal Exotoxin Activation of T Cells—Role of exotoxin-MHC Class II Binding Affinity and Class II Isotype," *The Journal of Immunology*, vol. 146, No. 2, pp. 463-468 (Jan. 15, 1991).
Lampson, Lois A., et al.; "Two Populations of Ia-Like Molecules on a Human B Cell Line," *The Journal of Immunology*, vol. 125, No. 1, pp. 293-299 (Jul. 1980).
Fu, Xin-Ting, et al.; "HLA-DRα Chain Residues Located on the Outer Loops are Involved in Nonpolymorphic and Polymorphic Antibody-Binding Epitopes," *Human Immunology*, vol. 39, pp. 253-260 (1994).
Jones, Peter T., et al.; "Replacing the Complementarity-Determining Regions in a Human Antibody with Those from a Mouse," *Nature*, vol. 321, No. 29, pp. 522-525 (May 1986).
Riechmann, Lutz, et al.; "Reshaping Human Antibodies for Therapy," *Nature*, vol. 332, No. 24, pp. 323-327 (Mar. 1988).
Verhoeyen, Martine, et al.; "Reshaping Human Antibodies: Grafting an Antilysozyme Activity," *Science*, vol. 239, pp. 1534-1536 (Mar. 25, 1988).
Vidovic, D., et al.; "Selective Apoptosis of Neoplastic Cells by the HLA-DR-Specific Monoclonal Antibody," *Cancer Letters*, vol. 128, pp. 127-135 (1998).
Vidovic, Damir, et al.; ABSTRACT: "Specific Stimulation of MHC-Transgenic Mouse T-Cell Hybridomas with Xenogeneic APC," *Human Immunology*, vol. 64, Issue 2, pp. 238-244 (Feb. 2003).
Business Wire, "Dendreon Grants Kirin HLA-DR Antibody License to Regain Asian Rights to Provenge Immunotherapy," p. 5174 (Nov. 14, 2003). SCRIP, "Dendreon to Acquire Corvas," No. 2828, p. 11 (2003).
The International Search Report and Written Opinion for PCT/US2004/042312, search report dated Jun. 14, 2005, 7 pages (2005).
The Supplementary European Search Report for EP 04 81 4490, search report dated Jul. 23, 2008, 4 pages (2008).
Nagy et al., "Fully human, HLA-DR-specific monoclonal antibodies efficiently induce programmed death of malignant lymphoid cells", *Nature Medicine*, 8(8):801-807 (2002).

(Continued)

Primary Examiner — Gerald R Ewoldt
Assistant Examiner — Marianne DiBrino
(74) Attorney, Agent, or Firm — King & Spalding LLP; Peter Dehlinger

(57) ABSTRACT

HLA-DR-specific monoclonal antibodies are provided that are capable of inducing apoptosis in HLA-DR-expressing tumor cells. Certain exemplary HLA-DR-specific antibodies exhibit reduced levels of immunosuppressive activity. Antibodies of the present invention will find use in diagnostic methods as well as in compositions and methods for the treatment of cancers associated with HLA-DR expressing tumor cells.

7 Claims, 25 Drawing Sheets

OTHER PUBLICATIONS

Kostelny et al., "Humanization and characterization of the anti-HLA-DR antibody 1D10", *International Journal of Cancer*, 93(4):556-565 (2001).

Dendreon Corporation Form 10-K, Annual Report Pursuant to Section 13 or 25(d) of the Securities Exchange Act of 1934 for the Fiscal Year Ended Dec. 31, 2000, U.S.A., Securites and Exchange Commission Washington D.C. 20549, 2001, searched on Sep. 14, 2010, Commision File No. 000-30681, pp. 1-10, <http://markets.financialcontent.com/stocks/action/getedgarwindow?accesscode=103221001500150.

* cited by examiner

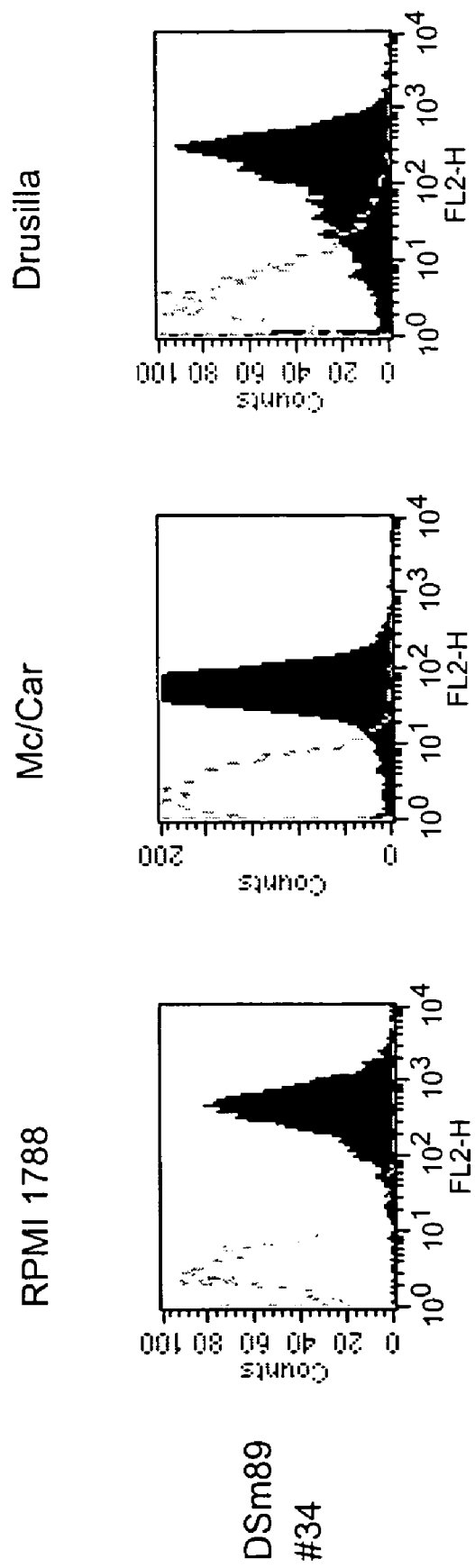

Fig. 7D
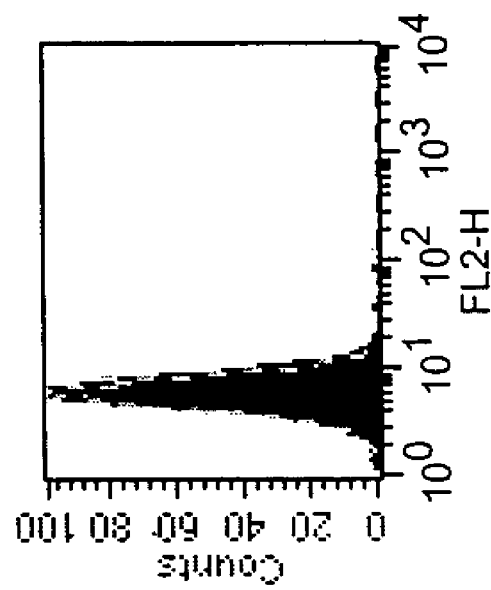
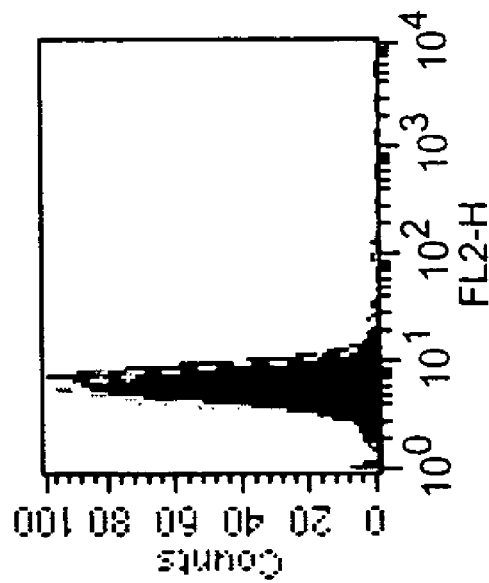

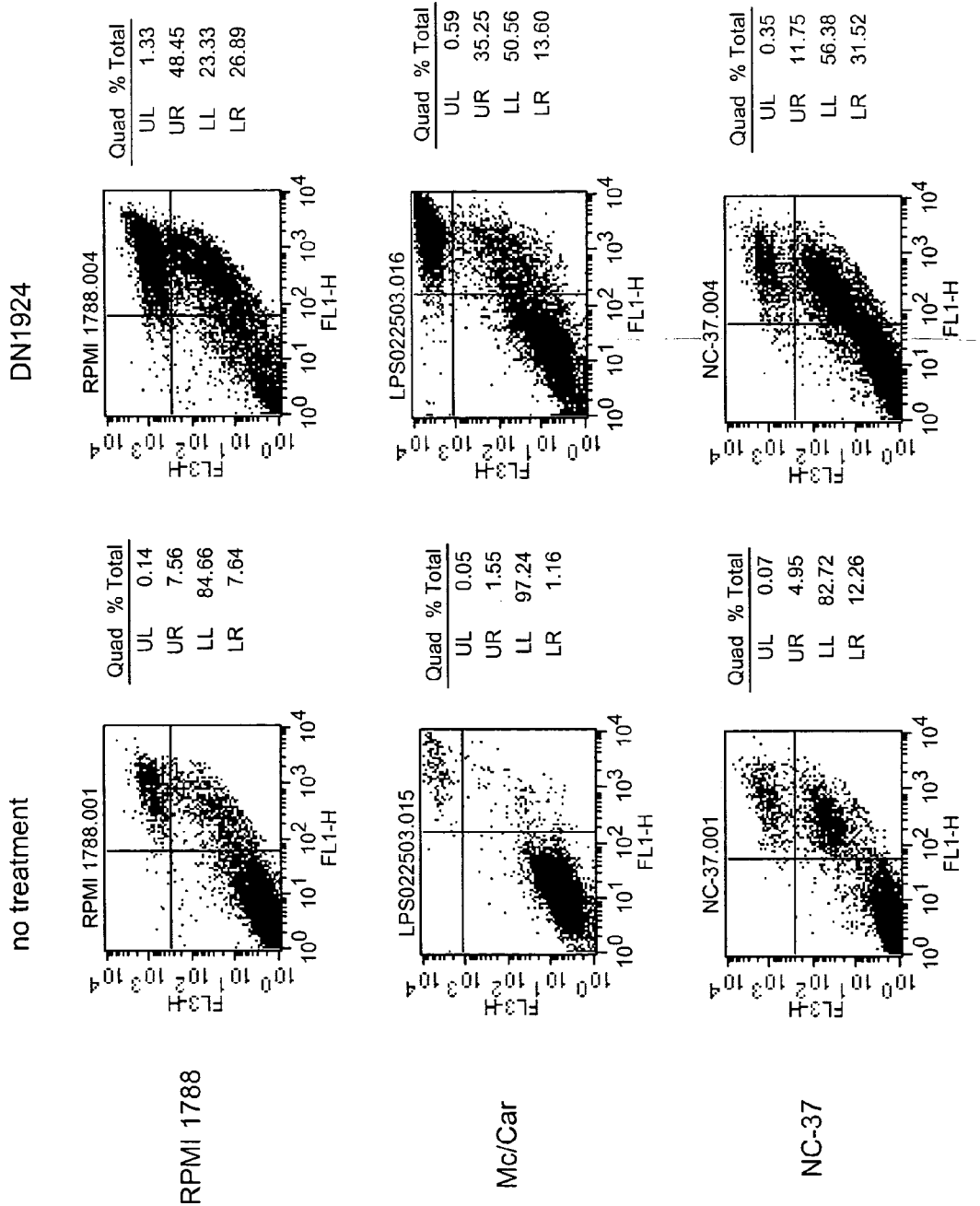

```
hIgK   -TVAAPSVFIFPPSDEQLKSGTASVVCLLNNFYPREAKVQWKVDNALQSG
hIgK   RTVAAPSVFIFPPSDEQLKSGTASVVCLLNNFYPREAKVQWKVDNALQSG
mIgK   RADAAPTVSIFPPSSEQLTSGGASVVCFLNNFYPKDINVKWKIDGSERQN

NSQESVTEQDSKDSTYSLSSTLTLSKADYEKHKVYACEVTHQGLSSPVTK
       NSQESVTEQDSKDSTYSLSSTLTLSKADYEKHKVYACEVTHQGLSSPVTK
       GVLNSWTDQDSKDSTYSMSSTLTLTKDEYERHNSYTCEATHKTSTSPIVK

SFNRGEC-
       SFNRGEC-
       SFNRNEC-
```

Fig. 11

```
hIgG2   ASTKGPSVFPLAPCSRSTSESTAALGCLVKDYFPEPVTVSWNSGALTSGV
hIgG1   -STKGPSVFPLAPSSKSTSGGTAALGCLVKDYFPEPVTVSWNSGALTSGV
hIgG4   ASFKGPSVFPLVPCSRSTSESTAALGCLVKDYFPEPVTVSWNSCALTSGV
mIgG1   -KTTPPSVYPLAPGSAAQTNSMVTLGCLVKGYFPEPVTVTWNSGSLSSGV
mIgG2a  -KTTAPSVYPLAPVCGDTTGSSVTLGCLVKGYFPEPVTLTWNSGSLSSGV
mIgG2b  -KTTPPSVYPLAPGCGDTTGSSVTLGCLVKGYFPESVTVTWNSGSLSSSV

HTFPAVLQSSGLYSLSSVVTVTSSNFGTQTYTCNVDHKPSNTKVDKTVER
        HTFPAVLQSSGLYSLSSVVTVPSSSLGTQTYICNVNHKPSNTKVDKKVEP
        HTFPAVLQSSGLYSLSSVVTVPSSSLGTKTYTCNVDHKPSNTKVDKRVES
        DLYTLSSSVTVPSSPRPSETVTCNVAHPASSTKVDKKIVP
        DLYTLSSSVTVTSSTWPSQSITCNVAHPASSTKVDKKIEP
        HTFPALLQS-GLYTMSSSVTVPSSTWPSQTVTCSVAHPASSTTVDKKLEP

K---------CCVECPPCPAPPVAG-PSVFLFPPKPKDTLMISRTPEVT
        KS-------CDKTHTCPPCPAPELLGGPSVFLFPPKPKDTLMISRTPEVT
        K---------YGPPCPSCPAPEFLGGPSVFLFPPKPKDTLMISRTPEVT
        RD-----CGCKPC----ICTVPEVS---SVFIFPPKPKDVLTITLTPKVT
        RG--PTIKPCPPC----KCPAPNLLGGPSVFIFPPKIKDVLMISLSPIVT
        SGPISTINPCPPCKECHKCPAPNLEGGPSVFIFPPNIKDVLMISLTPKVT

CVVVDVSHEDPEVQFNWYVDGMEVHNAKTKPREEQFNSTFRVVSVLTVVH
        CVVVDVSHEDPEVKFNWYVDGVEVHNVKTKPREEQYNSTYRVVSVLTVLH
        CVVVDVSQEDPEVQFNWYVDGVEVHNAKTKPREEQFNSTYRVVRVLTVLH
        CVVVDISKDDPEVQFSWFVDDVEVHTAQTQPREEQFNSTFRSVSELPIMH
        CVVVDVSEDDPDVQISWFVNNVEVHTAQTQTHREDYNSTLRVVSALPIQH
        CVVVDVSEDDPDVQISWFVNNVEVHTAQTQTHREDYNSTIRVVSTLPIQH

QDWLNGKEYKCKVSNKGLPAPIEKTISKTKGQPREPQVYTLPPSREEMTK
        QNWMNGKEYKCKVSNKALPAPIEKTISKAKVQPREPQVYTLPPSRDELTK
        QDWLNGKEYKCKVSNKGLPSSIEKTISKAKGQPREPQVYTLPPSQEEMTK
        QDWLNGKEFKCRVNSAAFPAPIEKTISKTKGRPKAPQVYTIPPPKEQMAK
        QDWMSGKEFKCKVNNKDLPAPIERTISKPKGSVRAPQVYVLPPPEEEMTK
        QDWMSGKEFKCKVNNKDLPSPIERTISKIKGLVRAPQVYILPPPAEQLSR

NQVSLTCLVKGFYPSDIAVEWESNGQPENNYKTTPPMLDSDGSFFLYSKL
        NQVSLTCLVKGFYPSDIAVEWESNGQPENNYKTTPPVLDSVGSFFLYSKL
        NQVSLTCLVKGFYPSDIAVEWESNGQPEDNYKTTPPVLDSDGSFFLYSRL
        DKVSLTCMITDFFPEDITVEWQWNGQPAENYKNTQPIMNTNGSYFVYSKL
        KQVTLTCMVTDFMPEDIYVEWTNNGKTELNYKNTEPVLDSDGSYFMYSKL
        KDVSLTCLVVGFNPGDISVEWTSNGHTEENYKDTAPVLDSDGSYFIYSKL

TVDKSRWQQGNVFSCSVMHEALHNHYTQKSLSLSPGK--
        TVDKSRWQQGNVFSCSVMHEALHNHYQQRSLSLSPGK--
        TVDKSRWQEGNVFSCSVMHEALHNHYTQKSLSLSPGK--
        NVQKSNWEAGNTFTCSVLHEGLHNHHTEKSLSHSPGKGK
        RVEKKNWVERNSYSCSVVHEGLHNHHTTKSFSRTPGKV-
        NMKTSKWEKTDSFSCNVRHEGLKNYYLKKTISRSPGKV-
```

Fig. 12

HLA-DR SPECIFIC ANTIBODIES, COMPOSITIONS AND METHODS

RELATED APPLICATIONS

This application claims priority of U.S. Provisional Patent Application No. 60/608,944, filed Dec. 15, 2003.

A "Substitute Sequence Listing" has been submitted with this application in the form of a text file, created 3 Dec. 2010, and named "576368129US00seqlist.txt" (81,920 bytes), the contents of which are incorporated herein by reference in their entirety.

TECHNICAL FIELD OF THE INVENTION

The present invention relates generally to the fields of immunology and molecular biology. More specifically, this invention provides HLA-DR-specific antibodies and methods for the preparation of HLA-DR-specific antibodies. Also provided are compositions and methods comprising HLA-DR-specific antibodies. Antibodies presented herein bind specifically to the HLA-DR antigen and induce apoptosis in HLA-DR expressing tumor cells. Within certain embodiments, apoptotic HLA-DR-specific antibodies exhibit reduced levels of immunosuppressive activity. Antibodies of the present invention will find use in diagnostic methods, as well as in compositions and methods for the treatment of cancers associated with HLA-DR positive tumor cells.

BACKGROUND OF THE INVENTION

Class II major histocompatibility complex (MHC) molecules, constitutively expressed on normal antigen presenting cells (APC), are responsible for the presentation of antigen-derived peptides to CD4+ helper T (Th) cells. Babbitt et al., *Nature* 317:359-361 (1985) and Truman et al., *Blood* 89(6): 1996-2007 (1997). Signaling via these molecules initiates the generation of second messengers leading to programmed cell death (PCD or apoptosis) of activated B lymphocytes. Besides antigen presentation, class II molecules transduce signals that can modulate cell growth and certain class II MHC-specific monoclonal antibodies have been shown to induce apoptosis of cancer cells. Newell et al., *Proc. Natl. Acad. Sci. U.S.A.* 90(22):10459-10463 (1993).

HLA class II molecules are constitutively expressed on human B lymphocytes and are induced on human T lymphocytes after activation. Up to 60% of cell death has been observed after stimulation of lymphocytes via HLA-DR molecules. Certain HLA-DR-specific antibodies cause up to a 90% decrease in the cell surface expression of class II molecules. HLA-DR-specific antibodies and fragments thereof do not affect the expression of HLA-DP and HLA-DQ molecules. Truman, et al., *Int. Immunol.* 6(6):887-896 (1994).

Class II MHC-specific antibodies that have been shown to induce apoptosis of cancer cells frequently also interfere with normal Th cell functions. Vidovic et al., *Eur. J. Immunol.* 25:3349-3355 (1995). The majority of currently available apoptosis-inducing class II-specific monoclonal antibodies recognize epitopes located on the first protein domains of the HLA-DR heterodimer, in apparent close proximity to the peptide-binding site, and these antibodies interfere with antigen presentation, causing a potent in vitro and in vivo inhibition of Th responses, in addition to being cytotoxic for B lymphoblastoid cell lines and for a small proportion of normal activated B cells. Their $F(ab')_2$ fragments mediate both down-regulation and cytotoxicity, whereas their monovalent Fab fragments are not cytotoxic, but retain the down-regulatory and T cell inhibitory properties. Id.

Thus, most HLA-DR-specific apoptotic monoclonal antibodes available in the art exhibit sufficient immunosuppressive activity to limit their utility in compositions and methods for the treatment of cancers involving HLA-DR-positive cells. Accordingly, there remains a need in the art for improved HLA-DR-specific antibodies, such as for example non-immunosuppressive apoptotic HLA-DR-specific antibodies, as well as compositions and methods comprising such antibodies that overcome these deficiencies.

SUMMARY OF THE INVENTION

The present invention addresses these and other related needs by providing, inter alia, HLA-DR-specific antibodies and antigen-binding fragments thereof that are capable of triggering apoptosis in HLA-DR positive tumor cells. This invention is based, in part, on the discovery that antibodies that specifically react with human major histocompatibility complex (MHC) class II can induce apoptosis of cells expressing HLA-DR molecules on their surface. Antibodies of the present invention are highly specific in that the HLA-DR-specific antibodies affect neither the viability nor function of non-tumor/non-neoplastic cells that express HLA-DR. Within certain embodiments, the apoptotic activity of inventive HLA-DR antibodies can be achieved without simultaneous suppression of class II-dependent immune responses.

An important practical implication of the present invention is that a monoclonal antibody, designated "DN1924," and a murine/human variant of DN1924, designated "chimeric DN1924," may be effective for the selective antibody-based therapy of HLA class II positive neoplasms including, but not limited to, blood cell neoplasms, e.g., plasmacytoma/multiple myeloma, Hodgkin's and non-Hodgkin's lymphomas, and B cell leukemias. In vitro studies indicate that the DN1924 and chimeric DN1924 monoclonal antibodies do not interfere with normal Th function, therefore, therapy with the DN1924 and/or chimeric DN1924 should not affect the subject's normal HLA-DR-expressing cells. Accordingly, it would be reasonable to expect fewer side effects than with the currently available therapeutic agents.

Thus, within certain aspects, the present invention provides non-human monoclonal HLA-DR-specific apoptotic antibodies. Non-human monoclonal antibodies of the present invention can be isolated from a variety of animal species including, but not limited to, non-human primate, sheep, pig, cow, horse, donkey, poultry, rabbit, mouse, rat, guinea pig, hamster, dog, and cat origin. HLA-DR-specific apoptotic non-human monoclonal antibodies are exemplified herein by (1) the immunosuppressive antibody DN1921 comprising the heavy and light chain variable domains presented in SEQ ID NO: 13 and SEQ ID NO: 2, respectively, which are encoded by the polynucleotides of SEQ ID NO: 46 and 45, respectively and (2) the non-immunosuppressive antibody DN 1924 comprising the heavy and light chain variable domains presented in SEQ ID NO: 35 and SEQ ID NO: 24, respectively, which are encoded by the polynucleotides of SEQ ID NO: 48 and 47, respectively.

Each of the DN1921 and DN1924 antibodies exemplified herein further comprise a murine $IgG_1$ heavy and IgKappa light chain constant domain. Within related alternative embodiments, DN 1921 and/or DN 1924 monoclonal antibodies may comprise the aforementioned heavy and light chain variable domains and a murine heavy chain constant domain from an antibody isotype selected from the group consisting of IgM, IgD, IgG$_2$, IgG$_3$, IgG$_4$, IgE, IgA$_1$ and IgA$_2$.

Also provided are antigen-binding fragments, variants, and derivatives of DN1921 and DN1924 heavy and light chains. Within certain embodiments, variants of DN1921 comprise heavy and light chain variable domains that are at least 70% identical to SEQ ID NO: 13 and 2, respectively. Within other embodiments, variants of DN1921 comprise heavy and light chain variable domains that are at least 80%, 90%, or 95% identical to SEQ ID NO: 13 and 2, respectively. Within still further embodiments, variants of DN1921 comprise heavy and light chain variable domains that are at least 98% or 99% identical to SEQ ID NO: 13 and 2, respectively.

Within alternative embodiments, variants of DN1924 comprise heavy and light chain variable domains that are at least 70% identical to SEQ ID NO: 35 and 24, respectively. Within other embodiments, variants of DN1924 comprise heavy and light chain variable domains that are at least 80%, 90%, or 95% identical to SEQ ID NO: 35 and 24, respectively. Within still further embodiments, variants of DN1924 comprise heavy and light chain variable domains that are at least 98% or 99% identical to SEQ ID NO: 35 and 24, respectively.

Other aspects of the present invention provide non-human/human chimeric HLA-DR-specific monoclonal antibodies wherein the chimeric antibodies comprise a non-human variable domain operably fused to a human constant domain. Non-human/human chimeric HLA-DR-specific monoclonal antibodies of the present invention induce apoptosis in HLA-DR expressing tumor cells, but not normal cells, to which the antibody is bound. Within certain embodiments, inventive non-human/human chimeric HLA-DR-specific apoptotic monoclonal antibodies are non-immunosuppressive when administered in vivo to a subject.

Non-human monoclonal antibody variable domains suitable for construction of chimeric monoclonal antibodies of the present invention can be isolated from a variety of animal species including, but not limited to, non-human primate, sheep, pig, cow, horse, donkey, poultry, rabbit, mouse, rat, guinea pig, hamster, dog, and cat origin. Human antibody heavy chain constant domains can be isolated from antibody isotypes selected from the group consisting of IgM, IgD, IgG$_1$, IgG$_2$, IgG$_3$, IgG$_4$, IgE, IgA$_1$ and IgA$_2$.

Exemplary HLA-DR-specific chimeric monoclonal antibodies disclosed herein comprise heavy and light chain variable domains of murine monoclonal antibody DN1921 (SEQ ID NO: 13 and 2, respectively) operably fused to human heavy and light chain constant domains (SEQ ID NO: 14 and 3, respectively). The chimeric DN1921 monoclonal antibody disclosed herein is capable of inducing apoptosis in a tumor cell expressing HLA-DR and is immunosuppressive when administered in vivo. The amino acid sequence of the exemplary full-length chimeric DN1921 monoclonal antibody heavy chain is presented herein as SEQ ID NO: 12. The amino acid sequence of the exemplary full-length chimeric DN1921 monoclonal antibody light chain is presented herein as SEQ ID NO: 1.

Also provided are variants of the chimeric DN1921 heavy and light chains of SEQ ID NO: 12 and 1, respectively. Within certain embodiments, variants of chimeric DN1921 heavy and light chains are at least 70% identical to SEQ ID NO: 12 and 1, respectively. Within other embodiments, variants of chimeric DN1921 heavy and light chains are at least 80%, 90%, or 95% identical to SEQ ID NO: 12 and 1, respectively. Within still further embodiments, variants of chimeric DN 1921 heavy and light chains are at least 98% or 99% identical to SEQ ID NO: 12 and 1, respectively.

Alternative exemplary HLA-DR-specific chimeric monoclonal antibodies disclosed herein comprise heavy and light chain variable domains of murine monoclonal antibody DN1924 (SEQ ID NO: 35 and 24, respectively) operably fused to human heavy and light chain constant domains (SEQ ID NO: 36 and 25, respectively). The chimeric DN1924 monoclonal antibody disclosed herein is capable of inducing apoptosis in a tumor cell expressing HLA-DR and is non-immunosuppressive when administered in vivo. The amino acid sequence of the exemplary full-length chimeric DN1924 monoclonal antibody heavy chain is presented herein as SEQ ID NO: 34. The amino acid sequence of the exemplary full-length chimeric DN1924 monoclonal antibody light chain is presented herein as SEQ ID NO: 23.

Within alternative embodiments, variants of the chimeric DN1924 heavy and light chains of SEQ ID NO: 34 and 23, respectively. Within certain embodiments, variants of chimeric DN1924 heavy and light chains are at least 70% identical to SEQ ID NO: 34 and 23, respectively. Within other embodiments, variants of chimeric DN1924 heavy and light chains are at least 80%, 90%, or 95% identical to SEQ ID NO: 34 and 23, respectively. Within still further embodiments, variants of chimeric DN1924 heavy and light chains are at least 98% or 99% identical to SEQ ID NO: 34 and 23, respectively.

Within still further embodiments, HLA-DR-specific apoptotic antibodies are humanized monoclonal antibodies wherein the humanized antibody comprises one or more non-human complementarity determining region (CDR) operably fused to a human variable domain framework region (FR) to create heavy and light chain variable domains, which are operably fused to human constant domain heavy and light chains, exemplified herein by the heavy chain IgG$_2$ and light chain IgKappa constant domains presented in SEQ ID NO: 14 and 3, respectively.

Exemplary HLA-DR-specific humanized monoclonal antibodies of the present invention comprise one or more complementarity determining region (CDR) of murine monoclonal antibody DN1921 heavy chain variable domain (SEQ ID NO: 13) operably fused to human heavy chain framework (FR) domains to create a humanized HLA-DR-specific heavy chain variable domain that is, optionally, operably fused to human heavy chain constant domain wherein the heavy chain constant domain is selected from the group consisting of IgM, IgD, IgG$_1$, IgG$_2$, IgG$_3$, IgG$_4$, IgE, IgA$_1$ and IgA$_2$ and the human IgKappa light chain constant domain presented in SEQ ID NO: 14.

Alternatively or additionally, exemplary HLA-DR-specific humanized monoclonal antibodies of the present invention comprise one or more complementarity determining region (CDR) of murine monoclonal antibody DN1921 light chain variable domain (SEQ ID NO: 2) operably fused to human light chain framework (FR) domains 1, 2, 3, and/or 4 to create a humanized HLA-DR-specific light chain variable domain that is, optionally, operably fused to a human heavy chain constant domain wherein the constant domain is selected from the group consisting of IgM, IgD, IgG$_1$, IgG$_2$, IgG$_3$, IgG$_4$, IgE, IgA$_1$ and IgA$_2$ and a human light chain constant domain exemplified herein by the human IgKappa light chain constant domain presented in SEQ ID NO: 3.

Humanized monoclonal antibodies based on DN1921 are capable of inducing apoptosis in a tumor cell expressing HLA-DR and are immunosuppressive when administered in vivo. DN1921 CDRs suitable for generating humanized antibodies according to the present invention are presented as SEQ ID NO: 17 (DN1921 V$_H$ CDR1), SEQ ID NO: 19 (DN1921 V$_H$ CDR2), SEQ ID NO: 21 (DN1921 V$_H$ CDR3), SEQ ID NO: 6 (DN1921 $V_L$ CDR1), SEQ ID NO: 8 (DN1921 $V_L$ CDR2), and SEQ ID NO: 10 (DN1921 $V_L$ CDR3).

Futher exemplary HLA-DR-specific humanized monoclonal antibodies of the present invention comprise one or more complementarity determining region (CDR) of murine monoclonal antibody DN 1924 heavy chain variable domain (SEQ ID NO: 35) operably fused to human framework (FR) domains 1, 2, 3, and/or 4 to create a humanized HLA-DR-specific heavy chain variable domain that is, optionally, operably fused to a human heavy chain constant domain wherein the heavy chain constant domain is selected from the group consisting of IgM, IgD, $IgG_1$, $IgG_2$, $IgG_3$, $IgG_4$, IgE, $IgA_1$ and IgA2 and the light chain constant domain is exemplified herein by the human IgKappa light chain constant domain presented in SEQ ID NO: 36.

Alternatively or additionally, further exemplary HLA-DR-specific humanized monoclonal antibodies of the present invention comprise one or more complementarity determining region (CDR) of murine monoclonal antibody DN1924 light chain variable domain (SEQ ID NO: 24) operably fused to human framework (FR) domains 1, 2, 3, and/or 4 to create a humanized HLA-DR-specific light chain variable domain that is, optionally, operably fused to a human heavy chain constant domain wherein the constant domain is selected from the group consisting of IgM, IgD, $IgG_1$, $IgG_2$, IgG3, IgG4, IgE, $IgA_1$, and $IgA_2$ and the light chain constant domain is exemplified by the human IgKappa light chain constant domain presented in SEQ ID NO: 25.

Humanized monoclonal antibodies based on DN1924 are capable of inducing apoptosis in a tumor cell expressing HLA-DR and are non-immunosuppressive when administered in vivo. DN1924 CDRs suitable for generating humanized antibodies according to the present invention are presented as SEQ ID NO: 39 (DN1924 $V_H$ CDR1), SEQ ID NO: 41 (DN1924 $V_H$ CDR2), SEQ ID NO: 43 (DN1924 $V_H$ CDR3), SEQ ID NO: 28 (DN1924 $V_L$ CDR1), SEQ ID NO: 30 (DN1924 $V_L$ CDR2), and SEQ ID NO: 32 (DN1924 $V_L$ CDR3).

The present invention also provides compositions and methods comprising one or more non-human monoclonal, chimeric, and/or humanized HLA-DR-specific antibody presented herein. Compositions comprising such an HLA-DR-specific antibody are suitable for in vivo administration and are effective in triggering apoptosis of tumor cells expressing HLA-DR.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS AND SEQUENCE IDENTIFIERS

FIG. 1 shows a general epitope map of an HLA-DR molecule indicating: CY, cytoplasmic tail; TM, transmembrane part; alpha1 & beta1, the first (extracellular) domains of alpha and beta chains, respectively; and alpha2 & beta2, the second (extracellular) domains of alpha and beta chains, respectively.

FIG. 2 shows the viability of different cell populations after 16 hours coculture with the DN1924 murine monoclonal antibody. Live cells are located in the lower right quadrants of the two-dimensional dot-plots. PBMC corresponds to peripheral blood mononuclear cells.

Figure 7A:
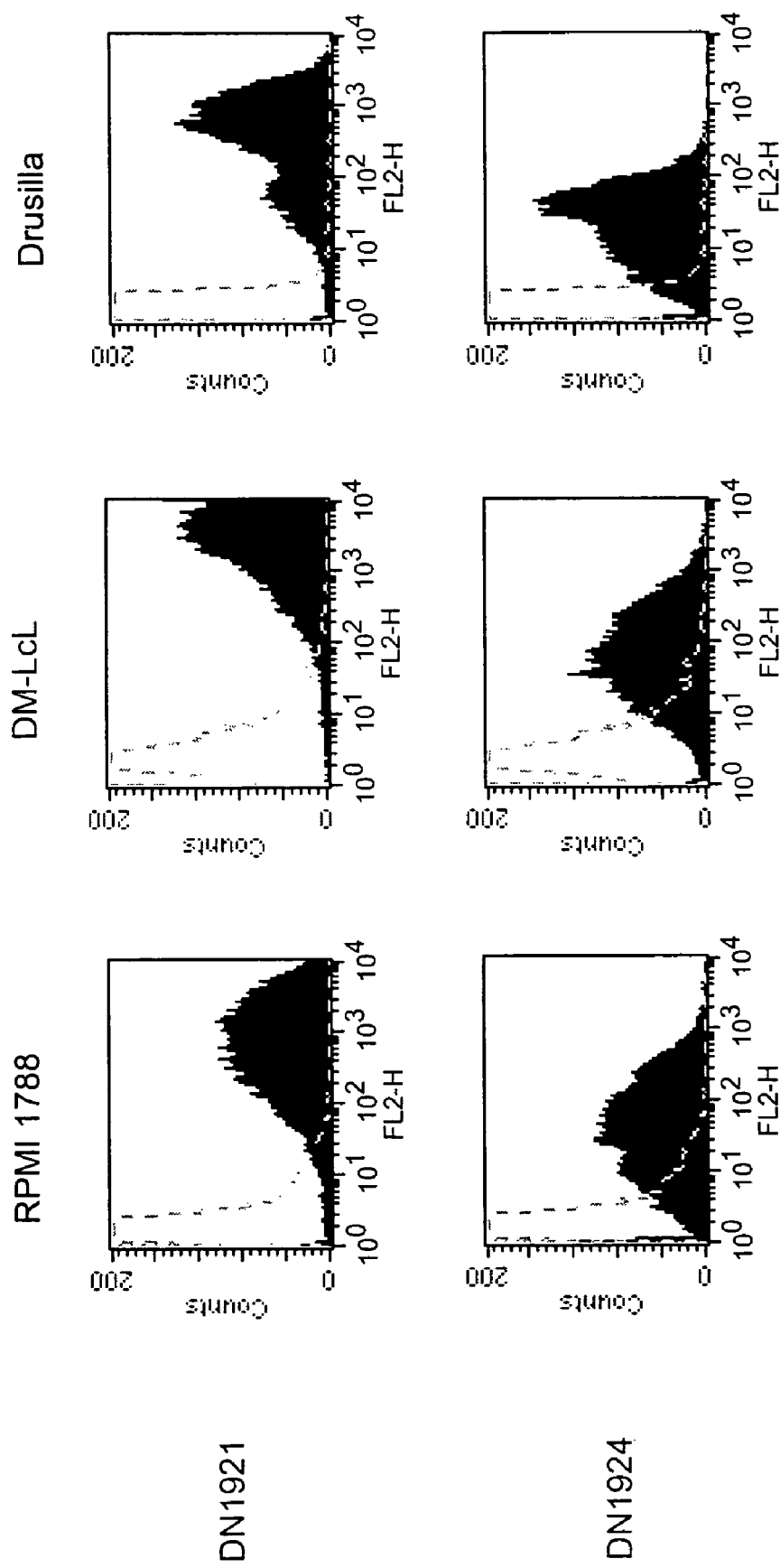
Figure 7B:
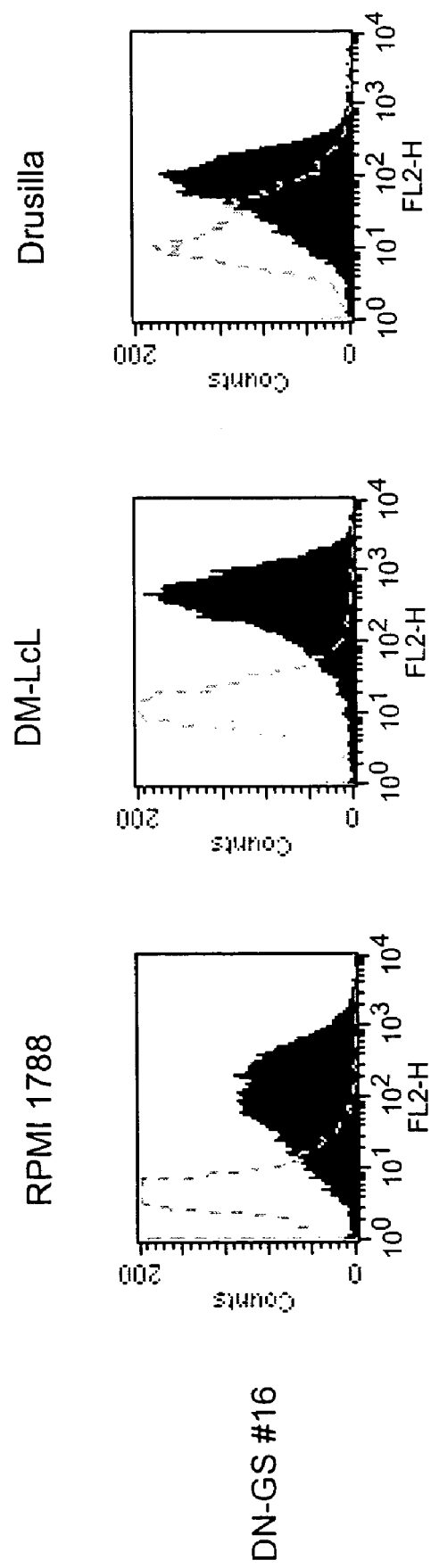

FIGS. 7A-D are FACS data demonstrating the specific binding of DN1921 and DN1924 (FIG. 7A), chimeric DN1924 (FIG. 7B), and chimeric DN1921 (FIG. 7C) to HLA-DR-expressing cells. FIG. 7D shows that neither DN1921 nor DN1924 specifically bind U937 cells not expressing HLA-DR.

Figure 8B:
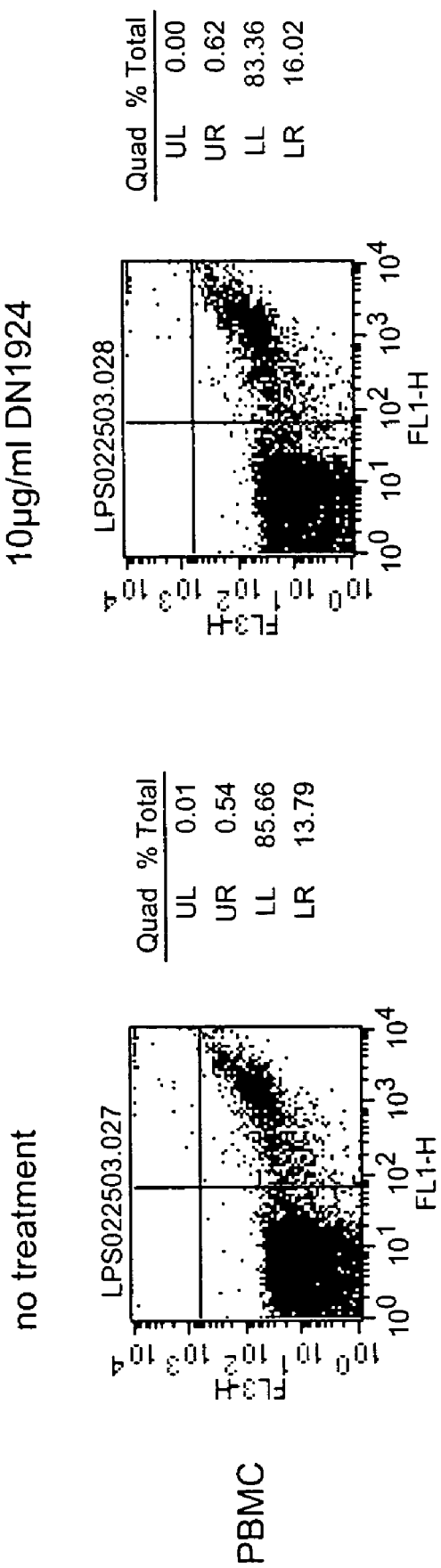
Figure 8C:
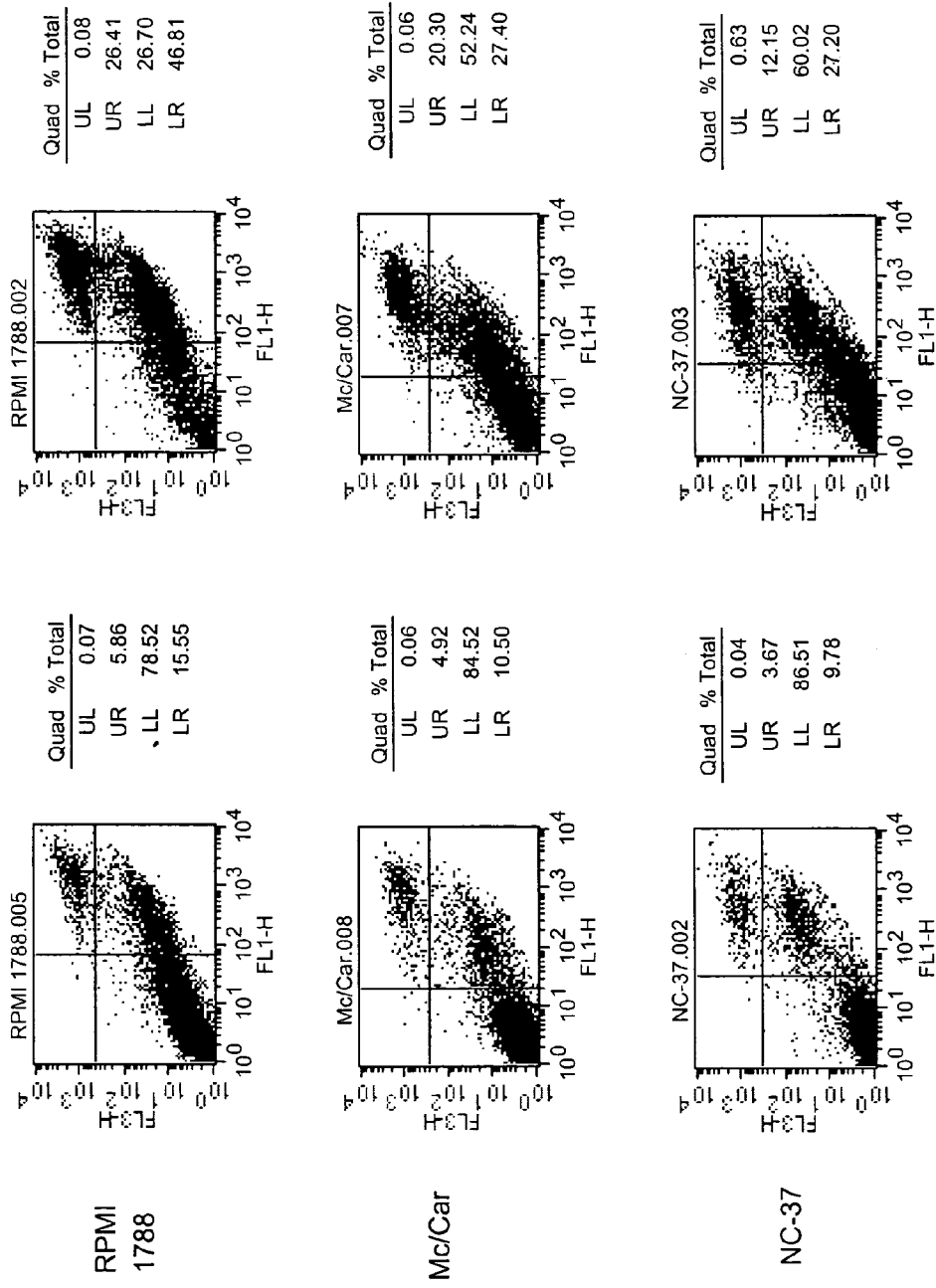
Figure 8D:
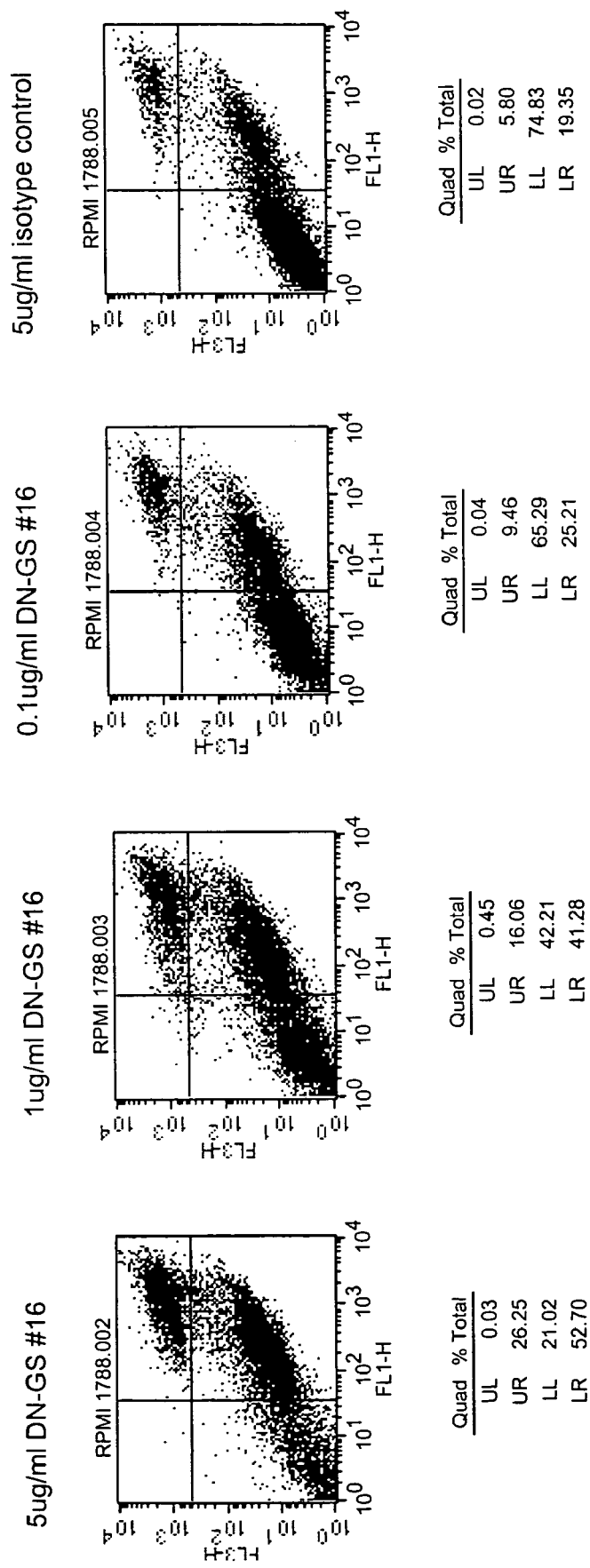
Figure 8E:
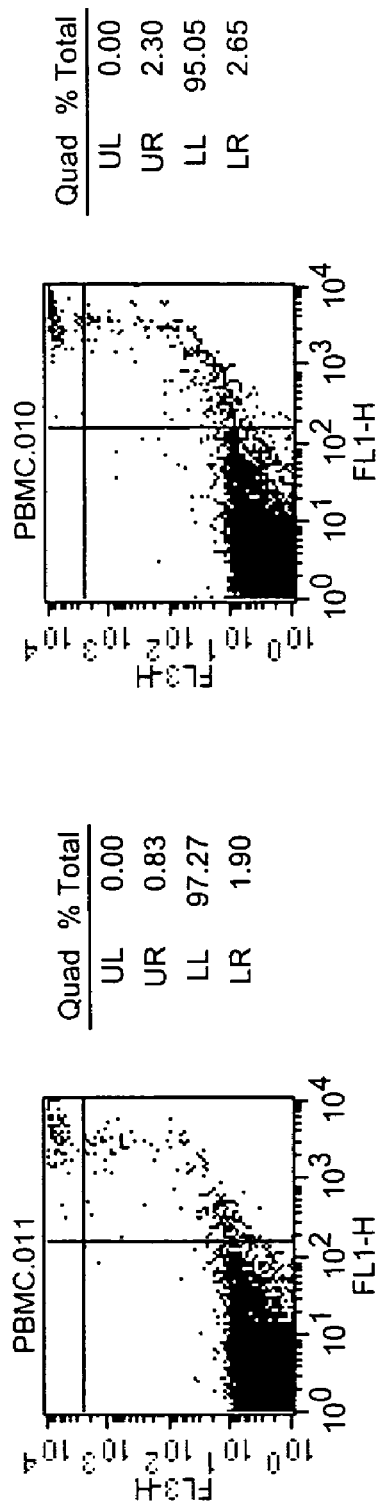
Figure 8F:
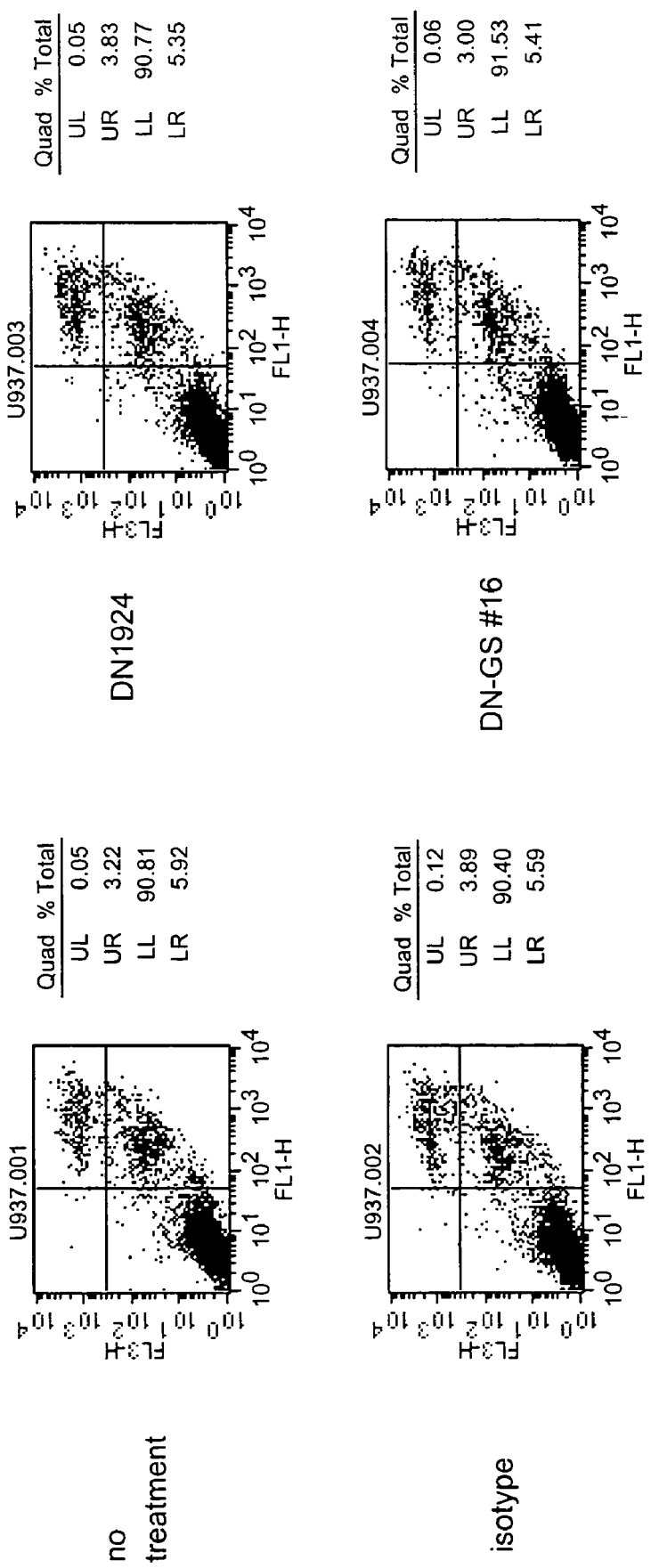

FIGS. 8A-F are FACS data demonstrating that DN1924 induces apoptotic activity in HLA-DR-positive tumor cells (FIG. 8A), that DN1924 does not induce apoptosis in normal HLA-DR-positive cells (FIG. 8B), that chimeric DN1924 induces apoptosis in HLA-DR-positive tumor cells (FIG. 8C), that induction of apoptosis by chimeric DN1924 is dose dependent (FIG. 8D), that chimeric DN1924 does not induce apoptosis in normal HLA-DR-positive cells (FIG. 8E), and that DN1924 does not induce apoptosis in HLA-DR-negative tumor cells (FIG. 8F).

Figure 9:
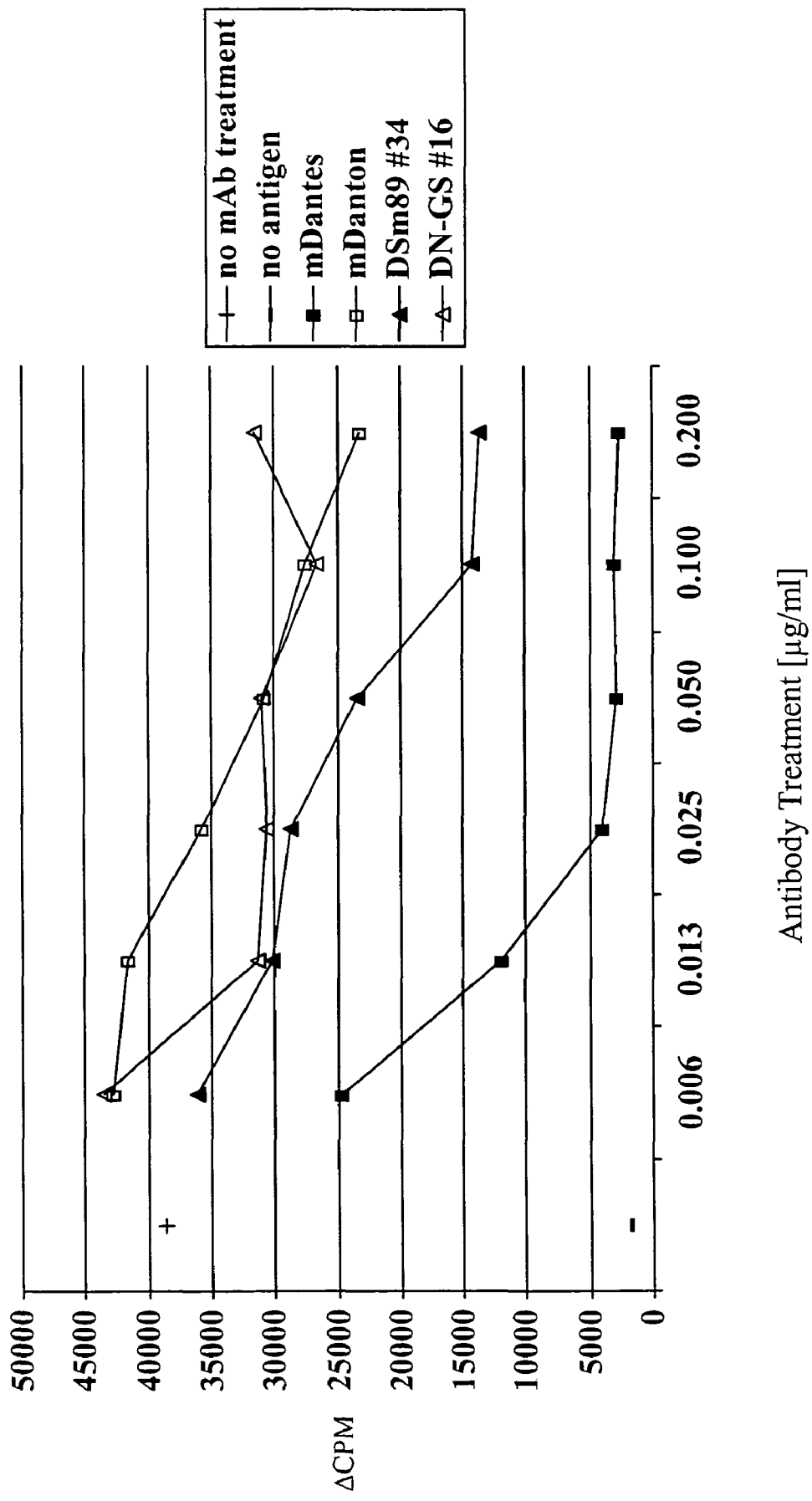

FIG. 9 is a graph demonstrating inhibition of PAP/HLA-DR-specific Paperino responses by murine and chimeric DN1921 but not by murine or chimeric DN1924 HLA-DR-specific monoclonal antibodies.

Figure 10:
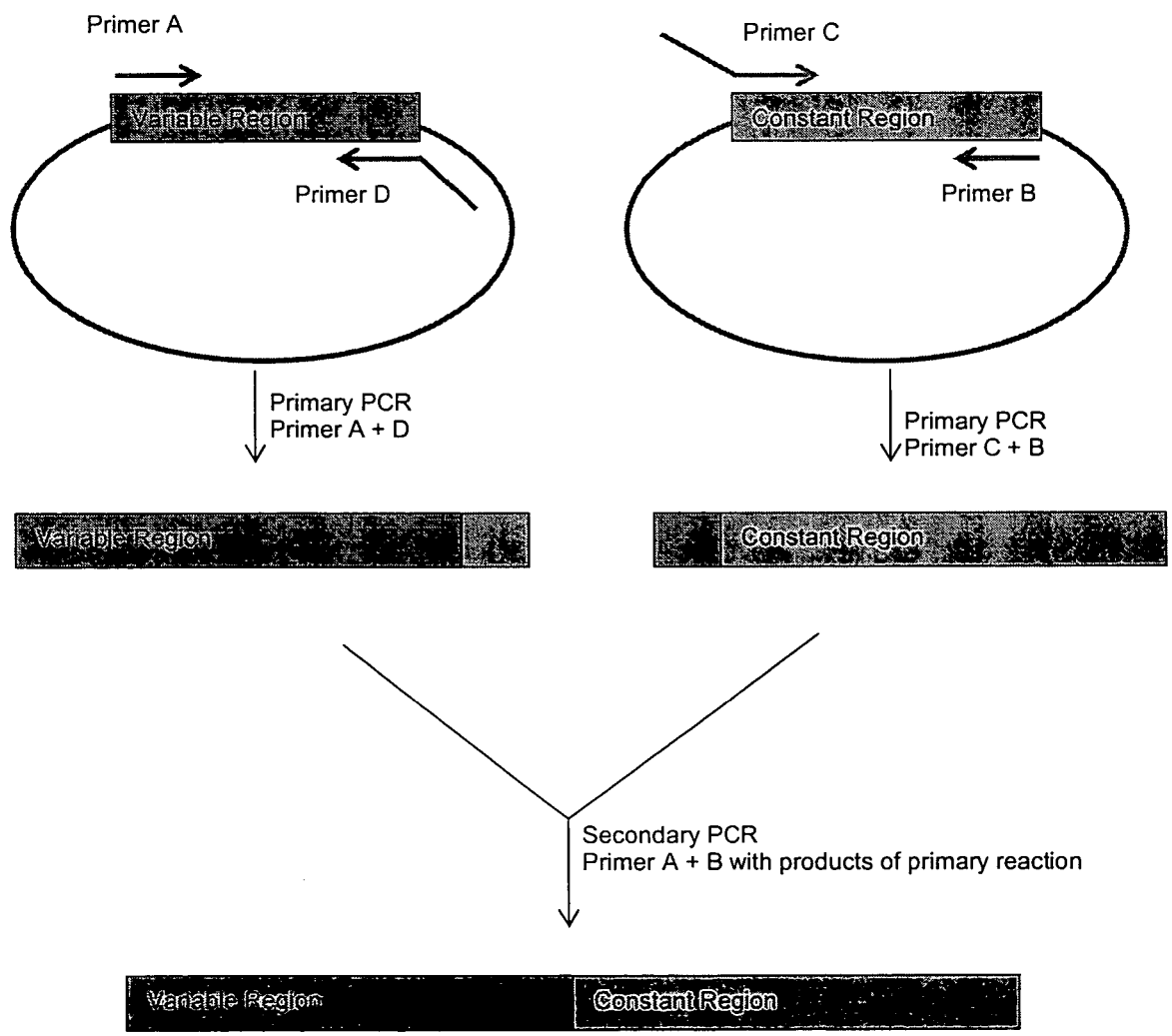
Figure 13A:
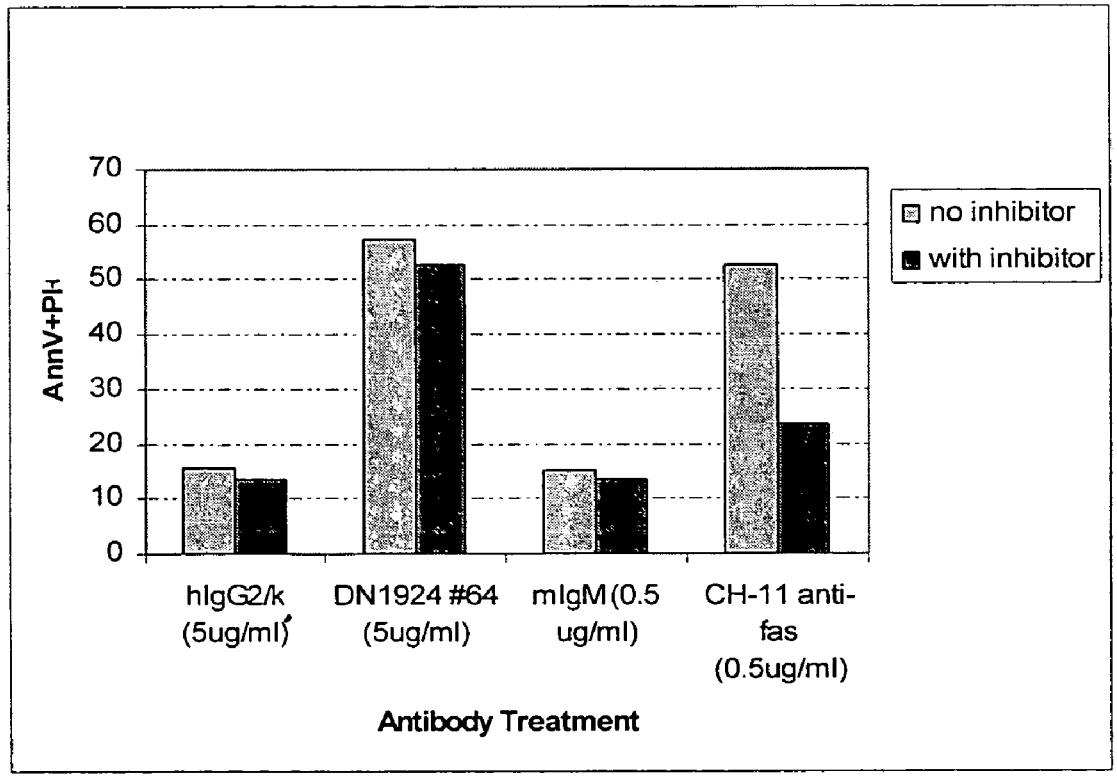
Figure 13B:
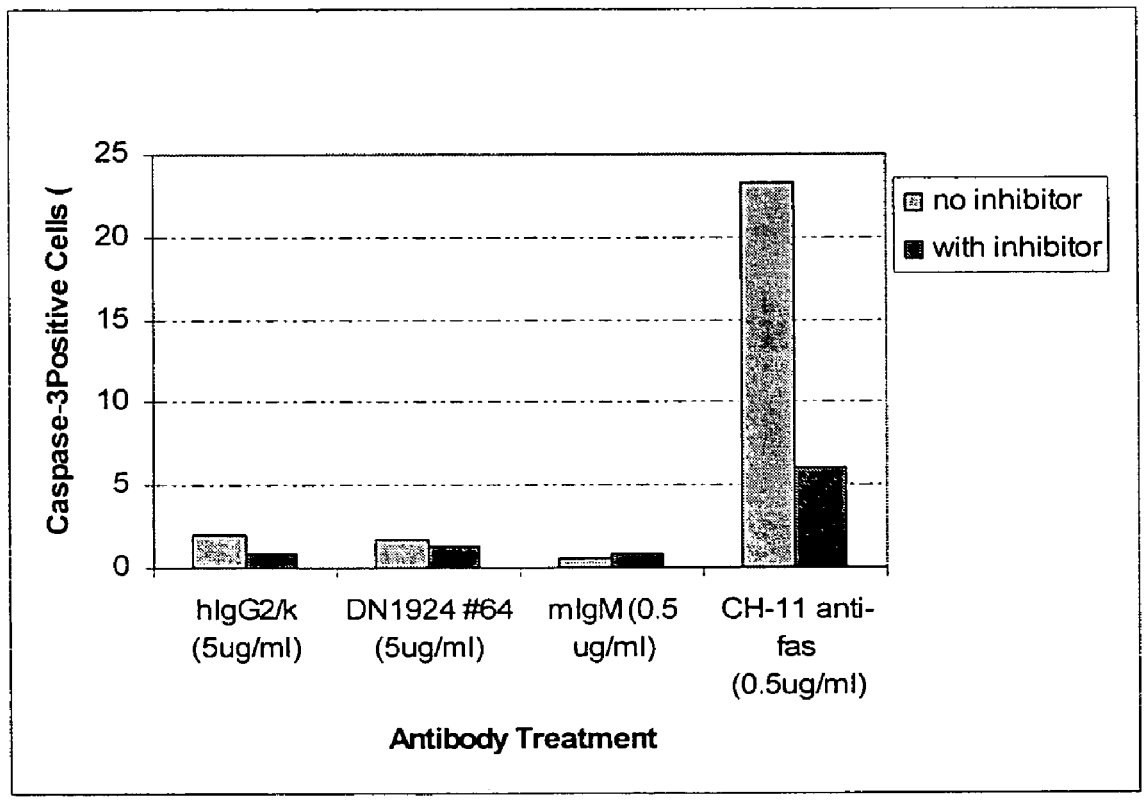
Figure 13C:
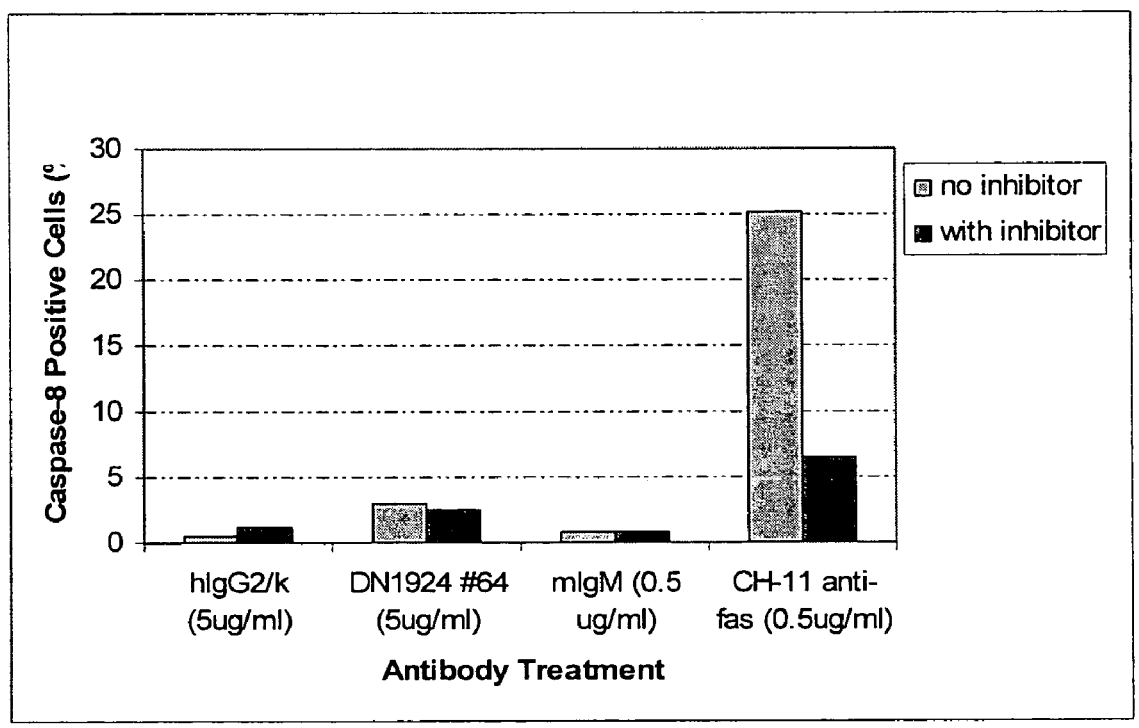
Figure 13D:
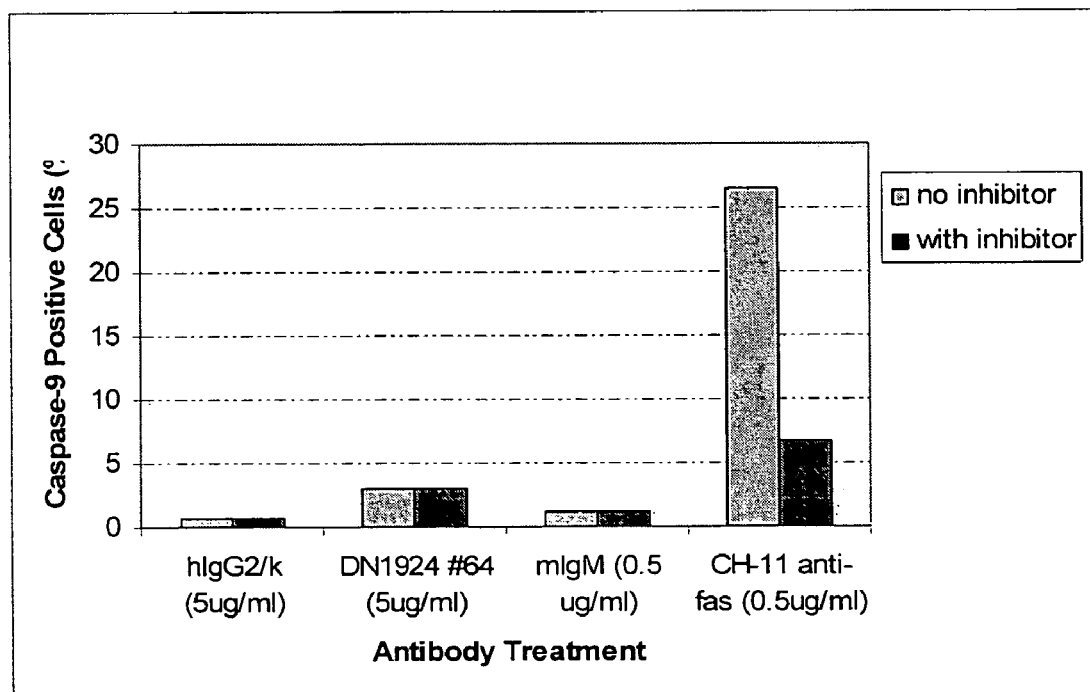

FIG. 10 is a diagramatic representation of the construction of plasmid vectors for expressing chimeric DN1921 and chimeric DN1924.

FIG. 11 is an IgKappa constant region alignment: The top two lines are two different amino acid sequences for human IgKappa (top line: GenBank Accession No. AAA58989.1, herein identified as SEQ ID NO: 3; middle line: residues 243 to 349 of GenBank Accession No. AAA7002.1 and herein identified as SEQ ID NO: 79); bottom line: residues 113 to 219 of the amino acid sequence of murine IgKappa (GenBank Accession No. AAA67525.1, herein identified as SEQ ID NO: 80).

FIG. 12 is an IgG constant region alignment: The top three lines are human (h)IgG2, hIgG1, and hIgG4 (GenBank Accession No. CAC12842.1an amino acid sequence herein identified as SEQ ID NO:73; residues 139 to 467 of GenBank Accession No. AAb86467.2, herein identified as SEQ ID NO:74; and GenBank Accession No. CAC202457.1 identified as SEQ ID NO:75, respectively). The bottom three lines are murine (m) IgG1amino acid sequence identified as SEQ ID NO:76, IgG2a amino acid sequence identified as SEQ ID NO:77, and IgG2b amino acid sequence identified as SEQ ID NO:78, respectively).

FIGS. 13A-D are bar graphs demonstrating that murine/human chimeric DN1924 anti-HLA-DR-mediated apoptosis is caspase independent (FIG. 13A) and that neither caspase 3 (FIG. 13B), caspase 8 (FIG. 13C), nor caspase 9 (FIG. 13D) is activated in chimeric DN1924 treated cells.

Figure 14:
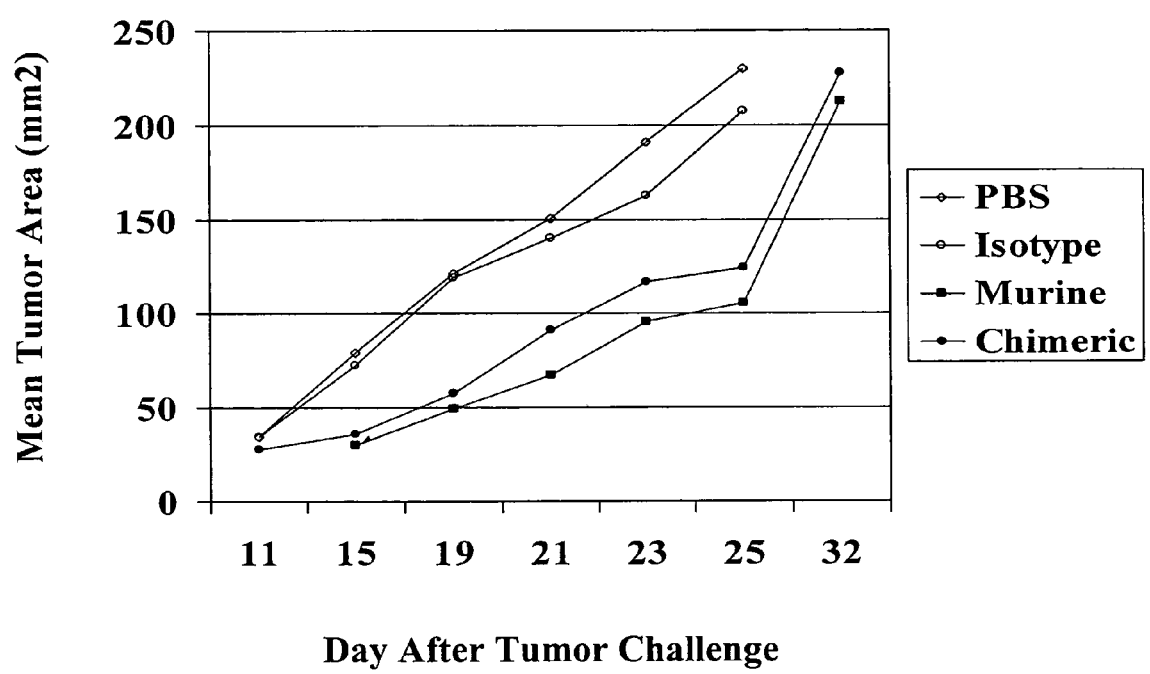

FIG. 14 is a graph demonstrating that in vivo subcutaneous administration of murine/human chimeric DN1924 anti-HLA-DR antibody is effective in reducing the rate of tumor growth in a Raji xenograft scid mouse animal model system.

Figure 15:
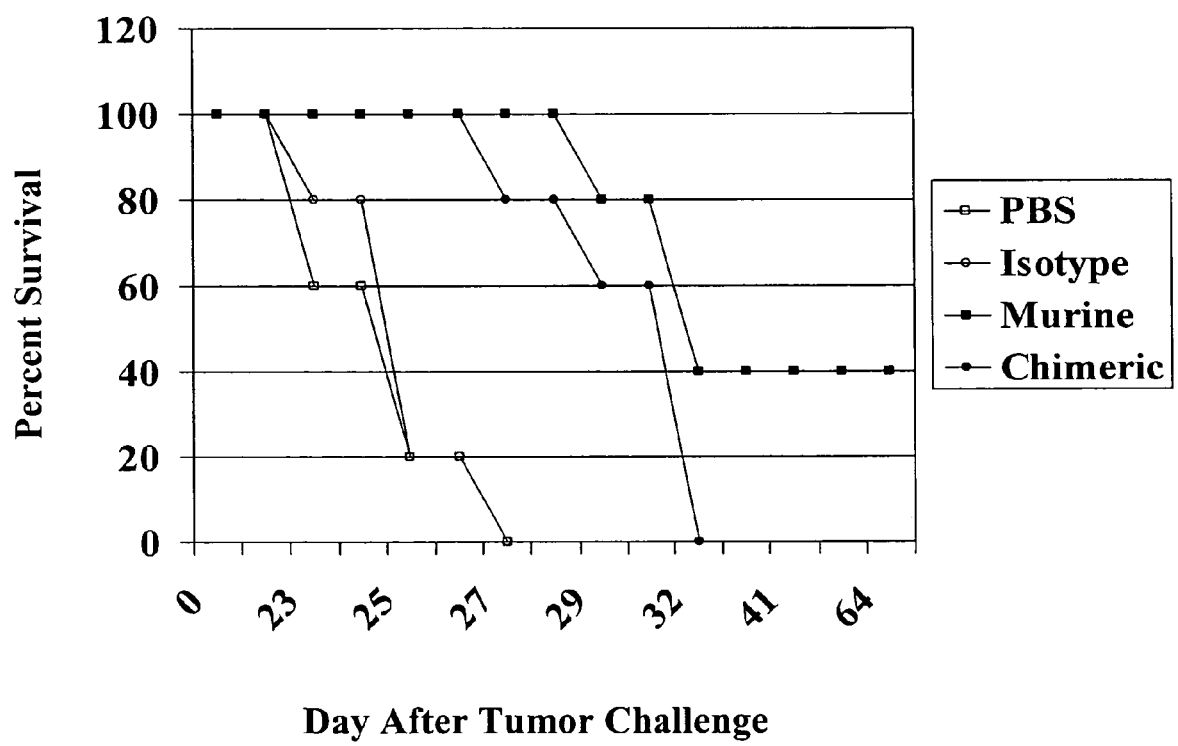

FIG. 15 is a graph demonstrating that in vivo subcutaneous administration of murine/human chimeric DN1924 anti- HLA-DR antibody is effective in promoting increased survival in a Raji xenograft scid mouse animal model system.

SEQ ID NO: 1 is the amino acid sequence of chimeric DN1921 full-length antibody light chain.

SEQ ID NO: 2 is the amino acid sequence of chimeric DN1921 light chain variable region.

SEQ ID NO: 3 is the amino acid sequence of chimeric DN1921 light chain constant region (human IgG$_2$ kappa).

SEQ ID NO: 4 is the amino acid sequence of chimeric DN1921 light chain leader sequence.

SEQ ID NO: 5 is the amino acid sequence of chimeric DN1921 light chain framework region 1 (FR1).

SEQ ID NO: 6 is the amino acid sequence of chimeric DN1921 light chain complementarity determining region 1 (CDR1).

SEQ ID NO: 7 is the amino acid sequence of chimeric DN1921 light chain FR2.

SEQ ID NO: 8 is the amino acid sequence of chimeric DN1921 light chain CDR2.

SEQ ID NO: 9 is the amino acid sequence of chimeric DN1921 light chain FR3.

SEQ ID NO: 10 is the amino acid sequence of chimeric DN1921 light chain CDR3.

SEQ ID NO: 11 is the amino acid sequence of chimeric DN1921 light chain FR4.

SEQ ID NO: 12 is the amino acid sequence of chimeric DN1921 full-length antibody heavy chain.

SEQ ID NO: 13 is the amino acid sequence of chimeric DN1921 heavy chain variable region.

SEQ ID NO: 14 is the amino acid sequence of chimeric DN1921 heavy chain constant region (human IgG$_2$).

SEQ ID NO: 15 is the amino acid sequence of chimeric DN1921 heavy chain leader sequence.

SEQ ID NO: 16 is the amino acid sequence of chimeric DN1921 heavy chain FR1.

SEQ ID NO: 17 is the amino acid sequence of chimeric DN1921 heavy chain CDR1.

SEQ ID NO: 18 is the amino acid sequence of chimeric DN1921 heavy chain FR2.

SEQ ID NO: 19 is the amino acid sequence of chimeric DN1921 heavy chain CDR2.

SEQ ID NO: 20 is the amino acid sequence of chimeric DN1921 heavy chain FR3.

SEQ ID NO: 21 is the amino acid sequence of chimeric DN1921 heavy chain CDR3.

SEQ ID NO: 22 is the amino acid sequence of chimeric DN1921 heavy chain FR4.

SEQ ID NO: 23 is the amino acid sequence of chimeric DN1924 full-length antibody light chain.

SEQ ID NO: 24 is the amino acid sequence of chimeric DN1924 light chain variable region.

SEQ ID NO: 25 is the amino acid sequence of chimeric DN1924 light chain constant region (IgKappa).

SEQ ID NO: 26 is the amino acid sequence of chimeric DN1924 light chain leader sequence.

SEQ ID NO: 27 is the amino acid sequence of chimeric DN1924 light chain FR1.

SEQ ID NO: 28 is the amino acid sequence of chimeric DN1924 light chain CDR1.

SEQ ID NO: 29 is the amino acid sequence of chimeric DN1924 light chain FR2.

SEQ ID NO: 30 is the amino acid sequence of chimeric DN1924 light chain CDR2.

SEQ ID NO: 31 is the amino acid sequence of chimeric DN1924 light chain FR3.

SEQ ID NO: 32 is the amino acid sequence of chimeric DN1924 light chain CDR3.

SEQ ID NO: 33 is the amino acid sequence of chimeric DN1924 light chain FR4.

SEQ ID NO: 34 is the amino acid sequence of chimeric DN1924 full-length antibody heavy chain.

SEQ ID NO: 35 is the amino acid sequence of chimeric DN1924 heavy chain variable region.

SEQ ID NO: 36 is the amino acid sequence of chimeric DN1924 heavy chain constant region (IgG$_2$).

SEQ ID NO: 37 is the amino acid sequence of chimeric DN1924 heavy chain leader sequence.

SEQ ID NO: 38 is the amino acid sequence of chimeric DN1924 heavy chain FR1.

SEQ ID NO: 39 is the amino acid sequence of chimeric DN1924 heavy chain CDR1.

SEQ ID NO: 40 is the amino acid sequence of chimeric DN1924 heavy chain FR2.

SEQ ID NO: 41 is the amino acid sequence of chimeric DN1924 heavy chain CDR2.

SEQ ID NO: 42 is the amino acid sequence of chimeric DN1924 heavy chain FR3.

SEQ ID NO: 43 is the amino acid sequence of chimeric DN1924 heavy chain CDR3.

SEQ ID NO: 44 is the amino acid sequence of chimeric DN1924 heavy chain FR4.

SEQ ID NO: 45 is the nucleotide sequence of the polynucleotide encoding DN1921 full-length antibody light chain.

SEQ ID NO: 46 is the nucleotide sequence of the polynucleotide encoding DN1921 full-length antibody heavy chain.

SEQ ID NO: 47 is the nucleotide sequence of the polynucleotide encoding DN 1924 full-length antibody light chain.

SEQ ID NO: 48 is the nucleotide sequence of the polynucleotide encoding DN1924 full-length antibody heavy chain.

SEQ ID NO: 49 is the amino acid sequence of human HLA-DR alpha chain.

SEQ ID NO: 50 is the amino acid sequence of human HLA-DR beta chain.

SEQ ID NO: 51 is the nucleotide sequence encoding human HLA-DR alpha chain of SEQ ID NO: 49.

SEQ ID NO: 52 is the nucleotide sequence encoding human HLA-DR beta chain of SEQ ID NO: 50.

SEQ ID NO: 53 is the amino acid sequence of the murine IgG$_1$ heavy chain constant domain.

SEQ ID NO: 54 is the nucleotide sequence encoding the murine IgG$_1$ heavy chain constant domain of SEQ ID NO: 53.

SEQ ID NO: 55 is the amino acid sequence of the murine IgKappa light chain constant domain.

SEQ ID NO: 56 is the nucleotide sequence encoding the murine IgKappa light chain constant domain of SEQ ID NO: 55.

```
SEQ ID NO: 57 is primer sequence 5' - gccggt
accATGGATTTTGGGCTGATTTTTTTTATTG - 3'.

SEQ ID NO: 58 is primer sequence 5' - gcagcg
gccgcTTATTTACCCGGAGACAGGGAGAGG - 3'.

SEQ ID NO: 59 is primer sequence 5' -
CCACGGTCACCGTCTCCTCAGCCGCCTCCACCAAGGGCCCATCG
GTCTTC - 3'.

SEQ ID NO: 60 is primer sequence 5' -
GAAGACCGATGGGCCCTTGGTGGAGGCGGCTGAGGAGACGGTGA
CCGTGG - 3'.
```

-continued

SEQ ID NO: 61 is primer sequence 5' - gcatgg
taccaccATGTTCTCACTAGCTCTTCTCCTCAG - 3'.

SEQ ID NO: 62 is primer sequence 5' - gcagcg
gccgcTTAACACTCTCCCCTGTTGAAG - 3'.

SEQ ID NO: 63 is primer sequence 5' -
GGGGGGACCAAGCTGGAAATAAAAACTGTGGGTGCACCATCTGT
CTTC - 3'.

SEQ ID NO: 64 is primer sequence 5' - gccggt
accATGGTGTTAAGTCTTCTGTACCTG - 3'.

SEQ ID NO: 65 is primer sequence 5' - gcagcg
gccgcTTATTTACCCGGAGACAGGGAGAGG - 3'.

SEQ ID NO: 66 is primer sequence 5' -
CAGTCACCGTCTCCTCAGCCGCCTCCACCAAGGGCCCATCGGTC
TTC - 3'.

SEQ ID NO: 67 is primer sequence 5' -
GAAGACCGATGGGCCCTTGGTGGAGGCGGCTGAGGAGACGGTGA
CTG - 3'.

SEQ ID NO: 68 is primer sequence 5' - ggcgaat
tcaccATGGAGACACAGTCTCAGGTCTTC - 3'.

SEQ ID NO: 69 is primer sequence 5' - gcagcgg
ccgcTTAACACTCTCCCCTGTTGAAG - 3'.

SEQ ID NO: 70 is primer sequence 5' -
GAGGGGGGACCAAGCTGGAAATAAGAAGTGTGGCTGCACCATCTG
TCTTC - 3'.

DETAILED DESCRIPTION OF THE INVENTION

As indicated above, the present invention is directed to HLA-DR-specific antibodies and compositions and methods comprising HLA-DR-specific antibodies. Antibodies presented herein are effective in inducing a poptosis of tumor cells, but not normal cells, which express HLA-DR. Within certain embodiments, apoptotic HLA-DR-specific antibodies of the present invention further exhibit reduced immunosuppressive activity. Inventive HLA-DR-specific antibodies are useful, inter alia, as agents in the diagnosis and treatment of diseases such as cancers wherein at least a subset of the cancer cells express an HLA-DR antigen.

As used herein, the term "HLA-DR" refers to the "human leukocyte antigen" (HLA) DR gene loci and their protein products, the latter being alloantigens expressed on human leukocytes. Alloantigens are the product of polymorphic genes that distinguish self from foreign tissues. The terms "Class II major histocompatibility complex," "Class II MHC," or "Class II" antigens refer to antigens that are expressed at various levels on various cell types and that play an essential role in the recognition of all protein antigens by T cells. Class II MHC molecules typically bind peptides of from 7 to 30 or more amino acids and form complexes that are recognized by antigen-specific $CD4^+T$ cells. The CD4 molecule binds to the second domain of class II molecules.

The terms "apoptotic cell death," "programmed cell death," or "apoptosis," as used herein, refer to the normal series of events in a cell that leads to its death. Apoptosis plays a vital role in the physiological maintenance of most tissues. It is a normal biological process that allows the elimination of unwanted cells through activation of the cell death program. Apoptosis provides an emergency response to protect organisms from abnormal cells following damage from radiation, viral infection, or aberrant growth, as is the case with cancer, by removing these potentially dangerous cells. Apoptotic cell death results from a complex cascade of cellular events that occur at specific stages of cellular differentiation and in response to specific stimuli and is characterized by condensation of the cytoplasm and nucleus of dying cells.

The terms "tumor," "cancer," or "neoplasm" are used interchangeably herein and refer to a malignant growth that arises from normal tissue, but where cells grow abnormally with an absence of structure. Tumor or cancer cells generally lack the capacity for contact inhibition and may be invasive and/or have the ability to metastasize. Tumor cells that are susceptible to treatment with antibodies of the present invention are characterized by the expression of the Class II major histocompatability antigen HLA-DR.

As used in this specification and the appended claims, the singular forms "a," "an" and "the" include plural references unless the content clearly dictates otherwise.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al., "Molecular Cloning: A Laboratory Manual" (2nd Edition, 1989); Maniatis et al., "Molecular Cloning: A Laboratory Manual" (1982); "DNA Cloning: A Practical Approach, vol. I & II" (D. Glover, ed.); "Oligonucleotide Synthesis" (N. Gait, ed., 1984); "Nucleic Acid Hybridization" (B. Hames & S. Higgins, eds., 1985); "Transcription and Translation" (B. Hames & S. Higgins, eds., 1984); "Animal Cell Culture" (R. Freshney, ed., 1986); Perbal, "A Practical Guide to Molecular Cloning" (1984); Ausubel et al., "Current protocols in Molecular Biology" (New York, John Wiley and Sons, 1987); Bonifacino et al., "Current Protocols in Cell Biology" (New York, John Wiley & Sons, 1999); Coligan et al., "Current Protocols in Immunology" (New York, John Wiley & Sons, 1999); and Harlow and Lane *Antibodies: a Laboratory Manual* Cold Spring Harbor Laboratory (1988).

All publications, patents, and patent applications cited herein, whether supra or infra, are hereby incorporated by reference in their entirety. The present invention will be better understood through the detailed description of the specific embodiments, each of which is described in detail herein below.

HLA-DR-Specific Antibodies

The present invention is directed to antibodies, more particularly monoclonal antibodies, non-human/human chimeric monoclonal antibodies, humanized monoclonal antibodies, and fully-human monoclonal antibodies that specifically bind to HLA-DR and that are capable of inducing apoptosis in a tumor cell, but not a normal cell, when the antibody is bound to HLA-DR expressed on the cell surface. Within certain embodiments, monoclonal antibodies of the present invention are further characterized by reduced levels of immunosuppressive activities.

Exemplified herein are murine monoclonal antibodies designated DN1921 and DN1924 comprising the heavy and light chain variable domains of SEQ ID NO: 13 and 2 (DN1921) and SEQ ID NO: 35 and 24 (DN1924), respectively, operably fused to murine $IgG_1$ heavy and IgKappa light chain constant regions (SEQ ID NOs 53 and 55, respectively); chimeric antibodies comprising the variable regions ($V_H$ and $V_L$) of DN1921 and/or DN1924 and human $IgG_2$ heavy and IgKappa light chain constant regions (SEQ ID NO: 14 and 3 (DN1921) and 36 and 25 (DN1924), respectively); as well as humanized antibodies comprising one or more complementarity determining region (CDR) of DN1921 and/or DN1924 heavy and light chain variable domains operably fused to human framework regions (FR) and human constant domains.

As used herein, the term "antibody" includes monoclonal, chimeric, humanized, and fully-human antibodies as well as biological or antigen-binding fragments and/or portions thereof. Reference herein to an "antibody" includes reference to parts, fragments, precursor forms, derivatives, variants, and genetically engineered or naturally mutated forms thereof and includes amino acid substitutions and labeling with chemicals and/or radioisotopes and the like, so long as the resulting derivative and/or variant retains at least a substantial amount of HLA-DR binding specificity and/or affinity. The term "antibody" broadly includes both antibody heavy and light chains as well as all isotypes of antibodies, including IgM, IgD, IgG$_1$, IgG$_2$, IgG$_3$, IgG$_4$, IgE, IgA$_1$ and IgA$_2$, and also encompasses antigen-binding fragments thereof, including, but not limited to, Fab, F(ab')$_2$, Fc, and scFv.

The term "monoclonal antibody," as used herein, refers to an antibody obtained from a population of substantially homogeneous antibodies, i.e. the individual antibodies comprising the population are identical except for naturally-occurring mutations that do not substantially affect antibody binding specificity, affinity, and/or activity.

An HLA-DR-specific antibody, or antigen-binding fragment thereof, is said to "specifically bind," "immunogically bind," and/or is "immunologically reactive" to HLA-DR if it reacts at a detectable level (within, for example, an ELISA assay) with HLA-DR, and does not react detectably with unrelated polypeptides under similar conditions.

Immunological binding, as used in this context, generally refers to the non-covalent interactions of the type that occur between an antibody and an antigen for which the antibody is specific. The strength, or affinity of antibody-HLA-DR binding interactions can be expressed in terms of the dissociation constant ($K_d$) of the interaction, wherein a smaller $K_d$ represents a greater affinity. Immunological binding properties of HLA-DR-specific antibodies can be quantified using methods well known in the art. One such method entails measuring the rates of HLA-DR-specific antibody/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of a ssociation and dissociation. The ratio of $K_{off}/K_{on}$ enables cancellation of all parameters not related to affinity, and is thus equal to the dissociation constant $K_d$. See, generally, Davies et al., *Annual Rev. Biochem.* 59:439-473 (1990). Anti-HLA-DR antibodies of the present invention specifically bind to HLA-DR proteins. By "specifically bind" herein is meant that the antibodies bind to HLA-DR polypeptides with a binding constant in the range of at least $10^6$-$10^9$ M, more commonly at least $10^7$-$10^9$ M.

An "antigen-binding site," or "binding portion" of an HLA-DR-specific antibody refers to the part of the antibody molecule that participates in HLA-DR binding. The antigen-binding site is formed by amino acid residues of the N-terminal variable ("V") regions of the heavy ("H") and light ("L") chains. Three highly divergent stretches within the V regions of the heavy and light chains are referred to as "hypervariable regions" or "complementarity determining regions (CDRs)" that are interposed between more conserved flanking stretches known as "framework regions," or "FRs".

Thus the term "FR" refers to amino acid sequences that are naturally found between and adjacent to CDRs in antibodies. In an HLA-DR-specific antibody molecule, the three CDRs of a light chain and the three CDRs of a heavy chain are disposed relative to each other in three dimensional space to form an HLA-DR-binding surface. The HLA-DR-binding surface is complementary to the three-dimensional surface of the bound HLA-DR.

"Functionally active" or "functional activity" for the purposes herein refers to HLA-DR-specific antibodies that retain the biologic and/or immunologic activities of the DN1921 and/or DN1924 anti-HLA-DR antibodies disclosed herein. The term "epitope" refers to the specific portion of an HLA-DR antigen that interacts with a complementarity determining region (CDR) of an HLA-DR-specific antibody.

HLA-DR-Specific Non-Human Monoclonal Antibodies

The present invention provides non-human monoclonal antibodies that bind to HLA-DR at one or more apoptotogenic domain thereby inducing apoptosis in an HLA-DR-expressing tumor cell, but not an HLA-DR-expressing normal cell, to which the antibody binds. Exemplified herein are the HLA-DR-specific murine monoclonal apoptotic antibodies designated DN1921 and DN1924. DN1921 is further characterized by an immunosuppressive activity while DN1924 exhibits a reduced immunosuppressive activity as compared to DN1921.

Without being limited to any theory of operation, it is believed that HLA-DR-specific monoclonal antibodies of the present invention are capable of achieving apoptotic activity by binding specifically to one or more apoptotogenic epitope on the first protein domain of the HLA-DR hetrodimer. It is further believed that immunosuppressive HLA-DR-specific monoclonal antibodies (exemplified herein by DN1921) are further capable of competing for antigen-binding and, hence, display of that antigen to helper T (Th) cells while non-immunosuppressive HLA-DR-specific monoclonal antibodies (exemplified herein by DN1924) have a reduced capacity to compete for antigen binding. Non-human monoclonal and non-human/human chimeric antibodies that bind specifically to the first domains of the class II MHC molecule, HLA-DR, were prepared as described herein. Class II molecules transduce signals that can modulate cell growth and the class II MHC HLA-DR-specific antibodies presented herein can induce apoptosis of cancer cells.

The human major histocompatibility complex (MHC) class II molecule-specific antibodies, designated DN1921, chimeric DN1921, DN1924, and chimeric DN1924, were found to induce apoptosis in tumor cells that express HLA-DR on their surface. The anti-cancer activities of these antibodies are highly selective in that they affect neither the viability nor the function of non-malignant HLA-DR positive cells.

In most instances, antibodies made to an epitope or fragment of the HLA-DR protein are capable of binding to the full-length protein while showing little or no cross-reactivity to other proteins. Within certain embodiments, the inventive antibodies are generated to the first domains of the HLA-DR molecule, which corresponds to amino acids 1 to 88 and 1 to 96 of the alpha and beta HLA-DR chain (SEQ ID NO: 49 and 50, respectively).

Non-human monoclonal antibodies exemplified herein are murine monoclonal antibodies designated DN1921 and DN1924 comprising the heavy and light chain variable domains of SEQ ID NO: 13 and 2 (DN1921) and SEQ ID NO: 35 and 24 (DN1924), respectively, operably fused to murine IgG$_1$ heavy and IgKappa light chain constant regions (SEQ ID NOs 53 and 55, respectively).

Thus, within certain aspects, the present invention provides non-human monoclonal HLA-DR-specific apoptotic antibodies. Non-human monoclonal antibodies of the present invention can be isolated from a variety of animal species including, but not limited to, non-human primate, sheep, pig, cow, horse, donkey, poultry, rabbit, mouse, rat, guinea pig, hamster, dog, and cat origin. HLA-DR-specific apoptotic non-human monoclonal antibodies are exemplified herein by (1) the immunosuppressive antibody DN1921 comprising the heavy and light chain variable domains presented in SEQ ID NO: 13 and SEQ ID NO: 2, respectively, which are encoded by the polynucleotides of SEQ ID NOs 46 and 45, respectively and (2) the non-immunosuppressive antibody DN1924 comprising the heavy and light chain variable domains presented in SEQ ID NO: 35 and SEQ ID NO: 24, respectively, which are encoded by the polynucleotides of SEQ ID NOs 48 and 47, respectively.

Each of the DN1921 and DN1924 antibodies exemplified herein further comprise a murine $IgG_1$ heavy and IgKappa light chain constant domain. Within related alternative embodiments, DN1921 and/or DN1924 monoclonal antibodies may comprise the aforementioned heavy and light chain variable domains and a murine heavy chain constant domain from an antibody isotype selected from the group consisting of IgM, IgD, $IgG_2$, $IgG_3$, $IgG_4$, IgE, $IgA_1$ and $IgA_2$.

Also provided are antigen-binding fragments, variants, and derivatives of DN1921 and DN1924 heavy and light chains. Within certain embodiments, variants of DN1921 comprise heavy and light chain variable domains that are at least 70% identical to SEQ ID NO: 13 and 2, respectively. Within other embodiments, variants of DN1921 comprise heavy and light chain variable domains that are at least 80%, 90%, or 95% identical to SEQ ID NO: 13 and 2, respectively. Within still further embodiments, variants of DN1921 comprise heavy and light chain variable domains that are at least 98% or 99% identical to SEQ ID NO: 13 and 2, respectively.

Within a lternative embodiments, variants of DN 1924 comprise heavy and light chain variable domains that are at least 70% identical to SEQ ID NO: 35 and 24, respectively. Within other embodiments, variants of DN1924 comprise heavy and light chain variable domains that are at least 80%, 90%, or 95% identical to SEQ ID NO: 35 and 24, respectively. Within still further embodiments, variants of DN1924 comprise heavy and light chain variable domains that are at least 98% or 99% identical to SEQ ID NO: 35 and 24, respectively.

Conventional methodologies may be employed for the production of monoclonal antibodies (mAbs) of the present invention. Generally rodents (usually mice) are repeatedly immunized with an HLA-DR antigen of interest, antibody-producing B cells are isolated from killed immunized animals, and the antibody-producing B cells are immortalized by fusion with myeloma cells to generate B cell "hybridomas." Libraries of hybridoma cells are screened for antigen-binding specificity and suitable clones purified and propagated. Monoclonal antibodies may be prepared using hybridoma methods, such as those previously described and readily available in the art. Kohler et al., *Nature* 256:495 (1975).

Immortal cell lines may be produced, for example, from spleen cells obtained from an animal immunized with the HLA-DR antigen as indicated above. Spleen cells are immortalized by, for example, fusing with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells.

The hybridoma cells may be cultured in a suitable culture medium that preferably contains one or more substances that inhibit the growth or survival of the unfused, immortalized cells. Exemplary immortalized cell lines are those that fuse efficiently, support stable high level expression of antibody by the selected antibody-producing cells, and are sensitive to a medium such as hypoxanthine, aminopterin, and thymidine ("HAT medium"). More exemplary immortalized cell lines are murine myeloma lines, which can be obtained, for instance, from the Salk Institute Cell Distribution Center, San Diego, Calif. and the American Type Culture Collection (ATCC), Rockville, Md. Human myeloma and mouse-human heteromyeloma cell lines also have been described for the production of human monoclonal antibodies. Kozbor, *J. Immunol.* 133:3001 (1984) and Brodeur et al., Monoclonal Antibody Production Techniques and Applications, pp. 51-63 (ed. Marcel Dekker, Inc., New York, 1987).

The culture medium in which the hybridoma cells are cultured can then be assayed for the presence of monoclonal antibodies directed against the HLA-DR polypeptide. The binding specificity of monoclonal antibodies produced by the hybridoma cells may be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson et al., *Anal. Biochem.* 107:220 (1980).

After the desired hybridoma cells are identified, the clones may be subcloned by limiting dilution procedures and grown by standard methods. Goding, "Monoclonal Antibodies: Principles and Practice," 59-103 (Academic Press, 1986). Suitable culture media for this purpose include, for example, Dulbecco's Modified Eagle's Medium and RPMI-1640 medium. Alternatively, the hybridoma cells may be grown in vivo as ascites in a mammal.

HLA-DR-specific monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. HLA-DR polypeptides (for example human HLA-DR alpha and beta polypeptides presented in SEQ ID NO: 49 and 50) of this invention may be used in the purification process in, for example, an affinity chromatography step. Alternatively, monoclonal antibodies secreted by the subclones may be isolated or purified from the culture medium or ascites fluid by conventional antibody purification procedures such as, for example, protein A-Sepharose, hydroxylapatite chromatography, gel electrophoresis, dialysis, or other affinity chromatography methodology.

Monoclonal antibodies may also be made by recombinant DNA methods, such as those described in U.S. Pat. No. 4,816, 567, incorporated herein by reference. DNA encoding the monoclonal antibodies of the invention can be readily isolated and sequenced using conventional procedures (e.g., by using oligonucleotide probes that are capable of binding specifically to genes encoding the heavy and light chains of murine antibodies).

Once isolated, the DNA may be cloned into expression vectors, which are then transfected into host cells such as simian COS cells, Chinese hamster ovary (CHO) cells, or myeloma cells that do not otherwise produce antibody protein, to obtain the synthesis of monoclonal antibodies in the recombinant host cells. The DNA also may be modified, for example, by substituting the coding sequence for human heavy and light chain constant domains in place of the homologous murine sequences or by covalently joining to the antibody coding sequence all or part of the coding sequence for a non-antibody polypeptide. Such a non-antibody polypeptide can be substituted for the constant domains of an antibody of the invention, or can be substituted for the variable domains of one antigen-combining site of an antibody of the invention to create a chimeric bivalent antibody as described in greater detail herein below.

Thus, within certain aspects, the present invention provides non-human monoclonal HLA-DR-specific apoptotic antibodies. Non-human monoclonal antibodies of the present invention can be isolated from a variety of animal species including, but not limited to, non-human primate, sheep, pig, cow, horse, donkey, poultry, rabbit, mouse, rat, guinea pig, hamster, dog, and cat origin. HLA-DR-specific apoptotic non-human monoclonal antibodies are exemplified herein by (1) the immunosuppressive antibody DN1921 comprising the heavy and light chain variable domains presented in SEQ ID NO: 13 and SEQ ID NO: 2, respectively, which are encoded by the polynucleotides of SEQ ID NOs 46 and 45, respectively and (2) the non-immunosuppressive antibody DN1924 comprising the heavy and ight chain variable domains presented in SEQ ID NO: 35 and SEQ ID NO: 24, respectively, which are encoded by the polynucleotides of SEQ ID NOs 48 and 47, respectively.

Each of the DN1921 and DN1924 antibodies exemplified herein further comprise a murine $IgG_1$ heavy and IgKappa light chain constant domain. Within related alternative embodiments, DN1921 and/or DN1924 monoclonal antibodies may comprise the aforementioned heavy and light chain variable domains and a murine heavy chain constant domain from an antibody isotype selected from the group consisting of IgM, IgD, $IgG_2$, $IgG_3$, $IgG_4$, IgE, $IgA_1$ and $IgA_2$.

Also provided are antigen-binding fragments, variants, and derivatives of DN1921 and DN1924 heavy and light chains. Within certain embodiments, variants of DN1921 comprise heavy and light chain variable domains that are at least 70% identical to SEQ ID NO: 13 and 2, respectively. Within other embodiments, variants of DN1921 comprise heavy and light chain variable domains that are at least 80%, 90%, or 95% identical to SEQ ID NO: 13 and 2, respectively. Within still further embodiments, variants of DN1921 comprise heavy and light chain variable domains that are at least 98% or 99% identical to SEQ ID NO: 13 and 2, respectively.

Within a lternative embodiments, variants of DN1924 comprise heavy and light chain variable domains that are at least 70% identical to SEQ ID NO: 35 and 24, respectively. Within other embodiments, variants of DN1924 comprise heavy and light chain variable domains that are at least 80%, 90%, or 95% identical to SEQ ID NO: 35 and 24, respectively. Within still further embodiments, variants of DN1924 comprise heavy and light chain variable domains that are at least 98% or 99% identical to SEQ ID NO: 35 and 24, respectively.

Chimeric Antibodies

Other aspects of the present invention provide non-human/human chimeric HLA-DR-specific monoclonal antibodies wherein the chimeric antibodies comprise a non-human variable domain operably fused to human constant domain. Non-human/human chimeric HLA-DR-specific monoclonal antibodies of the present invention induce apoptosis in HLA-DR expressing tumor cells, but not normal cells, to which the antibody is bound. Within certain embodiments, inventive non-human/human chimeric HLA-DR-specific apoptotic monoclonal antibodies are non-immunosuppressive when administered in vivo to a subject. Presented herein are non-human/human chimeric HLA-DR-specific antibodies exemplified by the murine/human chimeric DN1921 and murine/human chimeric DN1924 HLA-DR-specific monoclonal antibodies. The amino acid sequences of these chimeric antibodies and their constituent structural regions are presented in Table 1 (chimeric DN1921) and Table 2 (chimeric DN1924).

As used herein, the term "chimeric antibodies" refers to antibody molecules comprising heavy and light chains in which non-human antibody variable domains are operably fused to human constant domains. Chimeric antibodies generally exhibit reduced immunogenicity as compared to the parental fully-non-human antibody.

Methodologies for generating chimeric antibody molecules comprising non-human antigen-binding variable domains operably fused to human constant domains have been described in the art. See, for example, Winter et al., *Nature* 349:293-299 (1991); Lobuglio et al., *Proc. Nat. Acad. Sci. USA* 86:4220-4224 (1989); Shaw et al., *J. Immunol.* 138:4534-4538 (1987); Brown et al., *Cancer Res.* 47:3577-3583 (1987); U.S. Pat. No. 4,816,567 to Cabilly; Cabilly et al., *Proc. Natl. Acad. Sci. USA* 81:3273-3277 (1984); Morrison et al., *Proc. Natl. Acad. Sci. USA* 81:6851-6855 (1984); Boulianne et al., *Nature* 312:643-646 (1984); Cabilly et al., European Patent Application 125023 (published Nov. 14, 1984); Neuberger et al., *Nature* 314:268-270 (1985); Taniguchi et al., European Patent Application 171496 (published Feb. 19, 1985); Morrison et al., European Patent Application 1 73494 (published Mar. 5, 1 986); Neuberger et al., PCT Application WO 86/01533, (published Mar. 13, 1986); Kudo et al., European Patent Application 184187 (published Jun. 11, 1986); Morrison et al., European Patent Application 173494 (published Mar. 5, 1986); Sahagan et al., *J. Immunol.* 137:1066-1074 (1986); Robinson et al., International Patent Publication #PCT/US86/02269 (published May 7, 1987); Liu et al., *Proc. Natl. Acad. Sci. USA* 84:3439-3443 (1987); Sun et al., *Proc. Natl. Acad. Sci. USA* 84:214-218 (1987); Better et al., *Science* 240:1041-1043 (1988); and Harlow and Lane *Antibodies: a Laboratory Manual* Cold Spring Harbor Laboratory (1988)). Each of these references is incorporated herein by reference.

Chimeric antibodies include monovalent, divalent or polyvalent antibodies. A monovalent chimeric antibody is a dimer of heavy and light chains (HL) formed by a chimeric H chain associated through disulfide bridges with a chimeric L chain. A divalent chimeric antibody is tetramer ($H_2L_2$) formed by two HL dimers associated through at least one disulfide bridge. A polyvalent chimeric antibody can also be produced, for example, by employing a CH region that aggregates (e.g., from an IgM H chain, or µ chain).

Murine and chimeric antibodies, fragments and regions of the present invention comprise individual heavy and/or light antibody chains. A chimeric heavy chain comprises an antigen binding region derived from the heavy chain of a non-human antibody specific for HLA-DR, which is linked to at least a portion of a human heavy chain constant region.

A chimeric light chain according to the present invention, comprises an antigen binding region derived from the light chain of a non-human antibody specific for HLA-DR, linked to at least a portion of a human light chain constant region.

Antibodies, fragments or derivatives having chimeric heavy chains and light chains of the same or different variable region binding specificity, can also be prepared by appropriate association of the individual polypeptide chains, according to known method steps, e.g., according to Ausubel supra and Harlow supra.

Within certain embodiments, host cells expressing chimeric heavy chains (or their derivatives) may be separately cultured from hosts expressing chimeric light chains (or their derivatives), and the immunoglobulin chains are separately recovered and then associated. Alternatively, the host cells can be co-cultured and the chains allowed to associate spontaneously in the culture medium, followed by recovery of the assembled immunoglobulin, fragment or derivative.

As exemplified herein, antibody heavy and light chains may be transfected into the same cell and assembled by the cell as it is transported and secreted.

Hybrid cells can be formed by fusion of a non-human HLA-DR-specific antibody-producing cell, typically a spleen cell of an animal immunized against either natural or recombinant human HLA-DR, or a peptide fragment of a human HLA-DR protein sequence. Alternatively, the non-human HLA-DR-specific antibody-producing cell can be a B lymphocyte obtained from the blood, spleen, lymph nodes or other tissue of an animal immunized with HLA-DR.

The second fusion partner, which provides the immortalizing function, can be a lymphoblastoid cell or a plasmacytoma or myeloma cell, which is not itself an antibody producing cell, but is malignant. Exemplary fusion partner cells include the hybridoma SP2/0-Ag14 (SP2/0; ATCC CRL1581) and the myeloma P3X63Ag8 (ATCC TIB9), or its derivatives. See, e.g., Ausubel supra and Harlow supra.

Murine hybridomas that produce monoclonal antibodies specific for human HLA-DR are formed by fusion of a mouse fusion partner cell, such as SP2/0, and spleen cells from mice immunized against purified HLA-DR, recombinant HLA-DR, natural or synthetic HLA-DR peptides, including peptides comprising amino acids 1 to 88 and 1 to 96 of the alpha and beta HLA-DR chain (SEQ ID NO: 49 and 50, respectively).

To immunize the mice, a variety of different conventional protocols can be followed. For example, mice can receive primary and boosting immunizations of HLA-DR. The antibody-producing cell contributing the nucleotide sequences encoding the antigen-binding region of the chimeric antibody of the present invention can also be produced by transformation of a non-human, such as a primate, or a human cell. For example, a B lymphocyte that produces an HLA-DR-specific antibody can be infected and transformed with a virus such as Epstein-Barr virus to yield an immortal HLA-DR-specific producing cell. See, e.g., Kozbor et al., *Immunol. Today* 4:72-79 (1983). Alternatively, B lymphocyte can be transformed by providing a transforming gene or transforming gene product, as is well-known in the art. See, e.g., Ausubel supra and Harlow supra.

Non-human monoclonal antibody variable domains suitable for construction of chimeric monoclonal antibodies of the present invention can be isolated from a variety of animal species including, but not limited to, non-human primate, sheep, pig, cow, horse, donkey, poultry, rabbit, mouse, rat, guinea pig, hamster, dog, and cat origin. Human antibody heavy chain constant domains can be isolated from antibody isotypes selected from the group consisting of IgM, IgD, $IgG_1$, $IgG_2$, $IgG_3$, $IgG_4$, IgE, $IgA_1$ and $IgA_2$.

Exemplary HLA-DR-specific chimeric monoclonal antibodies disclosed herein comprise heavy and light chain variable domains of murine monoclonal antibody DN1921 (SEQ ID NO: 13 and 2, respectively) operably fused to human heavy and light chain constant domains (SEQ ID NO: 14 and 3, respectively). The chimeric DN1921 monoclonal antibody disclosed herein is capable of inducing apoptosis in a tumor cell expressing HLA-DR and is immunosuppressive when administered in vivo. The amino acid sequence of the exemplary full-length chimeric DN1921 monoclonal antibody heavy chain is presented herein as SEQ ID NO: 12. The amino acid sequence of the exemplary full-length chimeric DN1921 monoclonal antibody light chain is presented herein as SEQ ID NO: 1.

Also provided are variants of the chimeric DN1921 heavy and light chains of SEQ ID NO: 12 and 1, respectively. Within certain embodiments, variants of chimeric DN1921 heavy and light chains are at least 70% identical to SEQ ID NO: 12 and 1, respectively. Within other embodiments, variants of chimeric DN1921 heavy and light chains are at least 80%, 90%, or 95% identical to SEQ ID NO: 12 and 1, respectively. Within still further embodiments, variants of chimeric DN1921 heavy and light chains are at least 98% or 99% identical to SEQ ID NO: 12 and 1, respectively.

Alternative exemplary HLA-DR-specific chimeric monoclonal antibodies disclosed herein comprise heavy and light chain variable domains of murine monoclonal antibody DN1924 (SEQ ID NO: 35 and 24, respectively) operably fused to human heavy and light chain constant domains (SEQ ID NO: 36 and 25, respectively). The chimeric DN1924 monoclonal antibody disclosed herein is capable of inducing apoptosis in a tumor cell expressing HLA-DR and is non-immunosuppressive when administered in vivo. The amino acid sequence of the exemplary full-length chimeric DN1924 monoclonal antibody heavy chain is presented herein as SEQ ID NO: 34. The amino acid sequence of the exemplary full-length chimeric DN1924 monoclonal antibody light chain is presented herein as SEQ ID NO: 23.

Within alternative embodiments, variants of the chimeric DN1924 heavy and light chains of SEQ ID NO: 34 and 23, respectively. Within certain embodiments, variants of chimeric DN1924 heavy and light chains are at least 70% identical to SEQ ID NO: 34 and 23, respectively. Within other embodiments, variants of chimeric DN1924 heavy and light chains are at least 80%, 90%, or 95% identical to SEQ ID NO: 34 and 23, respectively. Within still further embodiments, variants of chimeric DN1924 heavy and light chains are at least 98% or 99% identical to SEQ ID NO: 34 and 23, respectively.

TABLE 1

Chimeric DN1921
(Murine Variable Domains/Human Constant Domains)

| Full-length Antibody Light Chain | SEQ ID NO: 1 | Met Glu Thr Gln Ser Gln Val Phe Leu Ser Leu<br>Leu Leu Trp Val Ser Gly Thr Cys Gly Asn Ile<br>Met Leu Thr Gln Ser Pro Ser Ser Leu Ala Val<br>Ser Ala Gly Glu Lys Val Thr Met Thr Cys Lys<br>Ser Ser Gln Asp Ile Phe Tyr Ser Ser Asp Gln<br>Arg Asn Tyr Leu Ala Trp Tyr Gln Gln Arg Pro<br>Gly His Ser Pro Lys Leu Leu Ile Tyr Trp Ala |

TABLE 1-continued

Chimeric DN1921
(Murine Variable Domains/Human Constant Domains)

|  |  |  |
|---|---|---|
|  |  | Ser Thr Arg Glu Ser Gly Val Pro Asp Arg Phe<br>Thr Gly Ser Gly Ser Gly Thr Asp Phe Thr Leu<br>Thr Ile Ser Asn Val His Pro Glu Asp Leu Ala<br>Val Tyr Tyr Cys His Gln Tyr Leu Ser Ser Tyr<br>Thr Phe Gly Gly Gly Thr Lys Leu Glu Ile Arg<br>Thr Val Ala Ala Pro Ser Val Phe Ile Phe Pro<br>Pro Ser Asp Glu Gln Leu Lys Ser Gly Thr Ala<br>Ser Val Val Cys Leu Leu Asn Asn Phe Tyr Pro<br>Arg Glu Ala Lys Val Gln Trp Lys Val Asp Asn<br>Ala Leu Gln Ser Gly Asn Ser Gln Glu Ser Val<br>Thr Glu Gln Asp Ser Lys Asp Ser Thr Tyr Ser<br>Leu Ser Ser Thr Leu Thr Leu Ser Lys Ala Asp<br>Tyr Glu Lys His Lys Val Tyr Ala Cys Glu Val<br>Thr His Gln Gly Leu Ser Ser Pro Val Thr Lys<br>Ser Phe Asn Arg Gly Glu Cys |
| Light Chain<br>Variable Region | SEQ ID NO: 2 | Met Glu Thr Gln Ser Gln Val Phe Leu Ser Leu<br>Leu Leu Trp Val Ser Gly Thr Cys Gly Asn Ile<br>Met Leu Thr Gln Ser Pro Ser Ser Leu Ala Val<br>Ser Ala Gly Glu Lys Val Thr Met Thr Cys Lys<br>Ser Ser Gln Asp Ile Phe Tyr Ser Ser Asp Gln<br>Arg Asn Tyr Leu Ala Trp Tyr Gln Gln Arg Pro<br>Gly His Ser Pro Lys Leu Leu Ile Tyr Trp Ala<br>Ser Thr Arg Glu Ser Gly Val Pro Asp Arg Phe<br>Thr Gly Ser Gly Ser Gly Thr Asp Phe Thr Leu<br>Thr Ile Ser Asn Val His Pro Glu Asp Leu Ala<br>Val Tyr Tyr Cys His Gln Tyr Leu Ser Ser Tyr<br>Thr Phe Gly Gly Gly Thr Lys Leu Glu Ile Arg |
| Light Chain<br>Constant<br>Region (Human<br>Ig Kappa) | SEQ ID NO: 3 | Thr Val Ala Ala Pro Ser Val Phe Ile Phe Pro<br>Pro Ser Asp Glu Gln Leu Lys Ser Gly Thr Ala<br>Ser Val Val Cys Leu Leu Asn Asn Phe Tyr Pro<br>Arg Glu Ala Lys Val Gln Trp Lys Val Asp Asn<br>Ala Leu Gln Ser Gly Asn Ser Gln Glu Ser Val<br>Thr Glu Gln Asp Ser Lys Asp Ser Thr Tyr Ser<br>Leu Ser Ser Thr Leu Thr Leu Ser Lys Ala Asp<br>Tyr Glu Lys His Lys Val Tyr Ala Cys Glu Val<br>Thr His Gln Gly Leu Ser Ser Pro Val Thr Lys<br>Ser Phe Asn Arg Gly Glu Cys |
| Light Chain<br>Leader<br>Sequence | SEQ ID NO: 4 | Met Glu Thr Gln Ser Gln Val Phe Leu Ser Leu<br>Leu Leu Trp Val Ser Gly Thr Cys Gly |
| Light Chain<br>Framework<br>Region 1 (FR1) | SEQ ID NO: 5 | Asn Ile Met Leu Thr Gln Ser Pro Ser Ser Leu<br>Ala Val Ser Ala Gly Glu Lys Val Thr Met Thr<br>Cys Lys Ser Ser |
| Light Chain<br>Complementarity<br>Determining<br>Region 1<br>(CDR 1) | SEQ ID NO: 6 | Gln Asp Ile Phe Tyr Ser Ser Asp Gln Arg Asn<br>Tyr |
| Light Chain<br>Framework<br>Region 2 (FR2) | SEQ ID NO: 7 | Leu Ala Trp Tyr Gln Gln Arg Pro Gly His Ser<br>Pro Lys Leu Leu Ile Tyr |
| Light Chain<br>Complementarity<br>Determining<br>Region 2<br>(CDR2) | SEQ ID NO: 8 | Trp Ala Ser |
| Light Chain<br>Framework<br>Region 3 (FR3) | SEQ ID NO: 9 | Thr Arg Glu Ser Gly Val Pro Asp Arg Phe Thr<br>Gly Ser Gly Ser Gly Thr Asp Phe Thr Leu Thr<br>Ile Ser Asn Val His Pro Glu Asp Leu Ala Val<br>Tyr Tyr Cys |
| Light Chain<br>Complementarity<br>Determining<br>Region 3<br>(CDR3) | SEQ ID NO: 10 | His Gln Tyr Leu Ser Ser Tyr Thr |

TABLE 1-continued

Chimeric DN1921
(Murine Variable Domains/Human Constant Domains)

| | | |
|---|---|---|
| Light Chain Framework Region 4 (FR4) | SEQ ID NO: 11 | Phe Gly Gly Gly Thr Lys Leu Glu Ile Arg |
| Full-length Antibody Heavy Chain | SEQ ID NO: 12 | Met Val Leu Ser Leu Leu Tyr Leu Leu Thr<br>Ala Leu Pro Gly Ile Leu Ser Glu Val Gln Leu<br>Gln Glu Ser Gly Pro Ser Leu Met Lys Pro Ser<br>Gln Thr Leu Ser Leu Thr Cys Ser Val Thr Gly<br>Asp Ser Ile Thr Ser Gly Tyr Trp Asn Trp Ile<br>Arg Gln Phe Pro Gly Lys Lys Leu Glu Tyr Leu<br>Gly Tyr Val Ser Phe Thr Thr Ser Thr Tyr Tyr<br>Asn Pro Ser Leu Lys Ser Arg Ile Ser Ile Ala<br>Arg Asp Thr Ser Lys Asn Gln Phe Tyr Leu His<br>Leu Asn Ser Val Thr Ala Ala Asp Thr Ala Thr<br>Tyr Tyr Cys Ala Arg Leu Gly Gly Leu Leu Pro<br>Phe Gly Ala Met Asp Tyr Trp Ser Gln Gly Phe<br>Ser Val Thr Val Ser Ser Ala Ser Thr Lys<br>Gly Pro Ser Val Phe Pro Leu Ala Pro Cys Ser<br>Arg Ser Thr Ser Glu Ser Thr Ala Ala Leu Gly<br>Cys Leu Val Lys Asp Tyr Phe Pro Glu Pro Val<br>Thr Val Ser Trp Asn Ser Gly Ala Leu Thr Ser<br>Gly Val His Thr Phe Pro Ala Val Leu Gln Ser<br>Ser Gly Leu Tyr Ser Leu Ser Ser Val Val Thr<br>Val Thr Ser Ser Asn Phe Gly Thr Gln Thr Tyr<br>Thr Cys Asn Val Asp His Lys Pro Ser Asn Thr<br>Lys Val Asp Lys Thr Val Glu Arg Lys Cys Cys<br>Val Glu Cys Pro Pro Cys Pro Ala Pro Pro Ala<br>Ala Ala Pro Ser Val Phe Leu Phe Pro Pro Lys<br>Pro Lys Asp Thr Leu Met Ile Ser Arg Thr Pro<br>Glu Val Thr Cys Val Val Val Asp Val Ser His<br>Glu Asp Pro Glu Val Gln Phe Asn Trp Tyr Val<br>Asp Gly Met Glu Val His Asn Ala Lys Thr Lys<br>Pro Arg Glu Glu Gln Phe Asn Ser Thr Phe Arg<br>Val Val Ser Val Leu Thr Val His Gln Asp<br>Trp Leu Asn Gly Lys Glu Tyr Lys Cys Lys Val<br>Ser Asn Lys Gly Leu Pro Ala Pro Ile Glu Lys<br>Thr Ile Ser Lys Thr Lys Gly Gln Pro Arg Glu<br>Pro Gln Val Tyr Thr Leu Pro Pro Ser Arg Glu<br>Glu Met Thr Lys Asn Gln Val Ser Leu Thr Cys<br>Leu Val Lys Gly Phe Tyr Pro Ser Asp Ile Ala<br>Val Glu Trp Glu Ser Asn Gly Gln Pro Glu Asn<br>Asn Tyr Lys Thr Thr Pro Pro Met Leu Asp Ser<br>Asp Gly Ser Phe Phe Leu Tyr Ser Lys Leu Thr<br>Val Asp Lys Ser Arg Trp Gln Gln Gly Asn Val<br>Phe Ser Cys Ser Val Met His Glu Ala Leu His<br>Asn His Tyr Thr Gln Lys Her Leu Her Leu Ser<br>Pro Gly Lys |
| Heavy Chain Variable Region | SEQ ID NO: 13 | Met Val Leu Her Leu Leu Tyr Leu Leu Thr<br>Ala Leu Pro Gly Ile Leu Ser Glu Val Gln Leu<br>Gln Glu Her Gly Pro Ser Leu Met Lys Pro Ser<br>Gln Thr Leu Her Leu Thr Cys Ser Val Thr Gly<br>Asp Ser Ile Thr Ser Gly Tyr Trp Asn Trp Ile<br>Arg Gln Phe Pro Gly Lys Lys Leu Glu Tyr Leu<br>Gly Tyr Val Her Phe Thr Thr Ser Thr Tyr Tyr<br>Asn Pro Ser Leu Lys Ser Arg Ile Ser Ile Ala<br>Arg Asp Thr Ser Lys Asn Gln Phe Tyr Leu His<br>Leu Asn Ser Val Thr Aia Ala Asp Thr Ala Thr<br>Tyr Tyr Cys Ala Arg Leu Gly Gly Leu Leu Pro<br>Phe Gly Ala Met Asp Tyr Trp Her Gln Gly Phe<br>Her Val Thr Val Ser Her Ala |
| Heavy Chain Constant Region (Human IgG$_2$) | SEQ ID NO: 14 | Ala Her Thr Lys Gly Pro Her Val Phe Pro Leu<br>Ala Pro Cys Her Arg Her Thr Her Glu Her Thr<br>Ala Ala Leu Gly Cys Leu Val Lys Asp Tyr Phe<br>Pro Glu Pro Val Thr Val Her Trp Asn Her Gly<br>Ala Leu Thr Her Gly Val His Thr Phe Pro Ala<br>Val Leu Gln Ser Her Gly Leu Tyr Her Leu Her<br>Her Val Val Thr Val Thr Her Her Asn Phe Gly<br>Thr Gln Thr Tyr Thr Cys Asn Val Asp His Lys<br>Pro Her Asn Thr Lys Val Asp Lys Thr Val Glu<br>Arg Lys Cys Cys Val Glu Cys Pro Pro Cys Pro<br>Ala Pro Pro Ala Ala Ala Pro Her Val Phe Leu<br>Phe Pro Pro Lys Pro Lys Asp Thr Leu Met Ile<br>Her Arg Thr Pro Glu Val Thr Cys Val Val Val<br>Asp Val Her His Glu Asp Pro Glu Val Gln Phe |

TABLE 1-continued

Chimeric DN1921
(Murine Variable Domains/Human Constant Domains)

|  |  |  |
|---|---|---|
|  |  | Asn Trp Tyr Val Asp Gly Met Glu Val His Asn<br>Ala Lys Thr Lys Pro Arg Glu Glu Gln Phe Asn<br>Her Thr Phe Arg Val Val Her Val Leu Thr Val<br>Val His Gln Asp Trp Leu Asn Gly Lys Glu Tyr<br>Lys Cys Lys Val Her Asn Lys Gly Leu Pro Ala<br>Pro Ile Glu Lys Thr Ile Her Lys Thr Lys Gly<br>Gln Pro Arg Glu Pro Gln Val Tyr Thr Leu Pro<br>Pro Ser Arg Glu Glu Met Thr Lys Asn Gln Val<br>Her Leu Thr Cys Leu Val Lys Gly Phe Tyr Pro<br>Her Asp Ile Ala Val Glu Trp Glu Her Asn Gly<br>Gln Pro Glu Asn Asn Tyr Lys Thr Thr Pro Pro<br>Met Leu Asp Her Asp Gly Her Phe Phe Leu Tyr<br>Her Lys Leu Thr Val Asp Lys Her Arg Trp Gln<br>Gln Gly Asn Val Phe Her Cys Her Val Met His<br>Glu Ala Leu His Asn His Tyr Thr Gln Lys Her<br>Leu Her Leu Her Pro Gly Lys |
| Heavy Chain<br>Leader<br>Sequence | SEQ ID NO: 15 | Met Val Leu Her Leu Leu Tyr Leu Leu Thr Ala<br>Leu Pro Gly Ile Leu Her |
| Heavy Chain<br>Framework<br>Region 1 (FR1) | SEQ ID NO: 16 | Glu Val Gln Leu Gln Glu Her Gly Pro Her Leu<br>Met Lys Pro Ser Gln Thr Leu Ser Leu Thr Cys<br>Her Val Thr |
| Heavy Chain<br>Complementarity<br>Determining<br>Region 1<br>(CDR1) | SEQ ID NO: 17 | Gly Asp Her Ile Thr Her Gly Tyr |
| Heavy Chain<br>Framework<br>Region 2 (FR2) | SEQ ID NO: 18 | Trp Asn Trp Ile Arg Gln Phe Pro Gly Lys Lys<br>Leu Glu Tyr Leu Gly Tyr |
| Heavy Chain<br>Complementarity<br>Determining<br>Region 2<br>(CDR2) | SEQ ID NO: 19 | Val Her Phe Thr Thr Her Thr |
| Heavy Chain<br>Framework<br>Region 3 (FR3) | SEQ ID NO: 20 | Tyr Tyr Asn Pro Ser Leu Lys Ser Arg Ile Ser<br>Ile Ala Arg Asp Thr Ser Lys Asn Gln Phe Tyr<br>Leu His Leu Asn Ser Val Thr Ala Ala Asp Thr<br>Ala Thr Tyr Tyr Cys |
| Heavy Chain<br>Complementarity<br>Determining<br>Region 3<br>(CDR3) | SEQ ID NO: 21 | Ala Arg Leu Gly Gly Leu Leu Pro Phe Gly Ala<br>Met Asp Tyr |
| Heavy Chain<br>Framework<br>Region 4 (FR4) | SEQ ID NO: 22 | Trp Ser Gln Gly Phe Ser Val Thr Val Ser Ser<br>Ala |

TABLE 2

Chimeric DN1924
(Murine Variable Domains/Human Constant Domains)

|  |  |  |
|---|---|---|
| Full-length<br>Antibody Light<br>Chain | SEQ ID NO: 23 | Met Phe Ser Leu Ala Leu Leu Ser Leu Leu<br>Leu Leu Cys Val Ser Asp Ser Arg Ala Glu Thr<br>Thr Val Thr Gln Ser Pro Ala Ser Leu Ser Met<br>Ala Ile Gly Glu Lys Val Thr Ile Arg Cys Ile<br>Thr Ser Thr Asp Ile Asp Asp Asp Met Asn Trp<br>Tyr Gln Gln Lys Pro Gly Glu Pro Pro Lys Leu<br>Leu Ile Ser Glu Gly Asn Thr Leu Arg Pro Gly<br>Val Pro Ser Arg Phe Ser Ser Ser Gly Tyr Gly<br>Thr Asp Phe Val Phe Thr Ile Glu Asn Met Leu<br>Ser Glu Asp Val Ala Asp Tyr Tyr Leu Gln Ser<br>Asp Asn Leu Pro Tyr Thr Phe Gly Gly Gly Thr<br>Lys Leu Glu Ile Lys Thr Val Aia Ala Pro Ser<br>Val Phe Ile Phe Pro Pro Ser Asp Glu Gln Leu |

TABLE 2-continued

Chimeric DN1924
(Murine Variable Domains/Human Constant Domains)

|  |  |  |
|---|---|---|
|  |  | Lys Ser Gly Thr Aia Ser Val Val Cys Leu Leu<br>Asn Asn Phe Tyr Pro Arg Glu Aia Lys Val Gln<br>Trp Lys Val Asp Asn Aia Leu Gln Ser Gly Asn<br>Ser Gln Glu Ser Val Thr Glu Gln Asp Ser Lys<br>Asp Ser Thr Tyr Ser Leu Ser Ser Thr Leu Thr<br>Leu Ser Lys Aia Asp Tyr Glu Lys His Lys Val<br>Tyr Ala Cys Glu Val Thr His Gln Gly Leu Ser<br>Ser Pro Val Thr Lys Ser Phe Asn Arg Gly Glu<br>Cys |
| Light Chain<br>Variable Region | SEQ ID NO: 24 | Met Phe Ser Leu Ala Leu Leu Leu Ser Leu Leu<br>Leu Leu Cys Val Ser Asp Ser Arg Ala Glu Thr<br>Thr Val Thr Gln Ser Pro Ala Ser Leu Ser Met<br>Aia Ile Gly Glu Lys Val Thr Ile Arg Cys Ile<br>Thr Ser Thr Asp Ile Asp Asp Asp Met Asn Trp<br>Tyr Gln Gln Lys Pro Gly Glu Pro Pro Lys Leu<br>Leu Ile Ser Glu Gly Asn Thr Leu Arg Pro Gly<br>Val Pro Ser Arg Phe Ser Ser Ser Gly Tyr Gly<br>Thr Asp Phe Val Phe Thr Ile Glu Asn Met Leu<br>Ser Glu Asp Val Ala Asp Tyr Tyr Leu Gln Ser<br>Asp Asn Leu Pro Tyr Thr Phe Gly Gly Gly Thr<br>Lys Leu Glu Ile Lys |
| Light Chain<br>Constant<br>Region (Human<br>Ig Kappa) | SEQ ID NO: 25 | Thr Val Ala Ala Pro Ser Val Phe Ile Phe Pro<br>Pro Ser Asp Glu Gln Leu Lys Ser Gly Thr Ala<br>Ser Val Val Cys Leu Leu Asn Asn Phe Tyr Pro<br>Arg Glu Ala Lys Val Gln Trp Lys Val Asp Asn<br>Ala Leu Gln Ser Gly Asn Ser Gln Glu Ser Val<br>Thr Glu Gln Asp Ser Lys Asp Ser Thr Tyr Ser<br>Leu Ser Ser Thr Leu Thr Leu Ser Lys Ala Asp<br>Tyr Glu Lys His Lys Val Tyr Ala Cys Glu Val<br>Thr His Gln Gly Leu Ser Ser Pro Val Thr Lys<br>Ser Phe Asn Arg Gly Glu Cys |
| Light Chain<br>Leader<br>Sequence | SEQ ID NO: 26 | Met Phe Ser Leu Ala Leu Leu Leu Ser Leu Leu<br>Leu Leu Cys Val Ser Asp Ser Arg Ala |
| Light Chain<br>Framework<br>Region 1 (FR1) | SEQ ID NO: 27 | Glu Thr Thr Val Thr Gln Ser Pro Ala Ser Leu<br>Ser Met Ala Ile Gly Glu Lys Val Thr Ile Arg<br>Cys Ile Thr Ser |
| Light Chain<br>Complementarity<br>Determining<br>Region 1<br>(CDR1) | SEQ ID NO: 28 | Thr Asp Ile Asp Asp Asp |
| Light Chain<br>Framework<br>Region 2 (FR2) | SEQ ID NO: 29 | Met Asn Trp Tyr Gln Gln Lys Pro Gly Glu Pro<br>Pro Lys Leu Leu Ile Ser |
| Light Chain<br>Complementarity<br>Determining<br>Region 2<br>(CDR2) | SEQ ID NO: 30 | Glu Gly Asn |
| Light Chain<br>Framework<br>Region 3 (FR3) | SEQ ID NO: 31 | Thr Leu Arg Pro Gly Val Pro Ser Arg Phe Ser<br>Ser Ser Gly Tyr Gly Thr Asp Phe Val Phe Thr<br>Ile Glu Asn Met Leu Ser Glu Asp Val Ala Asp<br>Tyr Tyr |
| Light Chain<br>Complementarity<br>Determining<br>Region 3<br>(CDR3) | SEQ ID NO: 32 | Leu Gln Ser Asp Asn Leu Pro Tyr Thr |
| Light Chain<br>Framework<br>Region 4 (FR4) | SEQ ID NO: 33 | Phe Gly Gly Gly Thr Lys Leu Glu Ile Lys |
| Full-length<br>Antibody Heavy<br>Chain | SEQ ID NO: 34 | Met Asp Phe Gly Leu Ile Phe Phe Ile Val Ala<br>Leu Leu Lys Gly Val Gln Cys Glu Val Lys Leu<br>Leu Glu Ser Gly Gly Gly Leu Val Gln Pro Gly<br>Gly Ser Leu Lys Leu Ser Cys Ala Ala Ser Gly |

TABLE 2-continued

Chimeric DN1924
(Murine Variable Domains/Human Constant Domains)

|  |  |  |
|---|---|---|
|  |  | Phe Asp Phe Ser Arg Tyr Trp Met Ser Trp Val<br>Arg Gln Ala Pro Gly Lys Gly Leu Glu Trp Ile<br>Gly Glu Ile Asn Pro Asp Ser Ser Thr Ile Asn<br>Tyr Thr Pro Ser Leu Lys Asp Lys Phe Ile Ile<br>Ser Arg Asp Asn Ala Lys Asn Thr Leu Tyr Leu<br>Gln Met Ser Lys Val Arg Ser Glu Asp Thr Ala<br>Leu Tyr Tyr Cys Ala Arg Gln Pro Tyr Tyr Tyr<br>Gly Ser Ser Tyr Trp Tyr Phe Asp Val Trp Gly<br>Ala Gly Thr Thr Val Thr Val Ser Ser Ala Ala<br>Ser Thr Lys Gly Pro Ser Val Phe Pro Leu Ala<br>Pro Cys Ser Arg Ser Thr Ser Glu Ser Thr Ala<br>Ala Leu Gly Cys Leu Val Lys Asp Tyr Phe Pro<br>Glu Pro Val Thr Val Ser Trp Asn Ser Gly Ala<br>Leu Thr Ser Gly Val His Thr Phe Pro Ala Val<br>Leu Gln Ser Ser Gly Leu Tyr Ser Leu Ser Ser<br>Val Val Thr Val Thr Ser Ser Asn Phe Gly Thr<br>Gln Thr Tyr Thr Cys Asn Val Asp His Lys Pro<br>Ser Asn Thr Lys Val Asp Lys Thr Val Glu Arg<br>Lys Cys Cys Val Glu Cys Pro Pro Cys Pro Ala<br>Pro Pro Ala Ala Ala Pro Ser Val Phe Leu Phe<br>Pro Pro Lys Pro Lys Asp Thr Leu Met Ile Ser<br>Arg Thr Pro Glu Val Thr Cys Val Val Val Asp<br>Val Ser His Glu Asp Pro Glu Val Gln Phe Asn<br>Trp Tyr Val Asp Gly Met Glu Val His Asn Ala<br>Lys Thr Lys Pro Arg Glu Glu Gln Phe Asn Ser<br>Thr Phe Arg Val Val Ser Val Leu Thr Val Val<br>His Gln Asp Trp Leu Asn Gly Lys Glu Tyr Lys<br>Cys Lys Val Ser Asn Lys Gly Leu Pro Ala Pro<br>Ile Glu Lys Thr Ile Ser Lys Thr Lys Gly Gln<br>Pro Arg Glu Pro Gln Val Tyr Thr Leu Pro Pro<br>Ser Arg Glu Glu Met Thr Lys Asn Gln Val Ser<br>Leu Thr Cys Leu Val Lys Gly Phe Tyr Pro Ser<br>Asp Ile Ala Val Glu Trp Glu Ser Asn Gly Gln<br>Pro Glu Asn Asn Tyr Lys Thr Thr Pro Pro Met<br>Leu Asp Ser Asp Gly Ser Phe Phe Leu Tyr Ser<br>Lys Leu Thr Val Asp Lys Ser Arg Trp Gln Gln<br>Gly Asn Val Phe Ser Cys Ser Val Met His Glu<br>Ala Leu His Asn His Tyr Thr Gln Lys Ser Leu<br>Ser Leu Ser Pro Gly Lys |
| Heavy Chain<br>Variable Region | SEQ ID NO: 35 | Met Asp Phe Gly Leu Ile Phe Phe Ile Val Ala<br>Leu Leu Lys Gly Val Gln Cys Glu Val Lys Leu<br>Leu Glu Ser Gly Gly Gly Leu Val Gln Pro Gly<br>Gly Ser Leu Lys Leu Ser Cys Ala Ala Ser Gly<br>Phe Asp Phe Ser Arg Tyr Trp Met Ser Trp Val<br>Arg Gln Ala Pro Gly Lys Gly Leu Glu Trp Ile<br>Gly Glu Ile Asn Pro Asp Ser Ser Thr Ile Asn<br>Tyr Thr Pro Ser Leu Lys Asp Lys Phe Ile Ile<br>Ser Arg Asp Asn Ala Lys Asn Thr Leu Tyr Leu<br>Gln Met Ser Lys Val Arg Ser Glu Asp Thr Ala<br>Leu Tyr Tyr Cys Ala Arg Gln Pro Tyr Tyr Tyr<br>Gly Ser Ser Tyr Trp Tyr Phe Asp Val Trp Gly<br>Ala Gly Thr Thr Val Thr Val Ser Ser Ala |
| Heavy Chain<br>Constant<br>Region (Human<br>IgG$_2$) | SEQ ID NO: 36 | Ala Ser Thr Lys Gly Pro Ser Val Phe Pro Leu<br>Ala Pro Cys Ser Arg Ser Thr Ser Glu Ser Thr<br>Ala Ala Leu Gly Cys Leu Val Lys Asp Tyr Phe<br>Pro Glu Pro Val Thr Val Ser Trp Asn Ser Gly<br>Ala Leu Thr Ser Gly Val His Thr Phe Pro Ala<br>Val Leu Gln Ser Ser Gly Leu Tyr Ser Leu Ser<br>Ser Val Val Thr Val Thr Ser Ser Asn Phe Gly<br>Thr Gln Thr Tyr Thr Cys Asn Val Asp His Lys<br>Pro Ser Asn Thr Lys Val Asp Lys Thr Val Glu<br>Arg Lys Cys Cys Val Glu Cys Pro Pro Cys Pro<br>Ala Pro Pro Ala Ala Ala Pro Ser Val Phe Leu<br>Phe Pro Pro Lys Pro Lys Asp Thr Leu Met Ile<br>Ser Arg Thr Pro Glu Val Thr Cys Val Val Val<br>Asp Val Ser His Glu Asp Pro Glu Val Gln Phe<br>Asn Trp Tyr Val Asp Gly Met Glu Val His Asn<br>Ala Lys Thr Lys Pro Arg Glu Glu Gln Phe Asn<br>Ser Thr Phe Arg Val Val Ser Val Leu Thr Val<br>Val His Gln Asp Trp Leu Asn Gly Lys Glu Tyr<br>Lys Cys Lys Val Ser Asn Lys Gly Leu Pro Ala<br>Pro Ile Glu Lys Thr Ile Ser Lys Thr Lys Gly<br>Gln Pro Arg Glu Pro Gln Val Tyr Thr Leu Pro<br>Pro Ser Arg Glu Glu Met Thr Lys Asn Gln Val<br>Ser Leu Thr Cys Leu Val Lys Gly Phe Tyr Pro |

TABLE 2-continued

Chimeric DN1924
(Murine Variable Domains/Human Constant Domains)

|  |  |  |
|---|---|---|
|  |  | Ser Asp Ile Ala Val Glu Trp Glu Ser Asn Gly<br>Gln Pro Glu Asn Asn Tyr Lys Thr Thr Pro Pro<br>Met Leu Asp Ser Asp Gly Ser Phe Phe Leu Tyr<br>Ser Lys Leu Thr Val Asp Lys Ser Arg Trp Gln<br>Gln Gly Asn Val Phe Ser Cys Ser Val Met His<br>Glu Ala Leu His Asn His Tyr Thr Gln Lys Ser<br>Leu Ser Leu Ser Pro Gly Lys |
| Heavy Chain Leader Sequence | SEQ ID NO: 37 | Met Asp Phe Gly Leu Ile Phe Phe Ile Val Ala Leu Leu Lys Gly Val Gln Cys |
| Heavy Chain Framework Region 1 (FR1) | SEQ ID NO: 38 | Glu Val Lys Leu Leu Glu Ser Gly Gly Gly Leu Val Gln Pro Gly Gly Ser Leu Lys Leu Ser Cys Ala Ala Ser |
| Heavy Chain Complementarity Determining Region 1 (CDR1) | SEQ ID NO: 39 | Gly Phe Asp Phe Ser Arg Tyr Trp |
| Heavy Chain Framework Region 2 (FR2) | SEQ ID NO: 40 | Met Ser Trp Val Arg Gln Ala Pro Gly Lys Gly Leu Glu Trp Ile Gly Glu |
| Heavy Chain Complementarity Determining Region 2 (CDR2) | SEQ ID NO: 41 | Ile Asn Pro Asp Ser Ser Thr Ile |
| Heavy Chain Framework Region 3 (FR3) | SEQ ID NO: 42 | Asn Tyr Thr Pro Ser Leu Lys Asp Lys Phe Ile Ile Ser Arg Asp Asn Ala Lys Asn Thr Leu Tyr Leu Gln Met Ser Lys Val Arg Ser Glu Asp Thr Ala Leu Tyr Tyr Cys |
| Heavy Chain Complementarity Determining Region 3 (CDR3) | SEQ ID NO: 43 | Ala Arg Gln Pro Tyr Tyr Tyr Gly Ser Ser Tyr Trp Tyr Phe Asp Val |
| Heavy Chain Framework Region 4 (FR4) | SEQ ID NO: 44 | Trp Gly Ala Gly Thr Thr Val Thr Val Ser Ser Ala |

Humanized Antibodies

Within still fuirther embodiments, the present invention provides humanized HLA-DR-specific apoptotic monoclonal antibodies wherein the humanized antibody comprises one or more non-human complementarity determining region (CDR), a human variable domain framework region (FR), and a human heavy chain constant domain, such as the $IgG_2$ heavy chain constant domain and human light chain constant domain, such as the IgKappa light chain constant domain. Generally, "humanized" HLA-DR-specific antibodies are useful in minimizing unwanted immunological response toward the corresponding non-human (e.g., rodent) antibody or non-human regions thereof that otherwise limit the duration and effectiveness of therapeutic applications of those moieties in human recipients. Jones et al., Nature 321:522-525 (1986); Reichmann et al., Nature 332:323-327 (1988); and Verhoeyen et al., Science 239:1534-1536 (1988).

As used herein, the term "humanized antibody" is meant to include human antibodies (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, variable domain framework residues of the human antibody are replaced by corresponding non-human residues. Humanized antibodies may also comprise residues that are found neither in the recipient antibody nor in the imported CDR or framework sequences.

In general, the humanized antibody will comprise substantially all of at least one, and typically two, variable domains, in which all or substantially all of the CDR regions correspond to those of a non-human antibody and all or substantially all of the FR regions are those of a human antibody consensus sequence. The humanized antibody optimally also will comprise at least a portion of an antibody constant region, typically that of a human antibody.

Humanized monoclonal antibodies are typically approximately 90-95% human with only the complementarity determining regions (CDRs) being non-human. Generally, humanized monoclonal antibodies produced in rodent cells are less immunogenic than the corresponding chimeric monoclonal antibodies from which they derive. Bell et al., Lancet 355: 858-859 (2000).

As indicated above, the term "complementarity determining region" (CDR) refers to the hypervariable region of an antibody molecule that forms a surface complementary to the 3-dimensional surface of a bound antigen. Proceeding from N-terminus to C-terminus, each antibody heavy and light chain is comprised of three CDRs (CDR 1, CDR 2, and CDR3). An HLA-DR antigen-binding site, therefore, includes a total of six CDRs, comprising the three CDRs from each of a heavy and a light chain V region. The amino acid residues of CDRs form extensive contact with bound antigen, wherein the most extensive antigen contact is with the heavy chain CDR3.

Humanized HLA-DR-specific apoptotic antibodies comprise one or more non-human complementarity determining region (CDR) operably fused to a human variable domain framework region (FR) to create heavy and light chain variable domains, which are operably fused to human constant domain heavy and light chains, exemplified herein by the heavy chain $IgG_2$ and light chain IgKappa constant domains presented in SEQ ID NO: 14 and 3, respectively.

Exemplary HLA-DR-specific humanized monoclonal antibodies of the present invention comprise one or more complementarity determining region (CDR) of murine monoclonal antibody DN1921 heavy chain variable domain (SEQ ID NO: 13) operably fused to human heavy chain framework (FR) domains to create a humanized HLA-DR-specific heavy chain variable domain that is, optionally, operably fused to a human heavy chain constant domain wherein the constant domain is selected from the group consisting of IgM, IgD, $IgG_1$, $IgG_2$, $IgG_3$, $IgG_4$, IgE, $IgA_1$ and $IgA_2$ exemplified herein by the human $IgG_2$ heavy chain constant domain presented in SEQ ID NO: 14.

Alternatively or additionally, exemplary HLA-DR-specific humanized monoclonal antibodies of the present invention comprise one or more complementarity determining region (CDR) of murine monoclonal antibody DN1921 light chain variable domain (SEQ ID NO: 2) operably fused to human light chain framework (FR) domains 1, 2, 3, and/or 4 to create a humanized HLA-DR-specific light chain variable domain that is, optionally, operably fused to a human light chain constant domain exemplified herein by the human IgKappa light chain constant domain presented in SEQ ID NO: 3.

Humanized monoclonal antibodies based on DN1921 are capable of inducing apoptosis in a tumor cell expressing HLA-DR and are immunosuppressive when administered in vivo. DN1921 CDRs suitable for generating humanized antibodies according to the present invention are presented as SEQ ID NO: 17 (DN1921 $V_H$ CDR1), SEQ ID NO: 19 (DN1921 $V_H$ CDR2), SEQ ID NO: 21 (DN1921 $V_H$ CDR3), SEQ ID NO: 6 (DN1921 $V_L$ CDR1), SEQ ID NO: 8 (DN1921 $V_L$ CDR2), and SEQ ID NO: 10 (DN 1921 $V_L$ CDR3).

Futher exemplary HLA-DR-specific humanized monoclonal antibodies of the present invention comprise one or more complementarity determining region (CDR) of murine monoclonal antibody DN1924 heavy chain variable domain (SEQ ID NO: 35) operably fused to human framework (FR) domains 1, 2, 3, and/or 4 to create a humanized HLA-DR-specific heavy chain variable domain that is, optionally, operably fused to a human heavy chain constant domain wherein the constant domain is selected from the group consisting of IgM, IgD, $IgG_1$, $IgG_2$, $IgG_3$, $IgG_4$, IgE, $IgA_1$ and $IgA_2$ and exemplified herein by the human $IgG_2$ heavy chain constant domain presented in SEQ ID NO: 36.

Alternatively or additionally, further exemplary HLA-DR-specific humanized monoclonal antibodies of the present invention comprise one or more complementarity determining region (CDR) of murine monoclonal antibody DN1924 light chain variable domain (SEQ ID NO: 24) operably fused to human framework (FR) domains 1, 2, 3, and/or 4 to create a humanized HLA-DR-specific chain variable domain that is, optionally, operably fused to human light chain constant domain wherein the constant domain is exemplified herein by the human IgKappa light chain constant domain presented in SEQ ID NO: 25.

Humanized monoclonal antibodies based on DN1924 are capable of inducing apoptosis in a tumor cell expressing HLA-DR and are non-immunosuppressive when administered in vivo. DN1924 CDRs suitable for generating humanized antibodies according to the present invention are presented as SEQ ID NO: 39 (DN1924 $V_H$ CDR1), SEQ ID NO: 41 (DN1924 $V_H$ CDR2), SEQ ID NO: 43 (DN1924 $V_H$ CDR3), SEQ ID NO: 28 (DN1924 $V_L$ CDR1), SEQ ID NO: 30 (DN1924 $V_L$ CDR2), and SEQ ID NO: 32 (DN1924 $V_L$ CDR3).

Flanking each CDR are framework (FR) regions that are primarily responsible for folding the V region into the antigen-binding site, particularly the FR residues directly adjacent to the CDRs. Some FR residues may contact bound antigen. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs that form an antigen-binding surface. There are conserved structural regions of FRs that influence the folded shape of the CDR loops into certain "canonical" structures—regardless of the precise CDR amino acid sequence. Further, certain FR residues are known to participate in non-covalent interdomain contacts that stabilize the interaction of the antibody heavy and light chains.

Methods for humanizing non-human antibodies are well known in the art. Generally, a humanized antibody has one or more amino acid residue introduced into it from a source that is non-human. Humanization can be achieved by grafting CDRs into a human supporting FR prior to fusion with an appropriate human antibody constant domain. See, Jones et al., *Nature* 321:522-525 (1986); Riechmann et al., *Nature* 332:323-327 (1988); Verhoeyen et al., *Science* 239:1534-1536 (1988).

Alternatively, rodent CDRs can be supported by recombinantly veneered rodent FRs. See, European Patent Publication No. 519,596, published Dec. 23, 1992. See, also, U.S. Pat. Nos. 5,530,101, 5,585,089, 5,693,762, and 6,180,370 to Queen; U.S. Pat. No. 5,859,205 to Adair; and U.S. Pat. No. 5,225,539 to Winter, each of which patents is incorporated herein by reference in its entirety.

In practice, humanized antibodies are typically human antibodies in which some CDR residues and possibly some framework residues are substituted by residues from analogous sites in rodent antibodies. Thus, each of the humanized HLA-DR-specific antibodies of the present invention include at least one, two, or three non-human heavy chain CDR and/or at least one, two, or three non-human light chain CDR, respectively, interposed between human heavy and light chain FRs, which provide support to the CDRs and define the spatial relationship of the CDRs one to the other.

Fully Human Antibodies

Fully-human antibodies can be generated through phage display and transgenic mouse methodologies. DNA fragments encoding antibody scFv fragments identified by phage display technology are combined through recombinant techniques to generate complete "human" antibodies. To generate antibodies from transgenic mice, hybridomas are prepared and screened as for conventional monoclonal antibody methodology.

Methodology for generating fully-human antibodies by phage display technology are described in Hoogenboom et al., *J. Mol. Biol.* 227:381 (1991) and Marks et al., *J. Mol. Biol.* 222:581 (1991). See, also, U.S. Pat. Nos. 6,248,516, 6,291, 158, 6,291,159, 6,291,160, 6,291,161, 5,969,108, 6,172,197, 5,885,793, 6,265,150, 5,223,409, 5,403,484, 5,571,698, 5,837,500, and 6,300,064, each of which is incorporated herein by reference.

Transgenic animal systems for generating fully-human antibodies are disclosed in U.S. Pat. Nos. 6,150,584, 6,114, 598, 6,162,963, 6,075,181, and 5,770,429, each of which is incorporated herein by reference.

Additional techniques that are also available for the preparation of human monoclonal antibodies are described, e.g., in Cole et al., "Monoclonal Antibodies and Cancer Therapy," p. 77 (ed. Alan R. Liss, 1985) and Boerner et al., *J. Immunol.* 147(1):86-95 (1991).

Antigen-Binding Fragments Variants and Derivatives of HLA-DR Antibodies

The present invention also contemplates HLA-DR antigen-binding fragments, variants, and/or derivatives of any of the aforementioned HLA-DR-specific monoclonal antibodies. Each of the inventive HLA-DR antigen-binding fragments, variants, and derivatives are capable of inducing apoptosis in an HLA-DR expressing tumor cell, but not an HLA-DR-expressing normal cell. Within certain embodiments, HLA-DR antigen-binding fragments, variants, and derivatives, for example those based upon monoclonal antibody DN1921, are immunosuppressive when administered in vivo. In other embodiments, HLA-DR antigen-binding fragments, variants, and derivatives, for example those based upon monoclonal antibody DN1924, are non-immunosuppressive when administered in vivo.

Methodology for generating therapeutically useful HLA-DR-specific antigen-binding fragments capable of exhibiting immunological binding properties of the corresponding full-length HLA-DR-specific antibody molecule are readily available in the art. The methods of the present invention require that HLA-DR-specific antibodies be bivalent, tetravalent, or multivalent in order to facilitate cross-linking of HLA-DR molecules and thereby stimulate apoptosis. Accordingly one or m ore fragments of an HLA-DR-specific antibody may be bound to a solid support thereby facilitating the cross-linking of HLA-DR.

The proteolytic enzyme papain preferentially cleaves IgG molecules to yield several fragments, two of which (the "F(ab)" fragments) comprise a covalent heterodimer that includes an intact antigen-binding site. The enzyme pepsinis-able to cleave IgG molecules to provide several fragments, including the "F(ab')$_2$" fragment that comprises both antigen-binding sites. An "Fv" fragment can be produced by preferential proteolytic cleavage of an IgM, and on occasions an IgG or IgA antibody molecule. Fv fragments may, alternatively, be generated using recombinant techniques known in the art. The Fv fragment includes a non-covalent $V_H$::$V_L$ heterodimer including an antigen-binding site that retains much of the antigen recognition and binding capabilities of the native antibody molecule. Inbar et al., *Proc. Nat. Acad. Sci. USA* 69:2659-2662 (1972); Hochman et al., *Biochem.* 15:2706-2710 (1976); and Ehrlich et a l., *Biochem* 19:4091-4096 (1980).

A single chain Fv ("sFv") polypeptide is a covalently linked $V_H$::$V_L$ heterodimer that is expressed from a gene fusion including $V_H$- and $V_L$-encoding genes linked by a peptide-encoding linker. Huston et al., *Proc. Nat. Acad. Sci. USA* 85(16):5879-5883 (1988). A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513, 5,132,405, and 4,946,778.

Polynucleotides encoding antibodies, and antigen-binding fragments thereof, according to the present invention may be generated by conventional molecular biology and recombinant DNA methodology. Such methodology is explained fully in the literature. See, e.g., Sambrook et al., Molecular Cloning: A Laboratory Manual (2nd Edition, 1989); Maniatis et al., Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984). Each of these publications is incorporated by reference in its entirety.

Briefly, DNA sequences encoding, for example, an antibody heavy or light chain may be ligated into an appropriate expression vector wherein the expression vector comprises a transcriptional promoter in operable linkage to the polynucleotide encoding the antibody region and transcription termination signals 3' to the polynucleotide encoding the antibody region. Suitable expression vectors may also provide translational start sites, Kozak sequences to direct translation initiation, and stop codons to end translation. In addition, expression vectors may also comprise one or more polynucleotide sequences that encode polypeptides, such as His-His-His-His-His-His (SEQ ID NO: 71) or the FLAG® sequence Asp-Tyr-Lys-Asp-Asp-Asp-Asp-Lys (SEQ ID NO: 72) (Sigma-Aldrich, St. Louis, MO), which facilitates detection and affinity purification of the antibody polypeptide.

Expression may be achieved in any appropriate host cell that has been transformed or transfected with an expression vector containing a DNA molecule that encodes a recombinant polypeptide. Suitable host cells include prokaryotes, yeast and higher eukaryotic cells. Typically, the host cells employed are from a mammalian cell line such as COS or CHO. Supernatants from suitable host/vector systems which secrete recombinant antibody polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Antibody fragments, such as Fab fragments, may alternatively be synthesized by conventional polypeptide synthesis methodology. For example, such antibody fragments may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146 (1963). Equipment for automated synthesis of polypeptides is commercially available from suppliers such as Perkin Elmer/Applied BioSystems Division (Foster City, Calif.), and may be operated according to the manufacturer's instructions.

Thus, HLA-DR-specific antibodies and fragments thereof according to the present invention encompass fragments, derivatives, and variants so long as the fragments, derivatives, and variants do not substantially affect the antigen-binding properties of the HLA-DR binding specificity and apoptotic, non-immunosuppressive activities.

A polypeptide or protein "fragment, derivative, and variant," as used herein, is a polypeptide or protein that differs from a native polypeptide or protein in one or more substitutions, deletions, additions and/or insertions, such that the antigen-binding activity of the polypeptide or protein is not substantially diminished. In other words, the ability of a variant to specifically bind to HLA-DR may be enhanced or unchanged, relative to the parent HLA-DR-specific antibody or may be diminished by less that 50%, and typically less than 20%, relative to the parent antibody, without affecting the efficacy of the resulting HLA-DR-specific antibody or fragment thereof. Generally, suitable HLA-DR-specific antibody derivatives or variants may be characterized by assessing the ability of the derivative or variant to induce apoptosis in an HLA-DR expressing neoplastic cell.

As used herein, the term "variant" comprehends nucleotide or amino acid sequences different from the specifically identified sequences, wherein one or more nucleotides or amino acid residues is deleted, substituted, or added. Variants may be naturally-occurring allelic variants, or non-naturally occurring variants. Variant sequences (polynucleotide or polypeptide) preferably exhibit at least 70%, more preferably at least 80% or at least 90%, more preferably yet at least 95%, and most preferably, at least 98% identity to a sequence of the present invention.

Percentage identity is determined by aligning the two sequences to be compared as described below, determining the number of identical residues in the aligned portion, dividing that number by the total number of residues in the inventive (queried) sequence, and multiplying the result by 100. In addition to exhibiting the recited level of sequence similarity, variant sequences of the present invention preferably exhibit an antigen-binding ity that is substantially similar to the antigen-binding of the sequence against which the variant is compared.

Variants may contain "conservative amino acid substitutions," defined as a substitution in which one amino acid is substituted for another amino acid that has similar properties, such that the secondary structure and hydropathic nature of the polypeptide is substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes.

Antigen-binding fragments, derivatives, and variants of a polypeptide may be identified by first preparing antibody fragments by either chemical or enzymatic digestion of the antibody, or by mutation analysis of the polynucleotide that encodes the antibody and subsequent expression of the resulting mutant. The polypeptide fragments or mutant polypeptides are then tested to determine which portions retain biological activity, using, for example, the representative assays provided below.

Fragments, derivatives, and variants of the inventive antibodies may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized the Merrifield solid-phase synthesis method as discussed above.

Variants may also be prepared using standard mutagenesis techniques, such as oligonucleotide-directed, site-specific mutagenesis. Kunkel, *Proc. Natl. Acad. Sci. USA* 82:488-492 (1985). Sections of polynucleotide sequence may also be removed using standard techniques to permit preparation of truncated polypeptides. Variants may additionally, or alternatively, be modified by, for example, the deletion or addition of amino acids that have minimal influence on the immunogenicity, secondary structure and hydropathic nature of the polypeptide.

HLA-DR-specific antibody fragments, derivatives, and variants preferably exhibit at least about 70%, more preferably at least about 80% or 90% and most preferably at least about 95% or 98% sequence identity to the native HLA-DR-specific antibody. Polypeptide sequences may be aligned, and percentages of identical amino acids in a specified region may be determined against another polypeptide, using computer algorithms that are publicly available. The alignment and identity of polypeptide sequences may be examined using the BLASTP algorithm. The BLASTP algorithm is described in Pearson and Lipman, *Proc. Natl. Acad. Sci. USA* 85:2444-2448 (1988); and in Pearson, *Methods in Enzymol.* 183:63-98 (1990).

The BLASTP software is available on the NCBI anonymous FTP server and is available from the National Center for Biotechnology Information (NCBI), National Library of Medicine, Building 38A, Room 8N805, Bethesda, Md. 20894. The BLASTP algorithm Version 2.0.6 [Sep. 10, 1998] and Version 2.0.11 [Jan. 20, 2000] set to the default parameters described in the documentation and distributed with the algorithm, is exemplary for use in the determination of variants according to the present invention. The use of the BLAST family of algorithms, including BLASTP, is described at NCBI's website and in the publication of Altschul et al., "Gapped BLAST and PSI-BLAST: a new generation of protein database search programs," *Nucleic Acids Res.* 25:3389-3402 (1997).

The "hits" to one or more database sequences by a queried sequence produced by BLASTP, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The percentage identity of a polypeptide sequence is determined by aligning polypeptide sequences using appropriate algorithms, such as BLASTP, set to default parameters; identifying the number of identical amino acids over the aligned portions; dividing the number of identical amino acids by the total number of amino acids of the polypeptide of the present invention; and then multiplying by 100 to determine the percentage identity.

The BLASTP algorithm also produces "Expect" values for polypeptide alignments. The Expect value (E) indicates the number of hits one can "expect" to see over a certain number of contiguous sequences by chance when searching a database of a certain size. The Expect value is used as a significance threshold for determining whether the hit to a database indicates true similarity. For example, an E value of 0.1 assigned to a polypeptide hit is interpreted as meaning that in a database of the size of the SwissProt database, one might expect to see 0.1 matches over the aligned portion of the sequence with a similar score simply by chance. By this criterion, the aligned and matched portions of the sequences then have a probability of 90% of being related. For sequences having an E value of 0.01 or less over aligned and matched portions, the probability of finding a match by chance in the SwissProt database is 1% or less using the BLASTP algorithm.

According to one embodiment, "variant" HLA-DR-specific antibodies, with reference to each of HLA-DR-specific antibody and antibody fragment of the present invention, preferably comprise sequences having the same number or fewer amino acids than each of the HLA-DR-specific antibodies of the present invention and producing an E value of 0.01 or less when compared to the HLA-DR-specific antibody of the present invention.

In a ddition to having a specified percentage identity to an inventive HLA-DR-specific antibody, variant antibodies preferably have additional structure and/or antigen-binding features in common with the inventive HLA-DR-specific antibody. Antibodies having a specified degree of identity to an HLA-DR-specific antibody of the present invention share a high degree of similarity in their primary structure and have substantially similar antigen-binding properties. In addition to sharing a high degree of similarity in their primary structure to HLA-DR-specific antibodies of the present invention, antibodies having a specified degree of identity to, or capable of specifically binding to HLA-DR preferably have at least one of the following features: (i) they have substantially the same antigen-binding properties as an inventive HLA-DR-specific antibody; or (ii) they contain identifiable domains in common such as, for example, CDR and/or framework regions.

Conjugates

Depending upon the precise therapeutic and/or diagnostic application contemplated, it may be desireable to couple an antibody of the present invention, or fragment thereof, to one or more therapeutic agents. Suitable agents in this regard include radionuclides, differentiation inducers, drugs, toxins, and derivatives thereof. Exemplary suitable radionuclides include $^{90}Y$, $^{123}I$, $^{125}I$, $^{131}I$, $^{186}Re$, $^{188}Re$, $^{211}At$, and $^{212}Bi$. Exemplary suitable drugs include methotrexate, and pyrimidine and purine analogs. Exemplary suitable differentiation inducers include phorbol esters and butyric acid. Exemplary suitable toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be affected, for example, through amino groups, carboxyl groups, sulfhydryl groups or oxidized carbohydrate residues. Such methodology are descrived, e.g., in U.S. Pat. No. 4,671,958.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), and acid-catalyzed hydrolysis (e.g., U.S. Pat. No. 4,569,789).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234), peptides and polysaccharides such as aminodextran (e.g., U.S. Pat. No. 4,699,784). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673, 562 discloses representative chelating compounds and their synthesis.

The term "cytotoxic drug" as used herein refers to a drug which is used to inhibit the growth, or facilitate the death of cancer cells. Examples of cytotoxic drugs include chemotherapeutic agents such as ara-C, bleomycin, cis-platin, cladribine, cyclophosphamide, doxorubicin, etoposide, and 5-fluorouracil (5-FU).

Assay Systems for Identifying and Characterizing Anti-HLA-DR Antibodies

The following assay systems may be suitably employed for the routine identification and characterization of HLA-DR-specific, apoptotic, non-immunosuppresive antibodies according to the present invention.

Class II MHC

Anti-HLA-DR mAb that are both "immunosuppressive and cytotoxic" may inhibit antigen presentation by recognizing the first domains and binding to an epitope located close to the peptide-binding groove. The anti-HLA-DR mAb of the present invention, e.g. DN1924 are "cytotoxic only". Accordingly, it is likely that the precise sequence of HLA-DR to which such a "cytotoxic only" antibody binds, is not identical to that of antibodies which are both "immunosuppressive and cytotoxic." Vidovic et al., *Eur. J. Immunol.* 25:3349-3355 (1995).

Apoptotic Cell Death

As described above, apoptosis (programmed cell death) has been associated with the binding of anti-MHC Class II antibodies to Class II-expressing cells. Class II MHC-encoded molecules expressed on the surface of APC (such as B lymphocytes, macrophages, monocytes, dendritic cells, etc.) function as restriction elements for the presentation of antigen to T lymphocytes, an interaction that ultimately leads to activation and differentiation of both cell types.

HLA-DR mediated cell death has been demonstrated to be very rapid, independent of Fc receptors and complement, and non-necrotic. Truman et al., *Int. Immunol.* 6(6):887-896 (1994) and Truman et al., *Blood* 89(6):1996-2007 (1997).

The present discovery relates to the role of anti-HLA-DR antibodies in triggering apoptosis of tumor cells and thus provides methods for inducing programmed cell death in such cells. In a exemplary embodiment, the anti-HLA antibodies, and fragments thereof which are capable of crosslinking the HLA-DR antigen, are useful in the study or treatment of conditions which are mediated by tumor cells which express HLA-DR, i.e. to treat or prevent disorders associated with HLA-DR-expressing tumor cells. Accordingly, the antibodies of the present invention are useful to treat various diseases, including, but not limited to, any disease characterized by cancer of B cell origin (where increased apoptosis would be desirable), e.g., Hodgkin's and non-Hodgkin's lymphomas, chronic lymphocytic leukemia, myeloma and plasmacytoma. Holland et al., *Cancer Med.* 2:2697-2828 (1996).

Evaluation of the Mechanism of Cell Death

This section describes in vitro assays which are useful for evaluating the extent of apoptotic cell death. Cell death may be detected by staining of cells with propidium iodide (PI), or by use of assays specific to apoptotic cell death, e.g. staining with annexin V. Vermes et al., *J. Immunol. Meth.* 184:39-51 (1995). Necrotic cell death may be distinguished from apoptotic cell death by evaluating the results of a combination of the assays for cell viability, as described below, together with microscopic observation of the morphology of the relevant cells.

Assay for Necrotic Cell Death

Necrosis is a passive process in which collapse of internal homeostasis leads to cellular dissolution involving a loss of integrity of the plasma membrane and subsequent swelling, followed by lysis of the cell. Schwartz et al., 1993. Necrotic cell death is characterized by loss of cell membrane integrity and permeability to dyes such as propidium iodide (PI) which is known by those in the art to bind to the DNA of cells undergoing primary and secondary necrosis. Vitale et al., *Histochemistry* 100:223-229 (1993) and Swat et al., *J. Immunol. Methods* 137:79-87 (1991). Necrosis may be distinguished from apoptosis in that cell membranes remain intact in the early stages of apoptosis. As a consequence dye exclusion assays using PI may be used in parallel with an assay for apoptosis, as described below in order to distinguish apoptotic from necrotic cell death. Fluorescent-activated cell sorter (FACS) based flow cytometry assays using PI allow for rapid evaluation and quantitation of the percentage of necrotic cells.

Assay for Apoptotic Cell Death

Detection of programmed cell death or apoptosis may be accomplished as will be appreciated by those in the art. The percentage of cells undergoing a poptosis may be measured at various times after stimulation of apoptosis with or without administration of anti-HLA-DR antibodies. The morphology of cells undergoing a poptotic cell death is generally characterized by a shrinking of the cell cytoplasm and nucleus and condensation and fragmentation of the chromatin. Wyllie et al., *J. Pathol.* 142:67-77 (1984).

Partial DNA degradation in apoptotic B cells has been previously reported. Truman et al., *Int. Immunol.* 6:887-896 (1994) and Cohen et al., *Annu. Rev. Immunol.* 10:267-293 (1992). Consistent with this observation, DNA fragmentation was not detected after incubating tumor B cells with an earlier described apoptogenic anti-HLA-DR mAb, however, the relative cell size and PI-uptake flow cytometry profiles of these cultures are essentially the same as those previously demonstrated for cells undergoing apoptosis. Vidovic et al., *Cancer Lett.* 128:127-135 (1988); Newell et al., *Proc. Natl. Acad. Sci. U.S.A.* 90:10459-10463 (1993); and Truman et al. (1994).

Utilities

Uses for Anti-HLA-DR Antibodies

HLA-DR-specific antibodies of the present invention may be employed in diagnostic and therapeutic compositions and methods. For example, HLA-DR-specific antibodies may be used in diagnostic assays for, and therapy involving HLA-DR expressing tumor cells, e.g., detecting expression of such cells in tissues or serum and serving as the basis for therapy to improve the clinical outcome of subjects with such tumors.

Various diagnostic assay techniques known in the art may be used, such as competitive binding assays, direct or indirect sandwich assays and immunoprecipitation assays conducted in either heterogeneous or homogeneous phases. Zola, "Monoclonal Antibodies: A Manual of Techniques," pp. 147-158 (CRC Press, Inc., 1987). Antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Molecules that facilitate specific binding include pairs, such as biotin and streptavidin, digoxin and antidigoxin, etc. One of the members of a pair of molecules which facilitate specific binding may be labeled with a molecule that provides for detection in accordance with known procedures, wherein the label can directly or indirectly provide a detectable signal. Any method known in the art for conjugating the antibody to the detectable moiety may be employed, including those methods described by Hunter et al., *Nature* 144:945 (1962); David et al., *Biochemistry* 13:1014 (1974); Pain et al., *J. Immunol. Meth.* 40:219 (1981); and Nygren, *J. Histochem. and Cytochem.* 30:407 (1982).

HLA-DR-specific antibodies also are useful for the affinity purification of HLA-DR expressing cancer cells from cell culture or natural sources. In such methods, antibodies against a HLA-DR are immobilized on a suitable support, such a Sephadex resin or filter paper, using methodologies that are well known in the art. Immobilized antibody is contacted with a sample containing HLA-DR expressing cancer cells to be purified, and the solid support is washed with a suitable medium that will remove substantially all the material in the sample except the HLA-DR expressing cancer cells, which are bound to the immobilized antibody. The support is washed with another suitable medium that releases the HLA-DR expressing cancer cells from the immobilized antibody.

Biological Effects of Anti-HLA-DR Specific Monoclonal Antibodies

HLA-DR-specific monoclonal antibodies of the present invention recognize the first domains of HLA-DR. The antibody or CDR region of the HLA-DR-specific monoclonal antibodies of the invention are immunoreactive with, and capable of inducing apoptosis in, tumor cells that express detectable levels of the HLA-DR. The HLA-DR-specific murine monoclonal antibody, DN1924, and murine/human chimeric monoclonal antibody have demonstrated in vitro specificity for induction of apoptosis in tumor (plasmacytoma MC/CAR) cells relative to non-neoplastic cells both of which express HLA-DR. See, Example 2 and FIGS. 2-4 and Example 7, FIGS. 8A-F. In addition, the lack of interference with normal $T_h$ responses by DN1924 has been demonstrated in vitro. See, Example 2 and FIG. 5.

In Vivo Cancer Therapy with Apoptotic HLA-DR-Specific Antibodies

The antibodies of the present invention are therapeutically effective and can stimulate apoptotic cell death of tumor cells that express the HLA-DR antigen. These findings raise the possibility of a selective antibody-based anti-tumor therapy for HLA-DR positive cancers, particularly those of the blood.

The tumoricidal effects of anti-class II MHC mAb can be achieved without simultaneous suppression of class II-dependent immune responses, although both properties are associated with mAb recognizing the first domains of the protein.

Antibodies having the desired therapeutic effect may be administered in a physiologically acceptable carrier to a host, and may be administered in a variety of ways, e.g., parenterally, subcutaneously (SC), intraperitoneally (IP), intravenously (IV), etc. Depending upon the manner of introduction, the antibodies may be formulated in a variety of ways. The concentration of therapeutically active antibody in the formulation may vary from about 1 mg/ml to 1 g/ml.

A "subject" for the purposes of the present invention includes both humans and other animals, particularly mammals. Thus the methods are applicable to both human therapy and veterinary applications. In the exemplary embodiment the subject is a mammal, and in the most exemplary embodiment the subject is human.

As used herein, the term "improved therapeutic outcome" or "decrease in the number of tumor cells" means a 50% decrease, preferably an 80% decrease, more preferably a 90% decrease, and even more preferably a 100% decrease in either the tumor size, or in the number of detectable circulating cancer cells in the blood and/or affected tissue or organ as determined by examination of a patient and/or samples taken from a patient prior to and following treatment.

The terms "treating", "treatment" and "therapy" as used herein refer to curative therapy, prophylactic therapy, and preventative therapy. By "therapeutically effective amount" as used herein is meant a dose that reduces or eliminate HLA-DR expressing tumor cells by stimulating apoptosis thereof. The exact dose will depend on the purpose of the treatment, and will be ascertainable by one skilled in the art using known techniques.

Preferably, the antibody is formulated for parenteral administration in a suitable inert carrier, such as a sterile physiological saline solution. For example, the concentration of antibody in the carrier solution is typically between about 1-100 mg/ml. The dose administered will be determined by route of administration. Exemplary routes of administration include parenteral or IV administration. A therapeutically effective dose is a dose effective to produce a significant increase in apoptotic cell death of HLA-DR expressing neoplastic cells. A significant increase in apoptotic cell death of HLA-DR expressing neoplastic cells is a 2-fold increase, more preferably a 5-fold increase, even more preferably a 10-fold increase, and most preferably a 20-fold increase in apoptotic cell death of HLA-DR expressing cells relative to cells which do not express a detectable amount of HLA-DR.

According to an important feature of the invention, the anti-HLA-DR antibody may be administered alone or in combination with other anti-cancer agents, such as chemotherapeutic agents, for example, cisplatin, taxol, methotrexate, etc.; tumor necrosis factor-alpha (TNF-"); FADD, PMA; ionomycin; staurosporine or Rituxan®.

The therapeutically effective amount of an anti-HLA-DR antibody, e.g., DN1924, can be estimated by comparison with established effective doses for known antibodies, taken together with data obtained for DN1924 in in vitro models for the apoptotic cell death of HLA-DR positive tumor cells, as described herein. As is known in the art, adjustments in the dose may be necessary due to antibody degeneration, systemic versus localized delivery, as well as the age, body weight, general health, sex, diet, time of administration, drug interactions and the severity of the condition. Such adjustments may be made and appropriate doses determined by one of skill in the art through routine experimentation.

Within certain embodiments, methods of the present invention may further provide a step of screening cells for antibodies having a desired antigen-binding specificity and/or affinity. As used herein, the term "antigen" broadly encompasses all those substances, molecules, proteins, nucleic acids, lipids and/or carbohydrates to which an antibody specifically binds and/or interacts.

Antibodies may be screened for exemplary antigen-binding specificity and/or affinity by any of the methodologies that are currently available in the art. For example, conventional cell panning, Western blotting and ELISA procedures may be employed to accomplish the step of screening for antibodies having a particular specificity. A wide range of suitable immunoassay techniques is available as can be seen by reference to U.S. Pat. Nos. 4,016,043, 4,424,279, and 4,018,653, each of which is incorporated herein by reference.

In one type of assay, an unlabelled anti-antibody is immobilized on a solid support and the antibody-containing sample to be tested is brought into contact with the immobilized anti-antibody. After a suitable period of time sufficient to allow formation of a first complex, a target antigen labeled with a reporter molecule capable of producing a detectable signal is then added and incubated, allowing time sufficient for the formation of a second complex of immobilized anti-antibody/antibody sample/test antigen. Uncomplexed material is washed away, and the presence of the antigen is determined by observation of a signal produced by the reporter molecule. The results may either be qualitative, by simple observation of the visible signal, or may be quantified by comparison with a control sample containing known amounts of antigen or antibody. Variations of this type of assay include a simultaneous assay, in which both sample and labeled antigen are added simultaneously to the bound antibody.

The term "solid support" as used herein refers to, e.g., microtiter plates, membranes and beads, etc. For example, such solid supports may be made of glass, plastic (e.g., polystyrene), polysaccharides, nylon, nitrocellulose, or teflon, etc. The surface of such supports may be solid or porous and of any convenient shape.

In a second type of assay, an antigen for which an antibody is sought is bound to a solid support. The binding processes are well known in the art and generally consist of cross-linking, covalently binding or physically adsorbing the antigen to the solid support. The polymer-antigen complex is washed in preparation for the test sample. An aliquot of the sample to be tested is then added to the solid phase complex and incubated for a period of time sufficient (e.g., 2-40 minutes or overnight if more convenient) and under suitable conditions (e.g., from about room temperature to about 38° C., such as 25° C.) to allow binding of antibody to the antigen. Following the incubation period, the solid support is washed and dried and incubated with an antibody to which a reporter molecule may be attached thereby permitting the detection of the binding of the second antibody to the test antibody complexed to the immobilized antigen.

Suitable solid supports include glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay.

An alternative assay system involves immobilizing the target antibody and exposing the immobilized target antibody to an antigen that may or may not be labeled with a reporter molecule. As used herein, the term "reporter molecule" refers to a molecule that, by its chemical, biochemical, and/or physical nature, provides an analytically identifiable signal that allows the screening for antibodies complexed with antigens or with second antibodies. Detection may be either qualitative or quantitative. The most commonly used reporter molecules employed in assays of the type disclose herein are enzymes, fluorophores, radioisotopes, and/or chemiluminescent molecules. In one particularly useful assay system, cultures of cell libraries expressing antibodies in the context of B cell receptors, on the surface of the cells, may be incubated with antigen coupled to a label, such as biotin, or carrying a recombinant epitope, such as the FLAG epitope. Castrucci et al., *J. Virol.* 66:4647-4653 (1992). After a suitable incubation time, the labeled antigen is washed away by pelleting the cells two or three times from suspension in ice-cold medium.

The cells may be further incubated in medium containing a suspension of beads conjugated to a reagent that will specifically bind the label attached to the antigen (e.g., streptavidin or avidin for the biotin label, or anti-FLAG antibody for the FLAG epitope). Cells that bind to the beads as an indirect consequence of binding the antigen of interest are separated from the remaining cells by appropriate means, and then returned to tissue culture to proliferate. Repetition of this process using increasingly limiting amounts of antigen results in enrichment for cells that bind to the antigen specifically and/or with high affinity. Cells that bind directly to the beads independently of prior binding to antigen may be removed by incubation with beads in the absence of antigen. Individual antigen-binding clones may then be purified, such as for example by fluorescence-activated cell sorting (FACS), after labeling the cells with antigen conjugated directly or indirectly to a suitable fluorochrome such as fluorescein.

In the case of an enzyme immunoassay (EIA), an enzyme is conjugated to the detection antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, β-galactosidase and alkaline phosphatase. In general, the enzyme-labeled antibody is added to a potential complex between an antigen and an antibody, allowed to bind, and then washed to remove the excess reagent. A solution containing the appropriate substrate is then added to the complex of antigen/test-antibody/labeled-antibody. The substrate reacts with the enzyme linked to the second antibody, giving a qualitative visual signal, which may be further quantified, usually spectrophotometrically, to indicate the amount of antibody present in the sample. Alternatively, fluorescent compounds, such as fluorescein and rhodamine, or fluorescent proteins such as phycoerythrin, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic color visually detectable with a light microscope or other optical instruments. As in the EIA, the fluorescent labeled antibody is allowed to bind to the antigen-antibody complex. After removing unbound reagent, the remaining tertiary complex is exposed to light of the appropriate wavelength. The fluorescence observed indicates the presence of the bound antibody of interest. Immunofluorescence and EIA techniques are both well established in the art. It will be understood that other reporter molecules, such as radioisotopes, and chemiluminescent and/or bioluminescent molecules, may also be suitably employed in the screening methods disclosed herein.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.The following Examples are offered by way of illustration not limitation.

EXAMPLES

Example 1

Generation of DN1921 and DN1924 Murine Monoclonal Antibodies

This Example demonstrates the generation of the murine DN1921 and DN1924 HLA-DR-specific monoclonal antibodies.

The mouse monoclonal HLA-DR-specific antibodies designated DN1921 and DN1924 were prepared according to standard techniques known in the art. Harlow and Lane, "Antibodies: A Laboratory Manual" (Cold Spring Harbor Laboratory, Cold Spring Harbor, N.Y., 1998). Inbred laboratory mice of BALB/c strain (Jackson Laboratory, Bar Harbor, Me.), hyperimmunized with an immunogen were donors of immune B cells. BALB/c-derived mutant B lymphoma line M12.C3, transfected with chimeric human/mouse class II gene was used as the immunogen. The MHC class II molecule expressed by this transfectant (designated M12.C3.25) was composed of the first extracellular (alpha 1 and beta 1) domains of the HLA-DR, and the second extracellular (alpha2 and beta2), transmembrane and intracytoplasmic domains of the corresponding mouse MHC class II molecule H2-E. Vidovic et al., *Eur. J. Immunol.* 25:3349-3355 (1995). Mice were immunized at monthly intervals with 5 IP injections, each consisting of $10^7$ (-irradiated (100 Gy) M12.C3.25 cells resuspended in 1 ml of phosphate buffered saline (PBS). Three days after the last injection, immune splenocytes were fused with the HAT-sensitive Ig-negative mouse myeloma cells PAI-0. Stocker et al., *Research Disclosure* 217:155-157 (1982).

The supernatant fluids of single hybridoma cultures were screened for either their toxicity on EBV-LCL RPMI 1788 after 4-hour incubation at 4° C., or their capability to suppress staphylococcus enterotoxin B (SEB) induced in vitro proliferation of human peripheral blood mononuclear cells (PBMC). Colonies, which were identified to secrete monoclonal antibodies of desired bioactivities in a stable fashion, were designated "DN1921" and "DN1924," respectively, and subcloned two times by the limiting dilution method. Using the standard isotyping kit (Zymed, South San Francisco, Calif.), DN1921 and DN1924 were both found to be of a mouse IgG1/kappa isotype.

Example 2

Evaluation of in vitro Tumoricidal Effects of the DN1924 Monoclonal Antibody

This Example demonstrates that murine HLA-DR-specific monoclonal antibody designated DN1924 is capable of inducing apoptosis in tumor cells expressing HLA-DR but not in normal (i.e. non-malignant) cells expressing HLA-DR.

Human cell lines MC/CAR (plasmacytoma) and RPMI 1788 (Epstein-Barr virus transformed lymphoblastoid B cell line, EBV-LCL) were purchased from ATCC (Rockville, Md.). Ritts et al., *Int. J. Cancer* 31:133-141 (1983). Cells were cultured at the density of $10^5$/ml in IMDM medium supplemented with 10% FCS, 2 mM L-glutamine, 0.1 mg/ml kanamycin sulfate, and $3\times10^{-5}$ M 2-ME (Gibco, Grand Island, N.Y.) at 37° C. in a humidified atmosphere containing 5% $CO_2$ (tissue culture incubator). Sterile filtered supernatant fluids of the HLA-DR-specific mAb-secreting mouse B-cell hybridoma cell line DN1924 and 10F12, cultured at $5\times10^5$ cells/ml, were added to the human cells at the final concentration of 20%. Following the indicated coculture period, cells were washed and their viability was determined after an additional 5 minute incubation with 1 μg/ml of propidium iodide (PI, Sigma, St. Louis, Mo.) and a subsequent analysis of cell size (forward light scatter, FSC) vs. red PI fluorescence on a FACScan® flow cytometer using CELLQuest 3.1f software (Becton-Dickinson, San Jose, Calif.). Otten et al., "Current Protocols in Immunology," pp. 5.4.1-5.4.19 (Coligan et al., ed., Greene & Wiley, New York, 1997). Live cells were shown to actively exclude PI, while dead cells took it up in a direct proportion to the accessibility of their DNA. Swat et al., (1991).

The ability of the DN1924 antibody to induce apoptosis of neoplastic cells was shown by coculture of 2 independent human B cell tumor lines (EBV-LCL RPMI 1788 and plasmacytoma MC/CAR which resulted in greater than 75% cell death. FIG. 2. The cytotoxic effect was completely absent in normoplastic (i.e., non-neoplastic) HLA-DR+ lymphocytes obtained from human peripheral blood. In contrast to DN1924, 10F12, an anti-DR mAb specific for a common epitope located within the second protein domains, did not affect viability of MC/CAR. FIG. 3.

Figure 1:
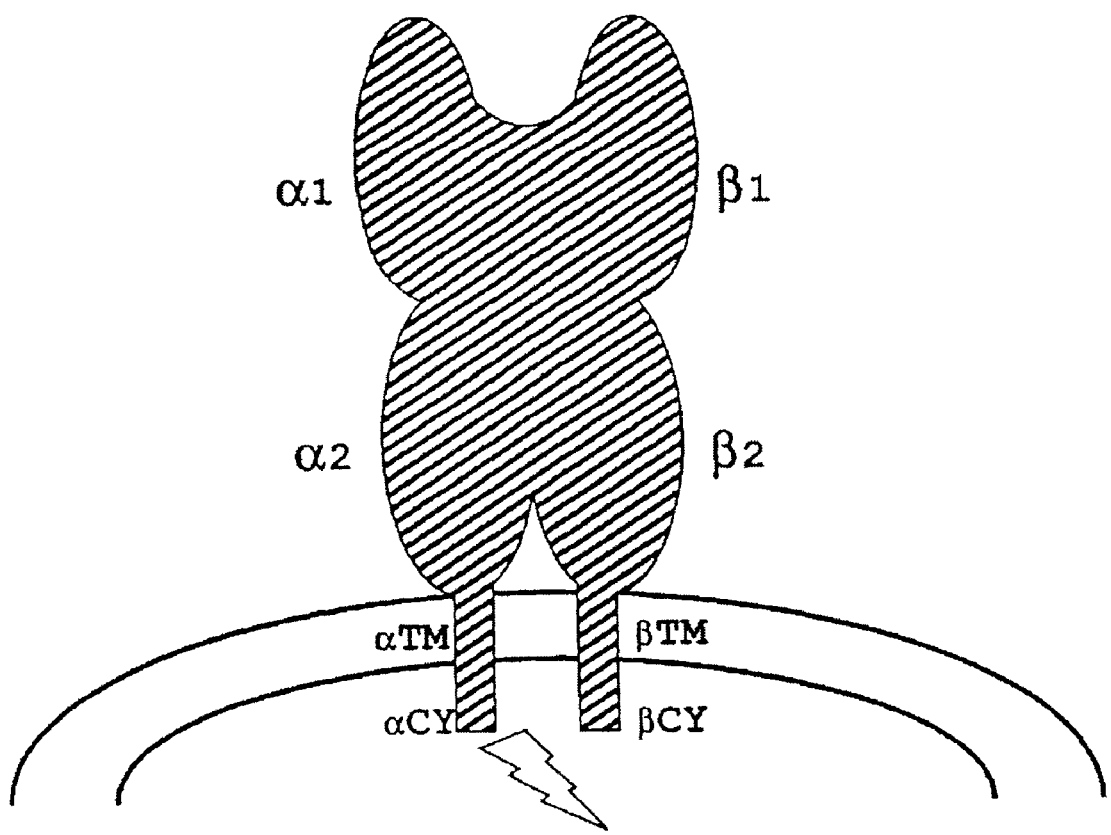
Figure 2A:
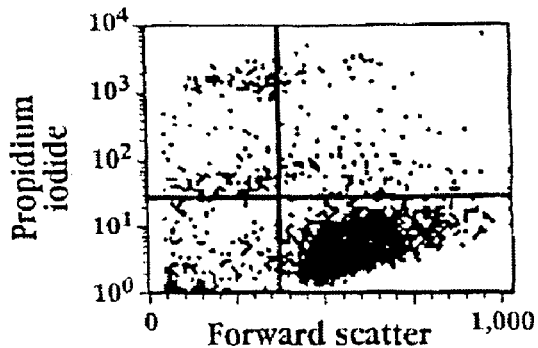
Figure 2B:
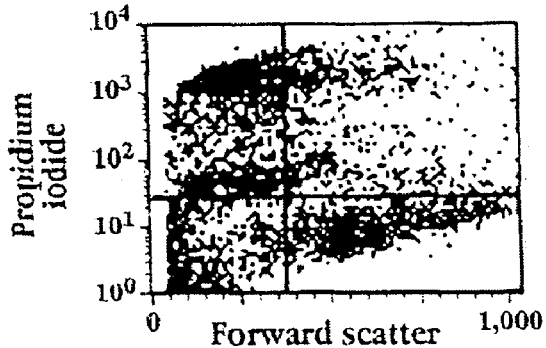
Figure 2C:
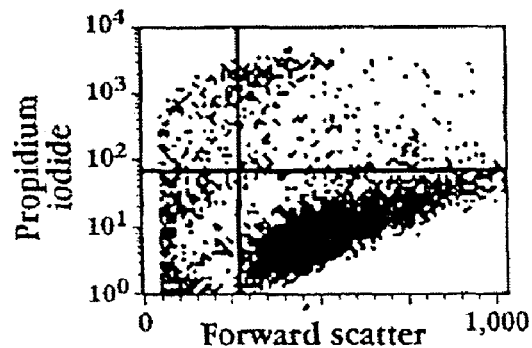
Figure 2D:
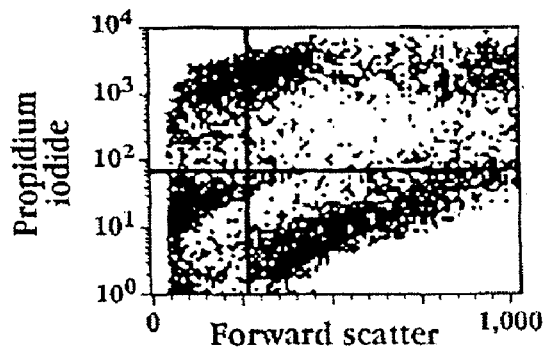
Figure 2E:
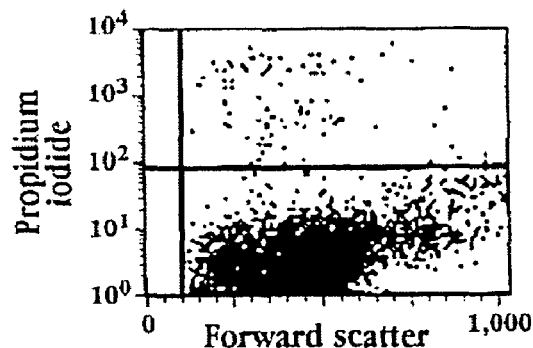
Figure 2F:
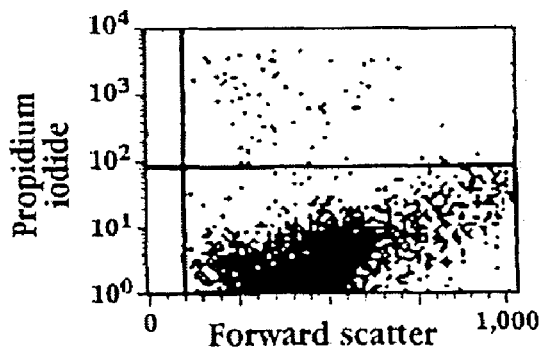
Figure 3A:
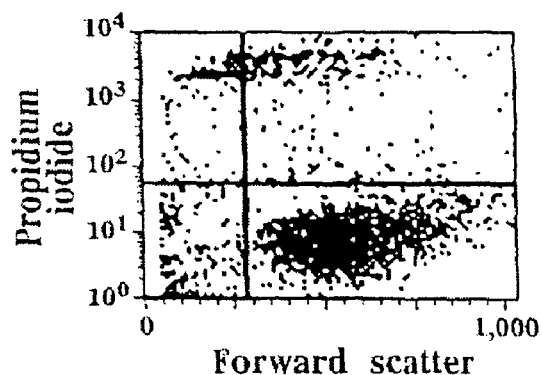
FIG. 3 shows the viability of the human cell lines after 16 h coculture with the indicated monoclonal antibody.
Figure 3B:
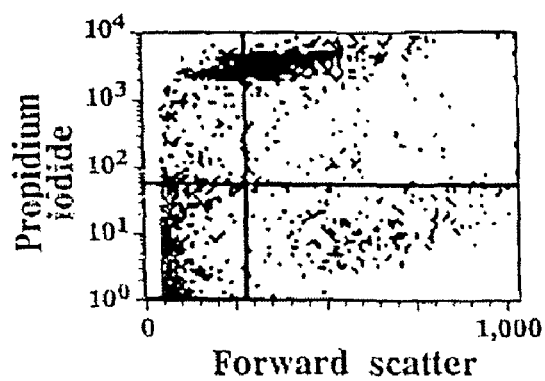
Figure 3C:
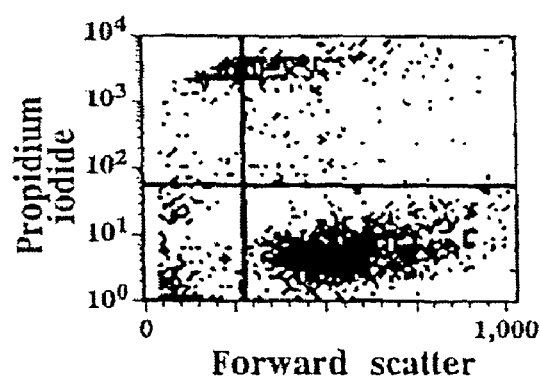
Figure 3D:
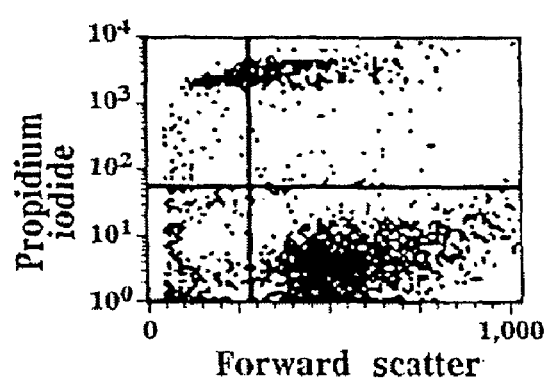
Figure 3E:
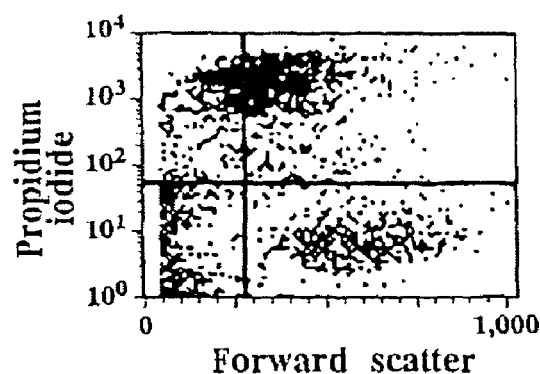
Figure 3F:
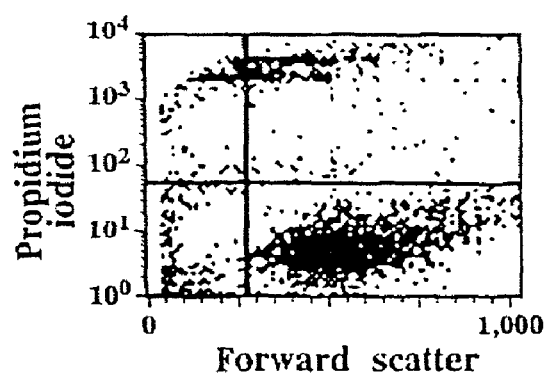
Figure 4A:
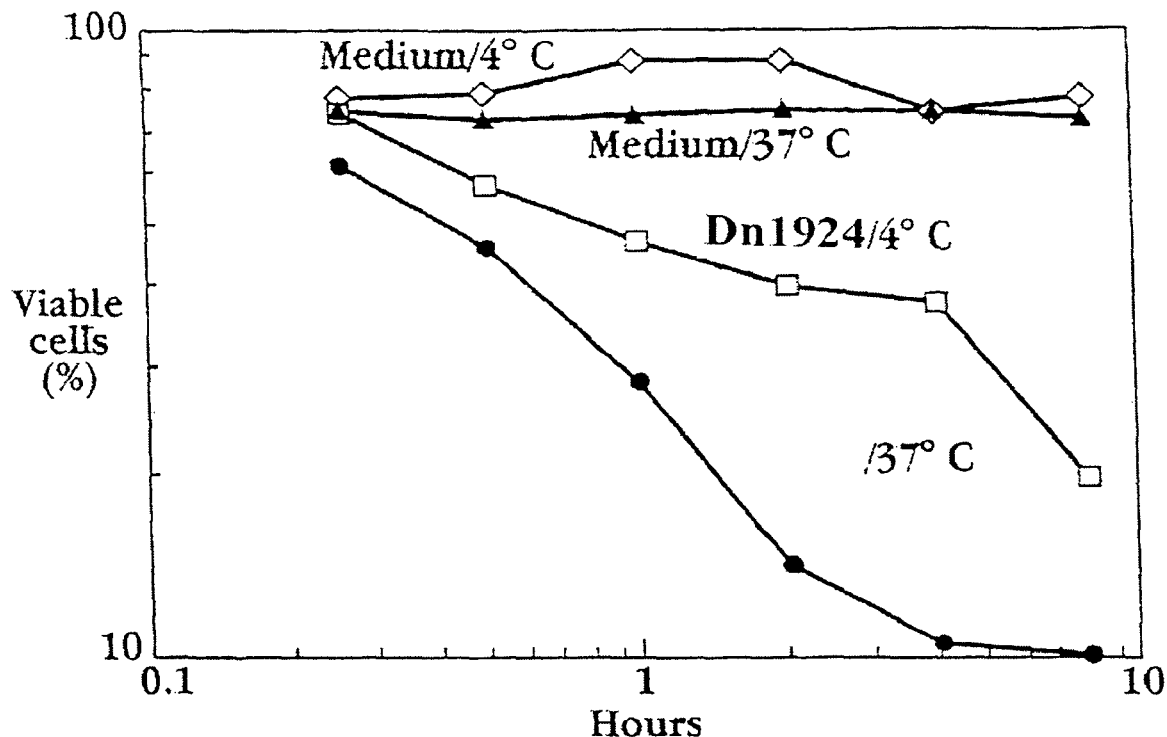
FIG. 4 shows the viability of EBV-LCL RPMI 1788 cells after incubation with the DN1924 monoclonal antibody under different temperature conditions and for various time periods, as indicated.
Figure 4B:
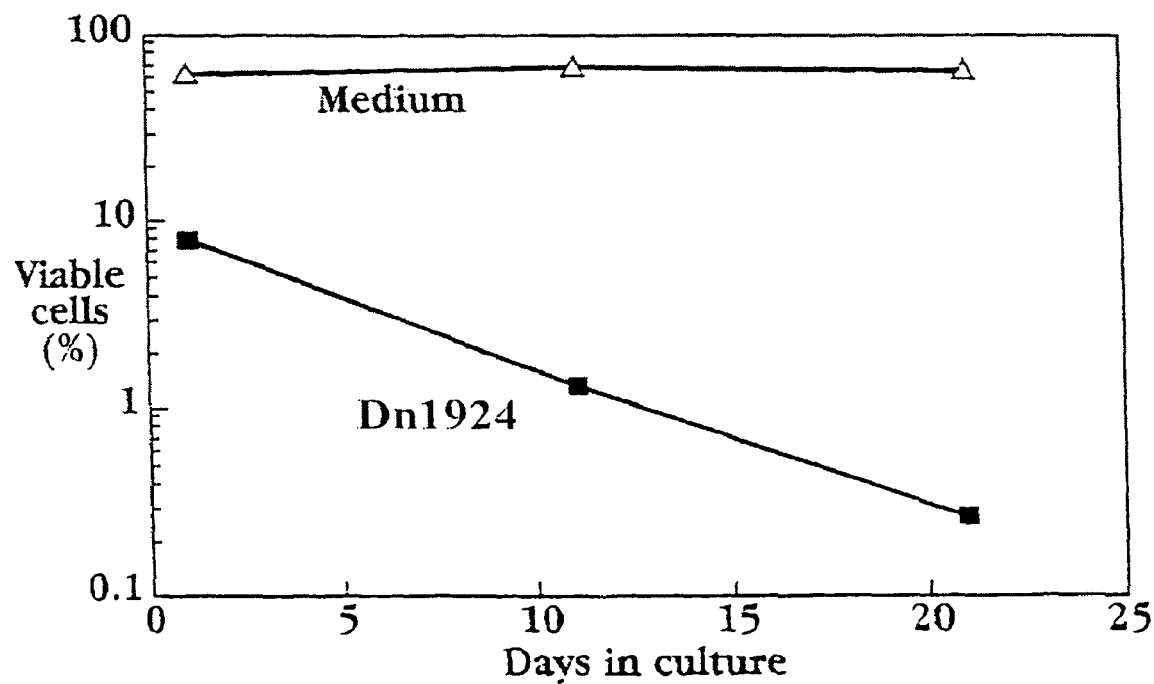
Figure 5:
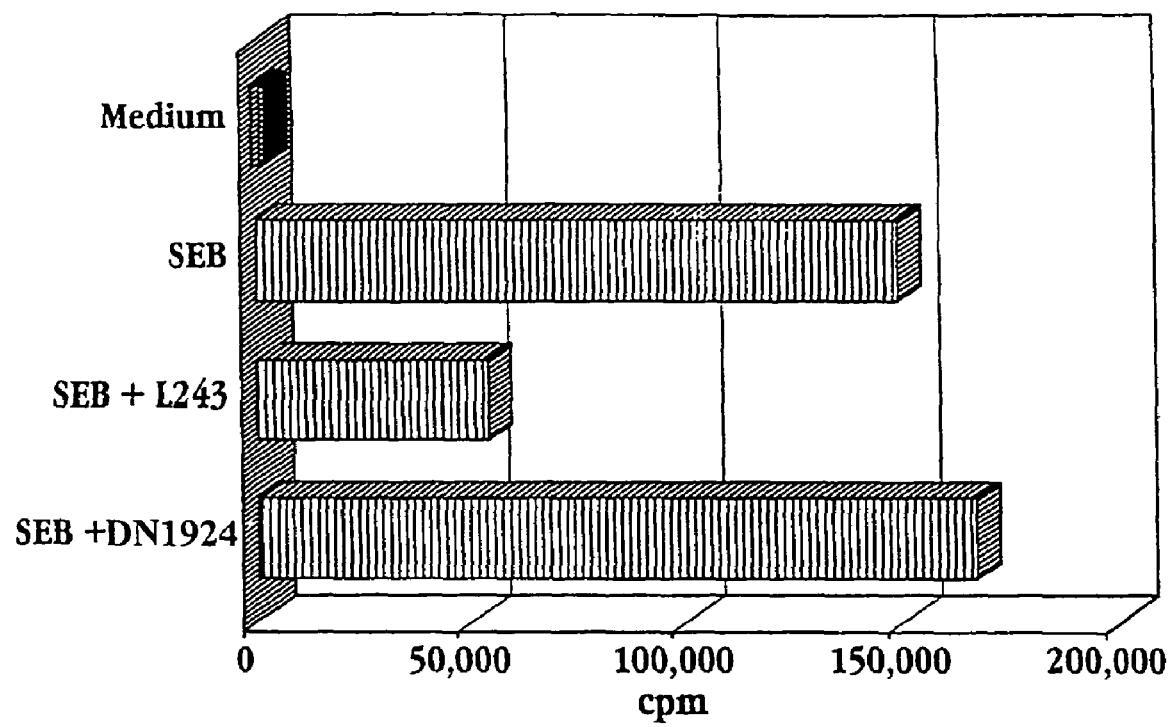
FIG. 5 shows the absence of immunosuppressive effects of the DN 1924 monoclonal antibody on the staphylococcal enterotoxin B (SEB) specific in vitro proliferative response of human PBMC, as indicated by [$^3$H]thymidine incorporation.

The cytotoxicity time course under two different incubation conditions is shown in FIG. 4, upper panel. It appeared that DN1924-induced cell death was temperature dependent; with the faster rate at human body temperature (37° C., the cytotoxic effect evident within 30 minutes, and retarded, yet still occurring at 4° C. (the cytotoxic effect evident after 1-2 hours). The undiminished tumorotoxicity of DN1924 even after the prolonged (3 weeks) coculture with tumor cells indicates their inability to become resistant to this antibody. FIG. 4, lower panel.

Example 3

The DN1924 HLA-DR-Specific Murine Monoclonal Antibody Exhibits Reduced Immunosuppressive Activity This Example demonstrates that the DN1924 HLA-DR-specific murine monoclonal antibody exhibits reduced levels of immunosuppressive activity.

HLA-DR dependent in vitro proliferative responses of human Th cells against Staphylococcal enterotoxin B (SEB) were generated as previously described. Mollick et al., *J. Immunol.* 146:463468 (1991). Briefly, $2\times10^5$ fresh human PBMC, obtained from a heparinized blood by Ficoll separation, were cultured with 0.1 μg/ml SEB (Toxin Technology, Sarasota, Fla.) in 0.2 ml of the IMDM medium supplemented with 10% FCS, 2 mM L-glutamine, 0.1 mg/ml kanamycin sulfate, and $3\times10^{-5}$ M 2-ME at 37° C. in a humidified atmosphere containing 5% $CO_2$ (tissue culture incubator) for 3 days. Sterile filtered supernatant fluids of the HLA-DR-specific mAb-secreting mouse B cell hybridoma cell lines DN1924 and L243 (ATCC, Rockville, Md.) cultured at $5\times10^5$ cells/ml, were added at the initiation of the assay at the final concentration of 20%. Lampson et al., *J. Immunol.* 125:293-299 (1980) and Fu et al., *Human Immunol.* 39:253-260 (1994). T cell proliferation of triplicate cultures was measured by [$^3$H]thymidine incorporation during the final 16 hours. Bradley, "Selected Methods in Cellular Immunology" pp. 153-174 (Mishell and Shiigi, eds., W.H. Freeman & Co., New York (1980). While mAb L243 suppressed about 70% of SEB-triggered T cell response, DN1924 had no effect (FIG. 5), although both mAbs recognize epitopes on the first HLA-DR domains.

Example 4

Figure 6:
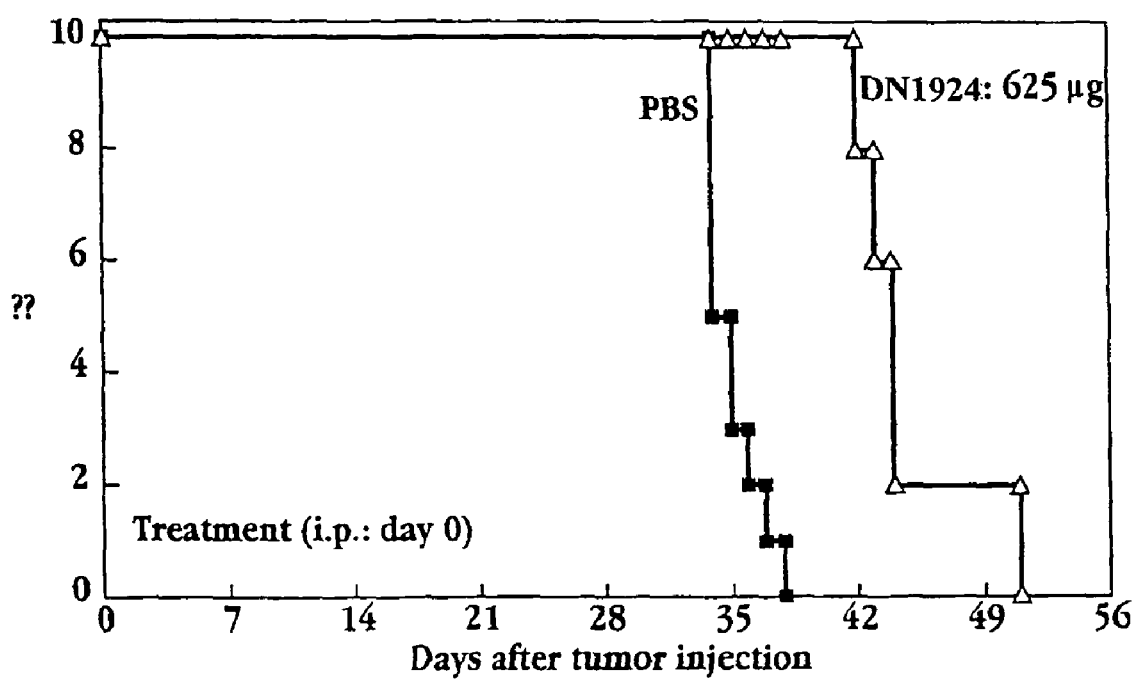
FIG. 6 shows the survival of scid mice injected with HLA-$DR_+$ human plasmacytoma MC/CAR, and treated with either DN 1924 (open triangles) or phosphate buffered saline (PBS; filled squares).

Evaluation of in vivo Anti-Tumor Activity of the DN1924 HLA-DR-Specific Murine Monoclonal Antibody The in vivo anti-tumor activity of DN1924 was evaluated in severe combined immunodeficiency inbred (scid) mice injected with the HLA-DR positive human plasmacytoma MC/CAR. Twenty 8-week-old mice, randomized according to their body weight were injected IP with $10^7$ MC/CAR cells in 0.1 ml RPMI 1640 medium per mouse. Ritts et al. (1983). Subsequently, half the animals received a single IP dose of 0.625 mg DN1924 antibody in 0.1 ml of PBS. The remaining mice were given corresponding IP injections of 0.1 ml PBS. Mice were monitored daily, and their survival recorded. As shown in FIG. 6, DN1924 exhibited a notable therapeutic activity, significantly prolonging the survival of tumor-bearing mice.

Example 5

Generation of Murine/Human Chimeric HLA-DR-Specific Monoclonal Antibodies Based on Murine DN1921 and DN1924

This Example describes the construction of murine/human chimeric HLA-DR specific monoclonal antibodies comprising the heavy and light chain variable regions of murine monoclonal antibodies DN1921 and DN1924 and the heavy chain constant regions of human $IgG_2$ and light chain constant regions of human IgKappa.

Variable region segments were cloned from hybridoma cells expressing the murine versions of each antibody (DN1924 and DN1921), using constant region specific sequences to design primers to "RACE" the cDNA from total RNA. The variable region (DN1924-heavy, DN1924-light; DN1921-heavy, DN1922-light) sequence was determined from these clones.

Human $IgG_2$ heavy chain and human IgKappa light chain constant region segments were cloned from human spleen total RNA using primers designed from NCBI and the IMGT Home page. Clones were sequenced to confirm the appropriate human IgKappa constant region or human IgG$_2$ constant region.

Oligonucleotide primers used to amplify DN1921 and DN1924 heavy and light chain polynucleotide sequences are presented in Table 3.

Heavy Chain Construction

To combine variable and constant region gene segments, a PCR "sewing" technique was utilized. Briefly, primers were designed to correspond to the 5'- and 3' end of the coding region of the antibody molecule (primers A and B, Table 3). A second set of primers was designed to overlap the junction between the two pieces, present initially, on separate plasmids. Initial PCR reactions were set up with variable region plasmid as template with primer set A+D, or constant region plasmid as template with primer set B+C. Secondary PCR reactions incorporated the products of the first two primary reactions with primer set A+B. The final PCR product was cloned, the sequence confirmed, and then shuttled utilizing restriction enzymes (outside of coding region) into expression vectors, as required.

Light Chain Construction

To combine variable and constant region gene segments, the PCR "sewing" technique was utilized as above for the heavy chain construction. Primers were designed to correspond to the 5'- and 3' end of the coding region of the antibody molecule (primers A and B, Table 3). A third primer was designed to overlap the junction between the two pieces, present initially, on separate plasmids. Initial PCR reactions were set up with constant region plasmid as template with primer set C+B. Secondary PCR reactions incorporated the products of the primary reactions with primer set A+B, and plasmid encoding the Light chain variable region. The final PCR product was cloned, the sequence confirmed, and then shuttled utilizing restriction enzymes (outside of coding region) into expression vectors, as required.

Expression System

DN1924 heavy chain and DN1924 light chain were subcloned into pEE14.4 expression vector (Lonza Biologics, Portsmouth, N.H.), such that both chains of the chimeric immunoglobulin would be encoded on the same vector backbone. Expression of each chain is driven by its own CMV-major immediate early (MIE) promoter. The plasmid containing both heavy and light chain open reading frames was transfected into CHO-K1/Sv cells (Lonza Biologics), and cells were selected in glutamine free medium containing 50 μM methionine-sulfoxamine (MSX), using standard techniques. Chimeric antibody producing cell lines were identified by ELISA.

The same protocol was followed for expression of DN1921 heavy and light chains.

TABLE 3

Oligonucleotides used in the Construction of Chimeric DN1921 and Chimeric DN1924 Monoclonal Antibodies DN1924 heavy chain (Danton)

Primer A SEQ ID NO: 57 5' -- gccggtaccATGGATTTTGGGCTGATTTTTTTTATTG - 3'
Primer B SEQ ID NO: 58 5' -- gcagcggccgcTTATTTACCCGGAGACAGGGAGAGG - 3'
Primer C SEQ ID NO: 59 5' - CCACGGTCACCGTCTCCTCAGCCGCCTCCACCAAG GGCCCATCGGTCTTC - 3'
Primer D SEQ ID NO: 60 5' -- GAAGACCGATGGGCCCTTGGTGGAGGCGGCTGAGGAG ACGGTGACCGTGG - 3'

DN1924 Light Chain (Danton)

Primer A SEQ ID NO: 61 5' -- gcatggtaccaccATGTTCTCACTAGCTCTTCTCCTCAG - 3'
Primer B SEQ ID NO: 62 5' -- gcagcggccgcTTAACACTCTCCCCTGTTGAAG - 3'
Primer C SEQ ID NO: 63 5' -- GGGGGGACCAAGCTGGAAATAAAAACTGTGGCTGCA CCATCTGTCTTC - 3'

DN1921 Heavy Chain (Dantes)

Primer A SEQ ID NO: 64 5' -- gccggtaccATGGTGTTAAGTCTTCTGTACCTG - 3'
Primer B SEQ ID NO: 65 5' -- gcagcggccgcTTATTTACCCGGAGACAGGGAGAGG - 3'
Primer C SEQ ID NO: 66 5' - CAGTCACCGTCTCCTCAGCCGCCTCCACCAAGGG CCCATCGGTCTTC - 3'
Primer D SEQ ID NO: 67 5' - GAAGACCGATGGGCCCTTGGTGGAGGCGGCTGA GGAGACGGTGACTG - 3'

DN1921 Light Chain (Dantes)

Primer A SEQ ID NO: 68 5' - ggcgaattcaccATGGAGACACAGTCTCAGGTCTTC - 3'
Primer B SEQ ID NO: 69 5' - gcagcggccgcTTAACACTCTCCCCTGTTGAAG - 3'
Primer C SEQ ID NO: 70 5' - GAGGGGGGACCAAGCTGGAAATAAGAACTGTG GCTGCACCATCTGTCTTC - 3'

In oligo sequences in Table 3, uppercase letters represent codons for amino acid residues in the open reading frames of the antibody molecules, lowercase letters represent nucleotides added for Kozak consensus sequence (underlined) and restriction endonuclease sites for cloning purposes. The dash in primers 'C' and 'D' represent the junction between murine variable region and human constant region nucleotide sequences.

Example 6

Murine/Human Chimeric DN1921 and DN1924 HLA-DR-Specific Monoclonal Antibodies Specifically Bind to HLA-DR$^+$ Cells This Example demonstrates that the chimeric DN1921 and chimeric DN1924 HLA-DR-specific monoclonal antibodies both specifically bind to HLA-DR expressed on various tissue culture cell lines.

Standard immunofluorescence assay [Current Protocols in Immunology 1, pp. 5.3.1-5.4.13 (Coligan et al., eds., New York, Wiley Interscience, 1998)] was performed using biotinylated goat anti-human IgG biotin conjugate (at 1:200 final dilution; Sigma, St. Louis, Mo.) and streptavidin-PE (at 0.8 µg/ml) as secondary and tertiary reagents, respectively.

Example 7

Murine/Human Chimeric DN1924
HLA-DR-Specific Monoclonal Antibody Induces
Apoptosis in HLA-DR-Expressing Tumor Cell Lines This Example demonstrates that chimeric DN1924 HLA-DR-specific monoclonal antibody is effective in inducing apoptosis in HLA-DR-expressing tumor cells, but not in HLA-DR-negative tumor cells or in normal HLA-DR-expressing cells.

Apoptosis Assay was performed with the Molecular Probes Annexin V Kit using Alexa Flour 488 Conjugate with propidium iodide (PI) counterstain. Briefly, $5 \times 10^5$ viable target cells were co-cultured with 0.1-10 µg mAb in 0.5 to 1 ml total volume media at 37° C. for 10-30 min, washed once with 2 ml ice cold PBS, resuspended in 100 µl of 1× buffer containing 5 µl Annexin V and PI at 1 µg/ml, and incubated at room temperature in the dark for 15 min. Then, 300 µl of 1× buffer was added and the samples were analyzed by flow cytometer within 30 minutes [Current Protocols in Immunology 1, pp. 5.4.1-5.4.13 (Coligan et al., eds., New York, Wiley Interscience, 1998)].

Table 4 demonstrates that murine/human chimeric DN1924 HLA-DR specific monoclonal antibody binds to and induces apoptosis in each member of a panel of HLA-DR positive LcL cell lines. Each LcL cell line expresses a different DRbeta1 allele. These data support the utility to murine/human chimeric anti-HLA-DR antibodies of the present invention in the treatment of disease associated with HLA-DR expression across a wide spectrum of DRbeta1 alleles.

TABLE 4

Murine/Human Chimeric DN-1924 (mut-hIgG2 clone DN16) Specifically Binds to and Induced Apoptosis in a Panel of HLA-DR Positive Cell Lines Expressing a Range of DRβ1 Alleles

| Cell Line | DRβ1 allele | DN1924 binding | DN1924 apoptosis |
|---|---|---|---|
| DM-LcL | 0101 | Yes | Yes |
| KAS116 | 0101 | Yes | Yes |
| PMGO75 | 0102 | Yes | Yes |
| TER-ND RAI | 0103 | No | No |
| EA | 1501 | Yes | Yes |
| E4181324 EA | 15021 | Yes | Yes |
| AMAI AMAL | 1503 | Yes | Yes |
| RML REM | 1602 | Yes | Yes |
| VAVY | 0301 | Yes | Yes |
| RSH RSHD | 0302 | Yes | Yes |
| BM 14 | 0401 | Yes | Yes |
| YAR | 0402 | Yes | Yes |
| SSTO | 0403 | Yes | Yes |
| LKT3 KT3 | 0405 | Yes | Yes |
| KT2 LKT2 | 0406 | Yes | Yes |
| JHAF JHF | 0407 | Yes | Yes |
| BM2 1 | 1101 | Yes | Yes |
| BM1 5 | 1102 | Yes | Yes |
| TISI | 1103 | Yes | Yes |

TABLE 4-continued

Murine/Human Chimeric DN-1924 (mut-hIgG2 clone DN16) Specifically Binds to and Induced Apoptosis in a Panel of HLA-DR Positive Cell Lines Expressing a Range of DRβ1 Alleles

| Cell Line | DRβ1 allele | DN1924 binding | DN1924 apoptosis |
|---|---|---|---|
| BOB | 1104 | Yes | Yes |
| FPAF FPF | 11041 | Yes | Yes |
| BM16 | 1201 | Yes | Yes |
| OMW | 1301 | Yes | Yes |
| EMJ EMJH | 1302 | Yes | Yes |
| HAG | 1303 | Yes | Yes |
| EK | 1401 | Yes | Yes |
| AMALA AZL | 1402 | Yes | Yes |
| BER | 0701 | Yes | Yes |
| BM9 | 0801 | Yes | Yes |
| SPL SPACH | 8021 | Yes | Yes |
| T7 526 | 0901 | Yes | Yes |

Table 5 demonstrates that murine/human chimeric DN1924 HLA-DR specific monoclonal antibody binds to and induces apoptosis in each HLA-DR positive member (with the exception of KG-1) of a panel of tumor cell lines (including three HLA-DR negative tumor cell lines and 12 HLA-DR positive tumor cell lines). Chimeric DN1924 does not induce apoptosis of the HLA-DR negative cell lines even those that express Fc receptors (i.e. U937 and THP-1) or the B-cell tumor cell line (i.e. DB). In contrast, chimeric DN1924 does induce apoptosis of 11 of the 12 HLA-DR positive tumor cell lines. KG-1, an AML tumor cell line, is the only example of an HLA-DR positive tumor cell line (as demonstrated by specific chimeric DN1924 binding activity) that does not undergo apoptosis upon chimeric DN1924 binding. In total, these data demonstrate that chimeric DN1924 is effective in treating a wide range of HLA-DR positive tumor types.

TABLE 5

Murine/Human Chimeric DN-1924 (mut-hIgG2 clone DN16) Specifically Binds to and Induced Apoptosis in a Panel of HLA-DR Positive Tumor Cell Lines
DN1924 Clone #64

| Tumor cell line | Description | HLA-DR | Binding | Apoptosis |
|---|---|---|---|---|
| MC/CAR | Plasmacytoma | Positive | Yes | Yes |
| NC-37 | Burkitt's lymphoma | Positive | Yes | Yes |
| RAJI | Burkitt's lymphoma | Positive | Yes | Yes |
| RPMI 1788 | EBV transformed | Positive | Yes | Yes |
| Human lcl | EBV transformed | Positive | Yes | Yes |
| Rhesus lcl | RhEBV transformed | Positive | Yes | Yes |
| U937 | Histiocytic lymphoma | Negative | No | No |
| CCRF-SB | Lymphoblastic leukemia | Positive | Yes | Yes |
| HS 445 | Hodgkin's disease | Positive | Yes | Yes |
| J M1 | Pre-B cell | Positive | Yes | Yes |
| KG-1 | Acute myelogenous leukemia | Positive | Yes | No |
| SUP-B15 | Acute myleogenous leukemia | Positive | Yes | Yes |

TABLE 5-continued

Murine/Human Chimeric DN-1924 (mut-hIgG2 clone DN16)
Specifically Binds to and Induced Apoptosis in a Panel
of HLA-DR Positive Tumor Cell Lines
DN1924 Clone #64

| Tumor cell line | Description | HLA-DR | Binding | Apoptosis |
|---|---|---|---|---|
| THP-1 | Acute momocytic leukemia | Negative | No | No |
| Toledo | Non-Hodgkin's lymphoma | Positive | Yes | Yes |
| DB | Large cell lymphoma, B lymphoblast | Negative | No | No |

Example 8

Murine/Human Chimeric DN1921 HLA-DR-Specific Monoclonal Antibody is Immunosuppressive The IL-2 secretion assay was performed as described previously [Current Protocols in Immunology 1, pp. 3.14.1-3.14.11 (Coligan et al., eds., New York, Wiley Interscience, 1998)]. Briefly, $10^5$ hybridoma cells of the PAP/HLA-DR1 specific CD4$^+$ T cell hybridoma line Paperino [Vidovic et al., *Human Immunol.* 64:238-244, 2003] were co-cultured in 0.2 ml micro-wells with $2 \times 10^5$ human HLA-DR1$^+$ PBMC as antigen presenting cells, PAP, and mAb (mDN1921=mouse DN1921; mDN1924 =mouse DN1924; DSm89 #34=chimeric DN1921; DN-GS #16=chimeric DN1924). One day later, culture supernatants were harvested and tested at 50% concentration for their ability to support the proliferation of $10^4$ cells of an IL-2 dependent cell line HT-2 for 24 h. Cell growth was measured during the final 6 h culture period by [$^3$H]thymidine cpm incorporation.

Example 9

Murine/Human Chimeric DN1924 HLA-DR-Specific Monoclonal Antibody Induced Apoptosis is Caspase Independent This example demonstrates that murine/human chimeric DN1924's the apoptosis-inducing activity is caspase independent.

Exposure of phosphatidylserine to the outer membrane (detected by Annexin V staining) and caspase activation are both hallmarks of apoptosis. The present example demonstrates, however, that chimeric DN1924-induced apoptosis does not involve activation of caspase 3, caspase 8, or caspase 9 (FIGS. 13A-D and Table 6).

Chimeric DN1924-mediated apoptosis was induced both in the presence and absence of added Z-VAD-fmk, a broad-spectrum caspase inhibitor. Following induction, apoptosis was detected by Annexin V staining and by measuring caspase 3, caspase 8, and caspase 9 activation. Annexin V staining confirmed apoptosis induction and that Z-VAD-fmk was ineffective in inhibiting apoptosis induction. Thus, murine/human DN1924-induced apoptosis was independedt of activation of caspase 3, caspase 8, or caspase 9.

TABLE 6

Murine/Human Chimeric DN1924-induced Apoptosis is Caspase Independent

| Treatment | % Annexin V Propidium Iodide Positive | | % Caspase-3 Activated | | % Caspase-8 Activated | | % Caspase-9 Activated | |
|---|---|---|---|---|---|---|---|---|
| | | Z-VAD-fmk | | Z-VAD-fmk | | Z-VAD-fmk | | Z-VAD-fmk |
| hIgG2-kappa (5 µg/ml) | 15.41% | 13.54% | 2.05% | 0.82% | 0.50% | 1.20% | 0.72% | 0.68% |
| DN1924 #64 (5 µg/ml) | 57.44% | 52.69% | 1.70% | 1.33% | 3.03% | 2.48% | 3.04% | 2.96% |
| mIgM (0.5 µg/ml) | 15.12% | 13.45% | 0.63% | 0.82% | 0.87% | 0.83% | 1.16% | 1.13% |
| CH-11 (0.5 µg/ml) | 52.59% | 23.64% | 23.28% | 6.01% | 25.23% | 6.43% | 26.57% | 6.59% |

Example 10

Murine/Human Chimeric DN1924 HLA-DR-Specific Monoclonal Antibody is Effective in Reducing the Rate of Tumor Growth and in Promoting Increased Survival in a Raji Xenograft Scid Mouse Animal Model System This example demonstrates that in vivo subcutaneous administration of murine/human chimeric DN1924 anti-HLA-DR antibody is effective in reducing the rate of tumor growth (FIG. 14) and in promoting increased survival (FIG. 15) in a Raji xenograft scid mouse animal model system.

On day 0, scid mice (in four groups of five animals) were challenged with $5 \times 10^6$ Raji tumor cells (Burkitts lymphoma; ATCC Catalog No. CCL-86) in 0.1 ml PBS. On days 1, 4, 7, and 10 following tumor challenge; Group 1 received, via intraperitoneal injection, 50 µg of murine DN1924 anti-HLA-DR antibody in 300 µl PBS; Group 2 received, via intraperitoneal injection, 50 µg of murine/human DN1924 anti-HLA-DR antibody (Clone No. 64) in 300 µl PBS; Group 3 received, via intraperitoneal injection, 50 µg of human IgG2, kappa isotype control antibody (Sigma, Catalog No. I5404) in 300 µl PBS; and Group 4 received, via intraperitoneal injection, 300 µl PBS.

FIG. 14 demonstrates that both murine and murine/human chimeric DN1924 lo were effective in reducing the rate of tumor growth from subcutaneous challenge with Raji xenografts in the scid mouse animal model system.

FIG. 15 demonstrates that both murine and murine/human chimeric DN1924 were effective in prolonging survival following subcutaneous challenge with Raji xenografts in the scid mouse animal model system.

Although the invention has been described with respect to particular treatment methods and composition, it will be apparent to those skilled that various changes and modifications can be made without departing from the invention.

---

What is claimed is:

1. An isolated, humanized monoclonal antibody that specifically binds to HLA-DR, comprising (a) a heavy chain variable domain as set forth in SEQ ID NO: 35, and (b) a light chain variable domain as set forth in SEQ ID NO: 24.

2. The antibody of claim 1 in which the antibody has a heavy chain constant domain sequence as set forth in SEQ ID NO: 36 and a light chain constant domain sequence as set forth in SEQ ID NO: 25.

3. The antibody of claim 1 in which the antibody is capable of inducing apoptosis in a tumor cell expressing HLA-DR and wherein the antibody is not suppressive of HLA-DR dependent immune responses.

4. An isolated, humanized monoclonal HLA-DR-specific antibody, comprising (a) a heavy chain variable domain comprising at least 95% sequence identity to the amino acid sequence of SEQ ID NO: 35, and (b) a light chain variable domain comprising at least 95% sequence identity to the amino acid sequence of SEQ ID NO: 24, and wherein said antibody comprises the 3CDRs in SEQ ID NO: 35 and the 3 CDRs in SEQ ID NO: 24.

5. The antibody of claim 4 in which the heavy chain variable domain has the amino acid sequence of SEQ ID NO: 35 and the light chain variable domain has the amino acid sequence of SEQ ID NO: 24.

6. The antibody of claim 4 in which the heavy chain constant domain is selected from the group of antibody isotypes consisting of IgM, IgD, IgG$_2$, IgG$_3$, IgG$_4$, IgE, IgA$_1$ and IgA$_2$.

7. The antibody of claim 4 in which the antibody is capable of inducing apoptosis in a tumor cell expressing HLA-DR and wherein the antibody is not suppressive of HLA-DR dependent immune responses.

* * * * *

SEQUENCE LISTING

```
<160> NUMBER OF SEQ ID NOS: 80

<210> SEQ ID NO 1
<211> LENGTH: 238
<212> TYPE: PRT
<213> ORGANISM: Artificial sequence
<220> FEATURE:
<223> OTHER INFORMATION: Polypeptide expressed from a recombinant DNA
      construct

<400> SEQUENCE: 1

Met Glu Thr Gln Ser Gln Val Phe Leu Ser Leu Leu Leu Trp Val Ser
1               5                   10                  15

Gly Thr Cys Gly Asn Ile Met Leu Thr Gln Ser Pro Ser Ser Leu Ala
            20                  25                  30

Val Ser Ala Gly Glu Lys Val Thr Met Thr Cys Lys Ser Ser Gln Asp
        35                  40                  45

Ile Phe Tyr Ser Ser Asp Gln Arg Asn Tyr Leu Ala Trp Tyr Gln Gln
    50                  55                  60

Arg Pro Gly His Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Asn Val His Pro Glu Asp Leu Ala Val Tyr
            100                 105                 110

Tyr Cys His Gln Tyr Leu Ser Ser Tyr Thr Phe Gly Gly Gly Thr Lys
        115                 120                 125

Leu Glu Ile Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220
```

```
Leu Ser Ser Pro Val Thr Lys Ser Phe Asn Arg Gly Glu Cys
225                 230                 235

<210> SEQ ID NO 2
<211> LENGTH: 132
<212> TYPE: PRT
<213> ORGANISM: Mus musculus

<400> SEQUENCE: 2

Met Glu Thr Gln Ser Gln Val Phe Leu Ser Leu Leu Leu Trp Val Ser
1               5                   10                  15

Gly Thr Cys Gly Asn Ile Met Leu Thr Gln Ser Pro Ser Ser Leu Ala
            20                  25                  30

Val Ser Ala Gly Glu Lys Val Thr Met Thr Cys Lys Ser Ser Gln Asp
        35                  40                  45

Ile Phe Tyr Ser Ser Asp Gln Arg Asn Tyr Leu Ala Trp Tyr Gln Gln
    50                  55                  60

Arg Pro Gly His Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Asn Val His Pro Glu Asp Leu Ala Val Tyr
            100                 105                 110

Tyr Cys His Gln Tyr Leu Ser Ser Tyr Thr Phe Gly Gly Gly Thr Lys
        115                 120                 125

Leu Glu Ile Arg
    130

<210> SEQ ID NO 3
<211> LENGTH: 106
<212> TYPE: PRT
<213> ORGANISM: Homo sapiens

<400> SEQUENCE: 3

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 4
<211> LENGTH: 20
<212> TYPE: PRT
<213> ORGANISM: Mus musculus

<400> SEQUENCE: 4

Met Glu Thr Gln Ser Gln Val Phe Leu Ser Leu Leu Leu Trp Val Ser
1               5                   10                  15

Gly Thr Cys Gly
```

```
                   20

<210> SEQ ID NO 5
<211> LENGTH: 26
<212> TYPE: PRT
<213> ORGANISM: Mus musculus

<400> SEQUENCE: 5

Asn Ile Met Leu Thr Gln Ser Pro Ser Leu Ala Val Ser Ala Gly
 1               5                  10                  15

Glu Lys Val Thr Met Thr Cys Lys Ser Ser
            20                  25

<210> SEQ ID NO 6
<211> LENGTH: 12
<212> TYPE: PRT
<213> ORGANISM: Mus musculus

<400> SEQUENCE: 6

Gln Asp Ile Phe Tyr Ser Ser Asp Gln Arg Asn Tyr
 1               5                  10

<210> SEQ ID NO 7
<211> LENGTH: 17
<212> TYPE: PRT
<213> ORGANISM: Mus musculus

<400> SEQUENCE: 7

Leu Ala Trp Tyr Gln Gln Arg Pro Gly His Ser Pro Lys Leu Leu Ile
 1               5                  10                  15

Tyr

<210> SEQ ID NO 8
<211> LENGTH: 3
<212> TYPE: PRT
<213> ORGANISM: Mus musculus

<400> SEQUENCE: 8

Trp Ala Ser
 1

<210> SEQ ID NO 9
<211> LENGTH: 36
<212> TYPE: PRT
<213> ORGANISM: Mus musculus

<400> SEQUENCE: 9

Thr Arg Glu Ser Gly Val Pro Asp Arg Phe Thr Gly Ser Gly Ser Gly
 1               5                  10                  15

Thr Asp Phe Thr Leu Thr Ile Ser Asn Val His Pro Glu Asp Leu Ala
            20                  25                  30

Val Tyr Tyr Cys
            35

<210> SEQ ID NO 10
<211> LENGTH: 8
<212> TYPE: PRT
<213> ORGANISM: Mus musculus

<400> SEQUENCE: 10

His Gln Tyr Leu Ser Ser Tyr Thr
 1               5
```

```
<210> SEQ ID NO 11
<211> LENGTH: 10
<212> TYPE: PRT
<213> ORGANISM: Mus musculus

<400> SEQUENCE: 11

Phe Gly Gly Gly Thr Lys Leu Glu Ile Arg
1               5                   10

<210> SEQ ID NO 12
<211> LENGTH: 464
<212> TYPE: PRT
<213> ORGANISM: Artificial sequence
<220> FEATURE:
<223> OTHER INFORMATION: Polypeptide expressed from a recombinant DNA
      construct

<400> SEQUENCE: 12

Met Val Leu Ser Leu Leu Tyr Leu Leu Thr Ala Leu Pro Gly Ile Leu
1               5                   10                  15

Ser Glu Val Gln Leu Gln Glu Ser Gly Pro Ser Leu Met Lys Pro Ser
                20                  25                  30

Gln Thr Leu Ser Leu Thr Cys Ser Val Thr Gly Asp Ser Ile Thr Ser
            35                  40                  45

Gly Tyr Trp Asn Trp Ile Arg Gln Phe Pro Gly Lys Lys Leu Glu Tyr
        50                  55                  60

Leu Gly Tyr Val Ser Phe Thr Thr Ser Thr Tyr Tyr Asn Pro Ser Leu
65                  70                  75                  80

Lys Ser Arg Ile Ser Ile Ala Arg Asp Thr Ser Lys Asn Gln Phe Tyr
                85                  90                  95

Leu His Leu Asn Ser Val Thr Ala Ala Asp Thr Ala Thr Tyr Tyr Cys
            100                 105                 110

Ala Arg Leu Gly Gly Leu Leu Pro Phe Gly Ala Met Asp Tyr Trp Ser
        115                 120                 125

Gln Gly Phe Ser Val Thr Val Ser Ser Ala Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Thr Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Ala Ala Ala Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Gln Phe Asn Trp Tyr Val Asp Gly Met Glu Val His Asn Ala
    290                 295                 300

Lys Thr Lys Pro Arg Glu Glu Gln Phe Asn Ser Thr Phe Arg Val Val
305                 310                 315                 320
```

```
Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
            355                 360                 365

Pro Pro Ser Arg Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
            405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
            435                 440                 445

Leu His Asn His Tyr Thr Gln Lys Ser Leu Ser Leu Ser Pro Gly Lys
            450                 455                 460

<210> SEQ ID NO 13
<211> LENGTH: 138
<212> TYPE: PRT
<213> ORGANISM: Mus musculus

<400> SEQUENCE: 13

Met Val Leu Ser Leu Leu Tyr Leu Leu Thr Ala Leu Pro Gly Ile Leu
1               5                   10                  15

Ser Glu Val Gln Leu Gln Glu Ser Gly Pro Ser Leu Met Lys Pro Ser
            20                  25                  30

Gln Thr Leu Ser Leu Thr Cys Ser Val Thr Gly Asp Ser Ile Thr Ser
            35                  40                  45

Gly Tyr Trp Asn Trp Ile Arg Gln Phe Pro Gly Lys Lys Leu Glu Tyr
50                  55                  60

Leu Gly Tyr Val Ser Phe Thr Ser Thr Tyr Tyr Asn Pro Ser Leu
65                  70                  75                  80

Lys Ser Arg Ile Ser Ile Ala Arg Asp Thr Ser Lys Asn Gln Phe Tyr
            85                  90                  95

Leu His Leu Asn Ser Val Thr Ala Ala Asp Thr Ala Thr Tyr Tyr Cys
            100                 105                 110

Ala Arg Leu Gly Gly Leu Leu Pro Phe Gly Ala Met Asp Tyr Trp Ser
            115                 120                 125

Gln Gly Phe Ser Val Thr Val Ser Ser Ala
130                 135

<210> SEQ ID NO 14
<211> LENGTH: 326
<212> TYPE: PRT
<213> ORGANISM: Mus musculus

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45
```

```
Gly Val His Thr Phe Pro Ala Val Leu Gln Ser Ser Gly Leu Tyr Ser
 50                  55                  60

Leu Ser Ser Val Val Thr Val Thr Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Cys Pro Pro Cys Pro Ala Pro
            100                 105                 110

Pro Ala Ala Ala Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 15
<211> LENGTH: 17
<212> TYPE: PRT
<213> ORGANISM: Mus musculus

<400> SEQUENCE: 15

Met Val Leu Ser Leu Leu Tyr Leu Leu Thr Ala Leu Pro Gly Ile Leu
 1               5                  10                  15

Ser

<210> SEQ ID NO 16
<211> LENGTH: 25
<212> TYPE: PRT
<213> ORGANISM: Mus musculus

<400> SEQUENCE: 16

Glu Val Gln Leu Gln Glu Ser Gly Pro Ser Leu Met Lys Pro Ser Gln
 1               5                  10                  15

Thr Leu Ser Leu Thr Cys Ser Val Thr
             20                  25
```

```
<210> SEQ ID NO 17
<211> LENGTH: 8
<212> TYPE: PRT
<213> ORGANISM: Mus musculus

<400> SEQUENCE: 17

Gly Asp Ser Ile Thr Ser Gly Tyr
1               5

<210> SEQ ID NO 18
<211> LENGTH: 17
<212> TYPE: PRT
<213> ORGANISM: Mus musculus

<400> SEQUENCE: 18

Trp Asn Trp Ile Arg Gln Phe Pro Gly Lys Lys Leu Glu Tyr Leu Gly
1               5                   10                  15

Tyr

<210> SEQ ID NO 19
<211> LENGTH: 7
<212> TYPE: PRT
<213> ORGANISM: Mus musculus

<400> SEQUENCE: 19

Val Ser Phe Thr Thr Ser Thr
1               5

<210> SEQ ID NO 20
<211> LENGTH: 38
<212> TYPE: PRT
<213> ORGANISM: Mus musculus

<400> SEQUENCE: 20

Tyr Tyr Asn Pro Ser Leu Lys Ser Arg Ile Ser Ile Ala Arg Asp Thr
1               5                   10                  15

Ser Lys Asn Gln Phe Tyr Leu His Leu Asn Ser Val Thr Ala Ala Asp
            20                  25                  30

Thr Ala Thr Tyr Tyr Cys
        35

<210> SEQ ID NO 21
<211> LENGTH: 14
<212> TYPE: PRT
<213> ORGANISM: Mus musculus

<400> SEQUENCE: 21

Ala Arg Leu Gly Gly Leu Leu Pro Phe Gly Ala Met Asp Tyr
1               5                   10

<210> SEQ ID NO 22
<211> LENGTH: 12
<212> TYPE: PRT
<213> ORGANISM: Mus musculus

<400> SEQUENCE: 22

Trp Ser Gln Gly Phe Ser Val Thr Val Ser Ser Ala
1               5                   10

<210> SEQ ID NO 23
<211> LENGTH: 232
<212> TYPE: PRT
<213> ORGANISM: Artificial sequence
```

```
<220> FEATURE:
<223> OTHER INFORMATION: Polypeptide expressed from a recombinant DNA
      construct

<400> SEQUENCE: 23

Met Phe Ser Leu Ala Leu Leu Ser Leu Leu Leu Cys Val Ser
 1               5                  10                  15

Asp Ser Arg Ala Glu Thr Thr Val Thr Gln Ser Pro Ala Ser Leu Ser
                20                  25                  30

Met Ala Ile Gly Glu Lys Val Thr Ile Arg Cys Ile Thr Ser Thr Asp
            35                  40                  45

Ile Asp Asp Asp Met Asn Trp Tyr Gln Gln Lys Pro Gly Glu Pro Pro
 50                  55                  60

Lys Leu Leu Ile Ser Glu Gly Asn Thr Leu Arg Pro Gly Val Pro Ser
 65                  70                  75                  80

Arg Phe Ser Ser Ser Gly Tyr Gly Thr Asp Phe Val Phe Thr Ile Glu
                85                  90                  95

Asn Met Leu Ser Glu Asp Val Ala Asp Tyr Tyr Leu Gln Ser Asp Asn
                100                 105                 110

Leu Pro Tyr Thr Phe Gly Gly Gly Thr Lys Leu Glu Ile Lys Thr Val
                115                 120                 125

Ala Ala Pro Ser Val Phe Ile Phe Pro Pro Ser Asp Glu Gln Leu Lys
 130                 135                 140

Ser Gly Thr Ala Ser Val Val Cys Leu Leu Asn Asn Phe Tyr Pro Arg
 145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
                180                 185                 190

Leu Ser Ser Thr Leu Thr Leu Ser Lys Ala Asp Tyr Glu Lys His Lys
                195                 200                 205

Val Tyr Ala Cys Glu Val Thr His Gln Gly Leu Ser Ser Pro Val Thr
 210                 215                 220

Lys Ser Phe Asn Arg Gly Glu Cys
 225                 230

<210> SEQ ID NO 24
<211> LENGTH: 126
<212> TYPE: PRT
<213> ORGANISM: Mus musculus

<400> SEQUENCE: 24

Met Phe Ser Leu Ala Leu Leu Ser Leu Leu Leu Cys Val Ser
 1               5                  10                  15

Asp Ser Arg Ala Glu Thr Thr Val Thr Gln Ser Pro Ala Ser Leu Ser
                20                  25                  30

Met Ala Ile Gly Glu Lys Val Thr Ile Arg Cys Ile Thr Ser Thr Asp
            35                  40                  45

Ile Asp Asp Asp Met Asn Trp Tyr Gln Gln Lys Pro Gly Glu Pro Pro
 50                  55                  60

Lys Leu Leu Ile Ser Glu Gly Asn Thr Leu Arg Pro Gly Val Pro Ser
 65                  70                  75                  80

Arg Phe Ser Ser Ser Gly Tyr Gly Thr Asp Phe Val Phe Thr Ile Glu
                85                  90                  95

Asn Met Leu Ser Glu Asp Val Ala Asp Tyr Tyr Leu Gln Ser Asp Asn
                100                 105                 110
```

```
Leu Pro Tyr Thr Phe Gly Gly Gly Thr Lys Leu Glu Ile Lys
        115                 120                 125

<210> SEQ ID NO 25
<211> LENGTH: 106
<212> TYPE: PRT
<213> ORGANISM: Homo sapiens

<400> SEQUENCE: 25

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 26
<211> LENGTH: 20
<212> TYPE: PRT
<213> ORGANISM: Mus musculus

<400> SEQUENCE: 26

Met Phe Ser Leu Ala Leu Leu Leu Ser Leu Leu Leu Cys Val Ser
1               5                   10                  15

Asp Ser Arg Ala
            20

<210> SEQ ID NO 27
<211> LENGTH: 26
<212> TYPE: PRT
<213> ORGANISM: Mus musculus

<400> SEQUENCE: 27

Glu Thr Thr Val Thr Gln Ser Pro Ala Ser Leu Ser Met Ala Ile Gly
1               5                   10                  15

Glu Lys Val Thr Ile Arg Cys Ile Thr Ser
            20                  25

<210> SEQ ID NO 28
<211> LENGTH: 6
<212> TYPE: PRT
<213> ORGANISM: Mus musculus

<400> SEQUENCE: 28

Thr Asp Ile Asp Asp Asp
1               5

<210> SEQ ID NO 29
<211> LENGTH: 17
<212> TYPE: PRT
<213> ORGANISM: Mus musculus

<400> SEQUENCE: 29

Met Asn Trp Tyr Gln Gln Lys Pro Gly Glu Pro Pro Lys Leu Leu Ile
```

```
                1               5                  10                 15
Ser

<210> SEQ ID NO 30
<211> LENGTH: 3
<212> TYPE: PRT
<213> ORGANISM: Mus musculus

<400> SEQUENCE: 30

Glu Gly Asn
1

<210> SEQ ID NO 31
<211> LENGTH: 35
<212> TYPE: PRT
<213> ORGANISM: Mus musculus

<400> SEQUENCE: 31

Thr Leu Arg Pro Gly Val Pro Ser Arg Phe Ser Ser Gly Tyr Gly
1               5                   10                  15

Thr Asp Phe Val Phe Thr Ile Glu Asn Met Leu Ser Glu Asp Val Ala
            20                  25                  30

Asp Tyr Tyr
        35

<210> SEQ ID NO 32
<211> LENGTH: 9
<212> TYPE: PRT
<213> ORGANISM: Mus musculus

<400> SEQUENCE: 32

Leu Gln Ser Asp Asn Leu Pro Tyr Thr
1               5

<210> SEQ ID NO 33
<211> LENGTH: 10
<212> TYPE: PRT
<213> ORGANISM: Mus musculus

<400> SEQUENCE: 33

Phe Gly Gly Gly Thr Lys Leu Glu Ile Lys
1               5                   10

<210> SEQ ID NO 34
<211> LENGTH: 468
<212> TYPE: PRT
<213> ORGANISM: Artificial sequence
<220> FEATURE:
<223> OTHER INFORMATION: Polypeptide expressed from a recombinant DNA
      construct

<400> SEQUENCE: 34

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Tyr Trp Met Ser Trp Val Arg Gln Ala Pro Gly Lys Gly Leu Glu
    50                  55                  60

Trp Ile Gly Glu Ile Asn Pro Asp Ser Ser Thr Ile Asn Tyr Thr Pro
65                  70                  75                  80
```

Ser Leu Lys Asp Lys Phe Ile Ile Ser Arg Asp Asn Ala Lys Asn Thr
            85                  90                  95

Leu Tyr Leu Gln Met Ser Lys Val Arg Ser Glu Asp Thr Ala Leu Tyr
        100                 105                 110

Tyr Cys Ala Arg Gln Pro Tyr Tyr Gly Ser Ser Tyr Trp Tyr Phe
    115                 120                 125

Asp Val Trp Gly Ala Gly Thr Thr Val Thr Val Ser Ser Ala Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
        195                 200                 205

Ser Val Val Thr Val Thr Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Ala
                245                 250                 255

Ala Ala Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
            275                 280                 285

His Glu Asp Pro Glu Val Gln Phe Asn Trp Tyr Val Asp Gly Met Glu
    290                 295                 300

Val His Asn Ala Lys Thr Lys Pro Arg Glu Glu Gln Phe Asn Ser Thr
305                 310                 315                 320

Phe Arg Val Val Ser Val Leu Thr Val His Gln Asp Trp Leu Asn
                325                 330                 335

Gly Lys Glu Tyr Lys Cys Lys Val Ser Asn Lys Gly Leu Pro Ala Pro
                340                 345                 350

Ile Glu Lys Thr Ile Ser Lys Thr Lys Gly Gln Pro Arg Glu Pro Gln
            355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Met Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465

<210> SEQ ID NO 35
<211> LENGTH: 142
<212> TYPE: PRT
<213> ORGANISM: Mus musculus

<400> SEQUENCE: 35

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Tyr Trp Met Ser Trp Val Arg Gln Ala Pro Gly Lys Gly Leu Glu
50                  55                  60

Trp Ile Gly Glu Ile Asn Pro Asp Ser Ser Thr Ile Asn Tyr Thr Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Lys Val Arg Ser Glu Asp Thr Ala Leu Tyr
            100                 105                 110

Tyr Cys Ala Arg Gln Pro Tyr Tyr Gly Ser Ser Tyr Trp Tyr Phe
        115                 120                 125

Asp Val Trp Gly Ala Gly Thr Thr Val Thr Val Ser Ser Ala
130                 135                 140

<210> SEQ ID NO 36
<211> LENGTH: 326
<212> TYPE: PRT
<213> ORGANISM: Mus musculus

<400> SEQUENCE: 36

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 37
<211> LENGTH: 18
<212> TYPE: PRT
<213> ORGANISM: Mus musculus

<400> SEQUENCE: 37

Met Asp Phe Gly Leu Ile Phe Phe Ile Val Ala Leu Leu Lys Gly Val
1               5                   10                  15

Gln Cys

<210> SEQ ID NO 38
<211> LENGTH: 25
<212> TYPE: PRT
<213> ORGANISM: Mus musculus

<400> SEQUENCE: 38

Glu Val Lys Leu Leu Glu Ser Gly Gly Gly Leu Val Gln Pro Gly Gly
1               5                   10                  15

Ser Leu Lys Leu Ser Cys Ala Ala Ser
            20                  25

<210> SEQ ID NO 39
<211> LENGTH: 8
<212> TYPE: PRT
<213> ORGANISM: Mus musculus

<400> SEQUENCE: 39

Gly Phe Asp Phe Ser Arg Tyr Trp
1               5

<210> SEQ ID NO 40
<211> LENGTH: 17
<212> TYPE: PRT
<213> ORGANISM: Mus musculus

<400> SEQUENCE: 40

Met Ser Trp Val Arg Gln Ala Pro Gly Lys Gly Leu Glu Trp Ile Gly
1               5                   10                  15

Glu

<210> SEQ ID NO 41
<211> LENGTH: 8
<212> TYPE: PRT
<213> ORGANISM: Mus musculus

<400> SEQUENCE: 41

```
Ile Asn Pro Asp Ser Ser Thr Ile
1               5

<210> SEQ ID NO 42
<211> LENGTH: 38
<212> TYPE: PRT
<213> ORGANISM: Mus musculus

<400> SEQUENCE: 42

Asn Tyr Thr Pro Ser Leu Lys Asp Lys Phe Ile Ile Ser Arg Asp Asn
1               5                   10                  15

Ala Lys Asn Thr Leu Tyr Leu Gln Met Ser Lys Val Arg Ser Glu Asp
            20                  25                  30

Thr Ala Leu Tyr Tyr Cys
        35

<210> SEQ ID NO 43
<211> LENGTH: 16
<212> TYPE: PRT
<213> ORGANISM: Mus musculus

<400> SEQUENCE: 43

Ala Arg Gln Pro Tyr Tyr Gly Ser Ser Tyr Trp Tyr Phe Asp Val
1               5                   10                  15

<210> SEQ ID NO 44
<211> LENGTH: 12
<212> TYPE: PRT
<213> ORGANISM: Mus musculus

<400> SEQUENCE: 44

Trp Gly Ala Gly Thr Thr Val Thr Val Ser Ser Ala
1               5                   10

<210> SEQ ID NO 45
<211> LENGTH: 1404
<212> TYPE: DNA
<213> ORGANISM: Artificial sequence
<220> FEATURE:
<223> OTHER INFORMATION: Recombinant DNA construct

<400> SEQUENCE: 45
```

| | |
|---|---|
| atgttctcac tagctcttct cctcagtctt cttctcctct gtgtctctga ttctagggca | 60 |
| tacaagagtg atcgagaaga ggagtcagaa gagaggagaa cacagagact aagatcccgt | 120 |
| gaaacaactg tgacccagtc tccagcatcc ctgtccatgg ctataggaga aaaagtcacc | 180 |
| ctttgttgac actgggtcag aggtcgtagg acaggtacc gatatcctct ttttcagtgg | 240 |
| atcagatgca taaccagcac tgatattgat gatgatatga actggtacca gcagaagcca | 300 |
| tagtctacgt attggtcgtg actataacta ctactatact tgaccatggt cgtcttcggt | 360 |
| ggggaacctc ctaagctcct tatttcagaa ggcaatactc ttcgtcctgg agtcccatcc | 420 |
| cccccttggag gattcgagga ataaagtctt ccgttatgag aagcaggacc tcagggtagg | 480 |
| cgattctcca gcagtggcta tggtacagat tttgttttta caattgaaaa catgctctca | 540 |
| gctaagaggt cgtcaccgat accatgtcta aaacaaaaat gttaactttt gtacgagagt | 600 |
| gaagatgttg cagattacta ctgtttgcaa agtgataact tgccgtacac gttcggaggg | 660 |
| cttctacaac gtctaatgat gacaaacgtt tcactattga acggcatgtg caagcctccc | 720 |
| gggaccaagc tggaaataaa aactgtggct gcaccatctg tcttcatctt cccgccatct | 780 |
| ccctggttcg acctttattt ttgacaccga cgtggtagac agaagtagaa gggcggtaga | 840 |

```
gatgagcagt tgaaatctgg aactgcctct gttgtgtgcc tgctgaataa cttctatccc      900
ctactcgtca actttagacc ttgacggaga caacacacgg acgacttatt gaagataggg      960
agagaggcca aagtacagtg aaggtggat  aacgccctcc aatcgggtaa ctcccaggag     1020
tctctccggt tcatgtcac  cttccaccta ttgcgggagg ttagcccatt gagggtcctc     1080
agtgtcacag agcaggacag caaggacagc acctacagcc tcagcagcac cctgacgctg     1140
tcacagtgtc tcgtcctgtc gttcctgtcg tggatgtcgg agtcgtcgtg ggactgcgac     1200
agcaaagcag actacgagaa acacaaagtc tacgcctgcg aagtcaccca tcagggcctg     1260
tcgtttcgtc tgatgctctt tgtgtttcag atgcggacgc ttcagtgggt agtcccggac     1320
agctcgcccg tcacaaagag cttcaacagg ggagagtgtt aatcgagcgg gcagtgtttc     1380
tcgaagttgt cccctctcac aatt                                            1404

<210> SEQ ID NO 46
<211> LENGTH: 1434
<212> TYPE: DNA
<213> ORGANISM: Artificial sequence
<220> FEATURE:
<223> OTHER INFORMATION: Recombinant DNA construct

<400> SEQUENCE: 46
atggagacac agtctcaggt cttcctctcc ctgctgctct gggtatctgg tacctgtggg       60
tacctctgtg tcagagtcca gaaggagagg gacgacgaga cccatagacc atggacaccc      120
aacatcatgc tgacacagtc gccatcatct ctggctgtgt ctgcaggaga aaaggtcact      180
ttgtagtacg actgtgtcag cggtagtaga gaccgacaca gacgtcctct tttccagtga      240
atgacctgta gtccagtcag atattttt   tacagttcag atcagaggaa ctatttggcc      300
tactggacat tcaggtcagt tctataaaaa atgtcaagtc tagtctcctt gataaaccgg      360
tggtaccagc agagaccagg acactctcct aaactactga tctactgggc atccactagg      420
accatggtcg tctctggtcc tgtgagagga tttgatgact agatgacccg taggtgatcc      480
gaatctggtg tccctgatcg cttcacaggc agtggctctg gacagatttt tactcttacc      540
cttagaccac agggactagc gaagtgtccg tcaccgagac cctgtctaaa atgagaatgg      600
atcagcaatg ttcaccctga agacctggca gtttattact gtcatcagta cctctcctcg      660
tagtcgttac aagtgggact tctggaccgt caaataatga cagtagtcat ggagaggagc      720
tacacgttcg gaggggggac caagctggaa ataagaactg tggctgcacc atctgtcttc      780
atgtgcaagc ctccccctg  gttcgacctt tattcttgac accgacgtgg tagacagaag      840
atcttcccgc catctgatga gcagttgaaa tctggaactg cctctgttgt gtgcctgctg      900
tagaagggcg gtagactact cgtcaacttt agaccttgac ggagacaaca cacggacgac      960
aataacttct atcccagaga ggccaaagta cagtggaagg tggataacgc cctccaatcg     1020
ttattgaaga tagggtctct ccggtttcat gtcaccttcc acctattgcg ggaggttagc     1080
ggtaactccc aggagagtgt cacagagcag gacagcaagg acagcaccta cagcctcagc     1140
ccattgaggg tcctctcaca gtgtctcgtc ctgtcgttcc tgtcgtggat gtcggagtcg     1200
agcaccctga cgctgagcaa agcagactac gagaaacaca agtctacgc  ctgcgaagtc     1260 tcgtgggact gcgactcgtt tcgtctgatg ctctttgtgt ttcagatgcg gacgcttcag     1320
acccatcagg gcctgagctc gcccgtcaca aagagcttca cagggga ga gtgttaatgg     1380 gtagtcccgg actcgagcgg gcagtgtttc tcgaagttgt cccctctcac aatt           1434

<210> SEQ ID NO 47
```

<211> LENGTH: 2814
<212> TYPE: DNA
<213> ORGANISM: Artificial sequence
<220> FEATURE:
<223> OTHER INFORMATION: Recombinant DNA construct

<400> SEQUENCE: 47

| | | | | | |
|---|---|---|---|---|---|
| atggattttg | ggctgatttt | ttttattgtt | gctcttttaa | aagggtgtcca | gtgtgaggtg | 60 |
| tacctaaaac | ccgactaaaa | aaaataacaa | cgagaaaatt | ttccccaggt | cacactccac | 120 |
| aagcttctcg | agtctggagg | tggcctggtg | cagcctggag | gatccctgaa | actctcctgt | 180 |
| ttcgaagagc | tcagacctcc | accgaccac | gtcggacctc | ctagggactt | tgagaggaca | 240 |
| gcagcctcag | gattcgattt | tagtagatac | tggatgagtt | gggtccggca | ggctccaggg | 300 |
| cgtcggagtc | ctaagctaaa | atcatctatg | acctactcaa | cccaggccgt | ccgaggtccc | 360 |
| aaagggctag | aatggattgg | agaaattaat | ccagatagca | gtacgataaa | ctatacgcca | 420 |
| tttcccgatc | ttacctaacc | tctttaatta | ggtctatcgt | catgctattt | gatatgcggt | 480 |
| tctctaaagg | ataaattcat | catctccaga | gacaacgcca | aaaatacgct | gtacctgcaa | 540 |
| agagatttcc | tatttaagta | gtagaggtct | ctgttgcggt | ttttatgcga | catggacgtt | 600 |
| atgagcaaag | tgagatctga | ggacacagcc | ctttattact | gtgcaagaca | gccctattac | 660 |
| tactcgtttc | actctagact | cctgtgtcgg | gaaataatga | cacgttctgt | cgggataatg | 720 |
| tacggtagta | gctactggta | cttcgatgtc | tggggcgcag | ggaccacggt | caccgtctcc | 780 |
| atgccatcat | cgatgaccat | gaagctacag | accccgcgtc | cctggtgcca | gtggcagagg | 840 |
| tcagccgcct | ccaccaaggg | cccatcggtc | ttccccctgg | cgccctgctc | caggagcacc | 900 |
| agtcggcgga | ggtggttccc | gggtagccag | aaggggacc | gcgggacgag | gtcctcgtgg | 960 |
| tccgagagca | cagcggccct | gggctgcctg | gtcaaggact | acttccccga | accggtgacg | 1020 |
| aggctctcgt | gtcgccggga | cccgacggac | cagttcctga | tgaaggggct | tggccactgc | 1080 |
| gtgtcgtgga | actcaggcgc | tctgaccagc | ggcgtgcaca | ccttcccggc | tgtcctacag | 1140 |
| cacagcacct | tgagtccgcg | agactggtcg | ccgcacgtgt | ggaagggccg | acaggatgtc | 1200 |
| tcctcaggac | tctactccct | cagcagcgtg | gtgaccgtga | cctccagcaa | cttcggcacc | 1260 |
| aggagtcctg | agatgaggga | gtcgtcgcac | cactggcact | ggaggtcgtt | gaagccgtgg | 1320 |
| cagacctaca | cctgcaacgt | agatcacaag | cccagcaaca | ccaaggtgga | caagacagtt | 1380 |
| gtctggatgt | ggacgttgca | tctagtgttc | gggtcgttgt | ggttccacct | gttctgtcaa | 1440 |
| gagcgcaaat | gttgtgtcga | gtgcccaccg | tgcccagcac | acctgcggc | agcaccgtca | 1500 |
| ctcgcgttta | caacacagct | cacgggtggc | acgggtcgtg | gtggacgccg | tcgtggcagt | 1560 |
| gtcttcctct | tccccccaaa | acccaaggac | accctcatga | tctcccggac | ccctgaggtc | 1620 |
| cagaaggaga | agggggtttt | tgggttcctg | tgggagtact | agagggcctg | gggactccag | 1680 |
| acgtgcgtgg | tggtggacgt | gagccacgaa | gaccccgagg | tccagttcaa | ctggtacgtg | 1740 |
| tgcacgcacc | accacctgca | ctcggtgctt | ctggggctcc | aggtcaagtt | gaccatgcac | 1800 |
| gacggcatgg | aggtgcataa | tgccaagaca | aagccacggg | aggagcagtt | caacagcacg | 1860 |
| ctgccgtacc | tccacgtatt | acggttctgt | ttcggtgccc | tcctcgtcaa | gttgtcgtgc | 1920 |
| ttccgtgtgg | tcagcgtcct | caccgtcgtg | caccaggact | ggctgaacgg | caaggagtac | 1980 |
| aaggcacacc | agtcgcagga | gtggcagcac | gtggtcctga | ccgacttgcc | gttcctcatg | 2040 |
| aagtgcaagg | tctccaacaa | aggcctccca | gcccccatcg | agaaaaccat | ctccaaaacc | 2100 |
| ttcacgttcc | agaggttgtt | tccggagggt | cggggtagc | tcttttggta | gaggttttgg | 2160 |

| | |
|---|---:|
| aaagggcagc cccgagaacc acaggtgtac accctgcccc catcccggga ggagatgacc | 2220 |
| tttcccgtcg gggctcttgg tgtccacatg tgggacgggg gtagggccct cctctactgg | 2280 |
| aagaaccagg tcagcctgac ctgcctggtc aaaggcttct accccagcga catcgccgtg | 2340 |
| ttcttggtcc agtcggactg gacgaccag tttccgaaga tggggtcgct gtagcggcac | 2400 |
| gagtgggaga gcaatgggca gccggagaac aactacaaga ccacacctcc catgctggac | 2460 |
| ctcaccctct cgttacccgt cggcctcttg ttgatgttct ggtgtggagg gtacgacctg | 2520 |
| tccgacggct ccttcttcct ctacagcaag ctcaccgtgg acaagagcag gtggcagcag | 2580 |
| aggctgccga ggaagaagga gatgtcgttc gagtggcacc tgttctcgtc caccgtcgtc | 2640 |
| gggaacgtct tctcatgctc cgtgatgcat gaggctctgc acaaccacta cacacagaag | 2700 |
| cccttgcaga agagtacgag gcactacgta ctccgagacg tgttggtgat gtgtgtcttc | 2760 |
| agcctctccc tgtctccggg taaataatcg gagagggaca gaggcccatt tatt | 2814 |

<210> SEQ ID NO 48
<211> LENGTH: 2796
<212> TYPE: DNA
<213> ORGANISM: Artificial sequence
<220> FEATURE:
<223> OTHER INFORMATION: Recombinant DNA construct

<400> SEQUENCE: 48

| | |
|---|---:|
| atgatggtgt taagtcttct gtacctgttg acagcccttc cgggtatcct gtcagaagtg | 60 |
| tactaccaca attcagaaga catggacaac tgtcgggaag gcccatagga cagtcttcac | 120 |
| cagcttcagg agtcaggacc tagcctcatg aaaccttctc agactctgtc cctcacctgt | 180 |
| gtcgaagtcc tcagtcctgg atcggagtac tttggaagag tctgagacag ggagtggaca | 240 |
| tctgtcactg gcgactccat caccagtggt tactggaact ggatccggca attcccaggg | 300 |
| agacagtgac cgctgaggta gtggtcacca atgaccttga cctaggccgt taagggtccc | 360 |
| aaaaaacttg aatacttggg atacgtaagc ttcactactt ccacttatta caatccatct | 420 |
| ttttttgaac ttatgaaccc tatgcattcg aagtgatgaa ggtgaataat gttaggtaga | 480 |
| ctcaaaagtc gaatctccat cgctcgagac acatccaaga accagttcta cctgcacttg | 540 |
| gagttttcag cttagaggta gcgagctctg tgtaggttct tggtcaagat ggacgtgaac | 600 |
| aattctgtga ctgctgcgga cacagccaca tattactgcg caagattagg gggattacta | 660 |
| ttaagacact gacgacgcct gtgtcggtgt ataatgacgc gttctaatcc ccctaatgat | 720 |
| ccctttggtg ctatggacta ctggagtcaa ggattttcag tcaccgtctc ctcagccgcc | 780 |
| gggaaaccac gatacctgat gacctcagtt cctaaaagtc agtggcagag gagtcggcgg | 840 |
| tccaccaagg gcccatcggt cttccccctg gcgccctgct ccaggagcac ctccgagagc | 900 |
| aggtggttcc cgggtagcca gaaggggac gcgggacga ggtcctcgtg gaggctctcg | 960 |
| acagcggccc tgggctgcct ggtcaaggac tacttccccg aaccggtgac ggtgtcgtgg | 1020 |
| tgtcgccggg acccgacgga ccagttcctg atgaaggggc ttggccactg ccacagcacc | 1080 |
| aactcaggcg ctctgaccag cggcgtgcac accttcccgg ctgtcctaca gtcctcagga | 1140 |
| ttgagtccgc gagactggtc gccgcacgtg tggaagggcc gacaggatgt caggagtcct | 1200 |
| ctctactccc tcagcagcgt ggtgaccgtg acctccagca acttcggcac ccagacctac | 1260 |
| gagatgaggg agtcgtcgca ccactggcac tggaggtcgt tgaagccgtg gtctggatg | 1320 |
| acctgcaacg tagatcacaa gcccagcaac accaaggtgg acaagacagt tgagcgcaaa | 1380 |
| tggacgttgc atctagtgtt cgggtcgttg tggttccacc tgttctgtca actcgcgttt | 1440 |

```
tgttgtgtcg agtgcccacc gtgcccagca ccacctgcgg cagcaccgtc agtcttcctc    1500
acaacacagc tcacgggtgg cacgggtcgt ggtggacgcc gtcgtggcag tcagaaggag    1560
ttccccccaa aacccaagga caccctcatg atctcccgga cccctgaggt cacgtgcgtg    1620
aaggggggtt ttgggttcct gtgggagtac tagagggcct ggggactcca gtgcacgcac    1680
gtggtggacg tgagccacga agaccccgag gtccagttca actggtacgt ggacggcatg    1740
caccacctgc actcggtgct tctggggctc caggtcaagt tgaccatgca cctgccgtac    1800
gaggtgcata atgccaagac aaagccacgg gaggagcagt caacagcac gttccgtgtg    1860 ctccacgtat tacggttctg tttcggtgcc ctcctcgtca agttgtcgtg caaggcacac    1920
gtcagcgtcc tcaccgtcgt gcaccaggac tggctgaacg gcaaggagta caagtgcaag    1980
cagtcgcagg agtggcagca cgtggtcctg accgacttgc cgttcctcat gttcacgttc    2040
gtctccaaca aaggcctccc agcccccatc gagaaaacca tctccaaaac caaagggcag    2100
cagaggttgt ttccggaggg tcgggggtag ctcttttggt agaggttttg gtttcccgtc    2160
ccccgagaac cacaggtgta caccctgccc ccatcccggg aggagatgac caagaaccag    2220
ggggctcttg gtgtccacat gtgggacggg ggtagggccc tcctctactg gttcttggtc    2280
gtcagcctga cctgcctggt caaaggcttc taccccagcg acatcgccgt ggagtgggag    2340
cagtcggact ggacggacca gtttccgaag atggggtcgc tgtagcggca cctcacccct    2400
agcaatgggc agccggagaa caactacaag accacacctc ccatgctgga ctccgacggc    2460
tcgttacccg tcggcctctt gttgatgttc tggtgtggag ggtacgacct gaggctgccg    2520
tccttcttcc tctacagcaa gctcaccgtg gacaagagca ggtggcagca ggggaacgtc    2580
aggaagaagg agatgtcgtt cgagtggcac ctgttctcgt ccaccgtcgt ccccttgcag    2640
ttctcatgct ccgtgatgca tgaggctctg cacaaccact acacacagaa gagcctctcc    2700
aagagtacga ggcactacgt actccgagac gtgttggtga tgtgtgtctt ctcggagagg    2760
ctgtctccgg gtaaataaga cagagggccca tttatt                             2796
```

<210> SEQ ID NO 49
<211> LENGTH: 51
<212> TYPE: PRT
<213> ORGANISM: Homo sapiens

<400> SEQUENCE: 49

Pro Phe Asp Ala Pro Ser Pro Leu Pro Glu Thr Thr Glu Asn Val Val
1               5                   10                  15

Cys Ala Leu Gly Leu Thr Val Gly Leu Val Gly Ile Ile Ile Gly Thr
            20                  25                  30

Ile Phe Ile Ile Lys Gly Leu Arg Lys Ser Asn Ala Ala Glu Arg Arg
        35                  40                  45

Gly Pro Leu
    50

<210> SEQ ID NO 50
<211> LENGTH: 238
<212> TYPE: PRT
<213> ORGANISM: Homo sapiens

<400> SEQUENCE: 50

Pro Gly Asp Thr Arg Pro Arg Phe Leu Gln Gln Asp Lys Tyr Glu Cys
1               5                   10                  15

His Phe Phe Asn Gly Thr Glu Arg Val Arg Phe Leu His Arg Asp Ile
            20                  25                  30

Tyr Asn Gln Glu Glu Asp Leu Arg Phe Asp Ser Asp Val Gly Glu Tyr
        35                  40                  45

Arg Ala Val Thr Glu Leu Gly Arg Pro Asp Ala Glu Tyr Trp Asn Ser
 50                  55                  60

Gln Lys Asp Phe Leu Glu Asp Arg Arg Ala Ala Val Asp Thr Tyr Cys
 65                  70                  75                  80

Arg His Asn Tyr Gly Val Gly Glu Ser Phe Thr Val Gln Arg Val
                 85                  90                  95

Glu Pro Lys Val Thr Val Tyr Pro Ala Arg Thr Gln Thr Leu Gln His
            100                 105                 110

His Asn Leu Leu Val Cys Ser Val Asn Gly Phe Tyr Pro Ala Ser Ile
        115                 120                 125

Glu Val Arg Trp Phe Arg Asn Ser Gln Glu Glu Lys Ala Gly Val Val
        130                 135                 140

Ser Thr Gly Leu Ile Gln Asn Gly Asp Trp Thr Phe Gln Thr Leu Val
145                 150                 155                 160

Met Leu Glu Thr Val Pro Arg Ser Gly Glu Val Tyr Thr Cys Gln Val
                165                 170                 175

Glu His Pro Ser Val Thr Ser Pro Leu Thr Val Glu Trp Arg Ala Gln
            180                 185                 190

Ser Glu Ser Ala Gln Ser Lys Met Leu Ser Gly Val Gly Gly Phe Val
        195                 200                 205

Leu Gly Leu Leu Phe Leu Gly Ala Gly Leu Phe Ile Tyr Phe Lys Asn
        210                 215                 220

Gln Lys Gly His Ser Gly Leu His Pro Thr Gly Leu Val Ser
225                 230                 235

<210> SEQ ID NO 51
<211> LENGTH: 226
<212> TYPE: DNA
<213> ORGANISM: Homo sapiens

<400> SEQUENCE: 51
tcttcccaca ctcattacca tgtactctgc cttatttccc cccagagttt gatgctccaa     60
gccctctccc agagactaca gagaacgtgg tgtgtgccct gggcctgact gtgggtctgg    120
tgggcatcat tattgggacc atcttcatca tcaagggatt gcgcaaaagc aatgcagcag    180
aacgcagggg gcctctgtaa ggcacatgga ggtgagttag gtgtgg                   226

<210> SEQ ID NO 52
<211> LENGTH: 714
<212> TYPE: DNA
<213> ORGANISM: Homo sapiens

<400> SEQUENCE: 52
ggggacaccc gaccacgttt cttgcagcag gataagtatg agtgtcattt cttcaacggg     60
acggagcggg tgcggttcct gcacagagac atctataacc aagaggagga cttgcgcttc    120
gacagcgacg tgggggagta ccgggcggtg acggagctgg gcggcctga cgctgagtac    180 tggaacagcc agaaggactt cctggaagac aggcgcgccg cggtggacac ctactgcaga    240
cacaactacg ggttggtga gagcttcaca gtgcagcggc gagttgagcc taaggtgact    300
gtgtatcctg caaggaccca gaccctgcag caccacaacc tcctggtctg ctctgtgaat    360
ggtttctatc cagccagcat tgaagtcagg tggttccgga acagccagga agagaaggct    420
ggggtggtgt ccacaggcct gattcagaat ggagactgga ccttccagac cctggtgatg    480
ctggaaacag ttcctcgaag tggagaggtt tacacctgcc aagtggagca cccaagcgtg    540

```
acgagccctc tcacagtgga atggagagca cagtctgaat ctgcacagag caagatgctg    600
agtggagtcg ggggctttgt gctgggcctg ctcttccttg gggccgggct attcatctac    660
ttcaagaatc agaaagggca ctctggactt cacccaacag gactcgtgag ctga          714
```

<210> SEQ ID NO 53
<211> LENGTH: 317
<212> TYPE: PRT
<213> ORGANISM: Mus musculus

<400> SEQUENCE: 53

```
Pro Lys Thr Thr Pro Ser Val Tyr Pro Leu Ala Pro Gly Ser Ala
 1               5                  10                  15

Ala Gln Thr Asn Ser Met Val Thr Leu Gly Cys Leu Val Lys Gly Tyr
                20                  25                  30

Phe Pro Glu Pro Val Thr Val Thr Trp Asn Ser Gly Ser Leu Ser Ser
                35                  40                  45

Gly Val Asp Leu Tyr Thr Leu Ser Ser Ser Val Thr Val Pro Ser Ser
            50                  55                  60

Pro Arg Pro Ser Glu Thr Val Thr Cys Asn Val Ala His Pro Ala Ser
 65              70                  75                  80

Ser Thr Lys Val Asp Lys Lys Ile Val Pro Arg Asp Cys Gly Cys Lys
                85                  90                  95

Pro Cys Ile Cys Thr Val Pro Glu Val Ser Ser Val Phe Ile Phe Pro
                100                 105                 110

Pro Lys Pro Lys Asp Val Leu Thr Ile Thr Leu Thr Pro Lys Val Thr
            115                 120                 125

Cys Val Val Val Asp Ile Ser Lys Asp Asp Pro Glu Val Gln Phe Ser
130                 135                 140

Trp Phe Val Asp Asp Val Glu Val His Thr Ala Gln Thr Gln Pro Arg
145                 150                 155                 160

Glu Glu Gln Phe Asn Ser Thr Phe Arg Ser Val Ser Glu Leu Pro Ile
                165                 170                 175

Met His Gln Asp Trp Leu Asn Gly Lys Glu Phe Lys Cys Arg Val Asn
                180                 185                 190

Ser Ala Ala Phe Pro Ala Pro Ile Glu Lys Thr Ile Ser Lys Thr Lys
            195                 200                 205

Gly Arg Pro Lys Ala Pro Gln Val Tyr Thr Ile Pro Pro Lys Glu
210                 215                 220

Gln Met Ala Lys Asp Lys Val Ser Leu Thr Cys Met Ile Thr Asp Phe
225                 230                 235                 240

Phe Pro Glu Asp Ile Thr Val Glu Trp Gln Trp Asn Gly Gln Pro Ala
                245                 250                 255

Glu Asn Tyr Lys Asn Thr Gln Pro Ile Met Asn Thr Asn Gly Ser Tyr
                260                 265                 270

Phe Val Tyr Ser Lys Leu Asn Val Gln Lys Ser Asn Trp Glu Ala Gly
            275                 280                 285

Asn Thr Phe Thr Cys Ser Val Leu His Glu Gly Leu His Asn His His
            290                 295                 300

Thr Glu Lys Ser Leu Ser His Ser Pro Gly Lys Gly Lys
305                 310                 315
```

<210> SEQ ID NO 54
<211> LENGTH: 1823
<212> TYPE: DNA
<213> ORGANISM: Mus musculus

<400> SEQUENCE: 54

```
tcggggacat gggaagggtg caaaagtagc ggccttctag aaggtttgga cctgtcctgt      60
cctgtccgac agtgtaatca catatacttt ttcttgtagc caaaacgaca ccccatctg      120
tctatccact ggcccctgga tctgctgccc aaactaactc catggtgacc ctgggatgcc    180
tggtcaaggg ctatttccct gagccagtga cagtgacctg gaactctgga tccctgtcca    240
gcggtgtgca caccttccca gctgtcctgg agtctgacct ctacactctg agcagctcag    300
tgactgtccc ctccagccct cggcccagcg agaccgtcac ctgcaacgtt gcccacccgg    360
ccagcagcac caaggtggac aagaaaattg gtgagaggac atatagggag gaggggttca    420
ctagaagtga ggctcaagcc attagcctgc ctaaaccaac caggctggac agccaaccaa    480
ccaggaaatg gatctcagcc cagaagatca aaagttgttc ttctcccttc tggagatttc    540
tatgtccttt acaactcaat tggttaatat cctgggttgg agtcccacac atcttgacaa    600
acagagacaa atttgagtat caccagccaa agtcatacc caaaaacagc ctggcatgac     660
cacacaccag actcaaactt accctacctt tatcctggtg gcttctcatc tccagacccc    720
agtaacacat agctttctct ccacagtgcc cagggattgt ggttgtaagc cttgcatatg    780
tacaggtaag tcagtggcct tcacctgacc cagatgcaac aagtggcaat gttggagggt    840
ggccaggtat tgacctattt ccaccttttct tcttcatcct tagtcccaga agtatcatct    900
gtcttcatct tcccccaaa gcccaaggat gtgctcacca ttactctgac tcctaaggtc     960
acgtgtgttg tggtagacat cagcaaggat gatcccgagg tccagttcag ctggttgta    1020
gatgatgtgg aggtgcacac agctcagacg caaccccggg aggagcagtt caacagcact    1080
ttccgctcag tcagtgaact tcccatcatg caccaggact ggctcaatgg caaggagttc    1140
aaatgcaggg tcaacagtgc agctttccct gcccccatcg agaaaaccat ctccaaaacc    1200
aaaggtgaga gctgcagtgt gtgacataga agctgcaata gtcagtccat agacagagct    1260
tggcataaca gaccccctgcc ctgttcgtga cctctgtgct gaccaatctc tttacccacc    1320
cacaggcaga ccgaaggctc cacaggtgta caccattcca cctcccaagg agcagatggc    1380
caaggataaa gtcagtctga cctgcatgat aacagacttc ttccctgaag acattactgt    1440
ggagtggcag tggaatgggc agccagcgga gaactacaag aacactcagc ccatcatgaa    1500
cacgaatggc tcttacttcg tctacagcaa gctcaatgtg cagaagagca actgggaggc    1560
aggaaatact ttcacctgct ctgtgttaca tgagggcctg cacaaccacc atactgagaa    1620
gagcctctcc cactctcctg gtaaatgatc ccagtgtcct tggagccctc tggtcctaca    1680
ggactctgac acctacctcc accctccct gtataaataa agcacccagc actgccttgg   1740
gaccctgcaa taacgtcctg gtgatttctg agatgtagag tctagctagg tcatggaatg    1800
agggggtctcc atggtttgag ccc                                            1823
```

<210> SEQ ID NO 55
<211> LENGTH: 220
<212> TYPE: PRT
<213> ORGANISM: Mus musculus

<400> SEQUENCE: 55

```
Pro Asp Val Val Met Thr Gln Ser Pro Leu Ser Leu Pro Val Ser Leu
  1               5                  10                  15

Gly Asp Gln Ala Ser Ile Ser Cys Arg Ser Ser Gln Ser Ile Val His
             20                  25                  30

Ser Asn Gly Asn Thr Tyr Leu Glu Trp Tyr Leu Gln Lys Pro Gly Gln
```

```
                35                  40                  45
Ser Pro Lys Leu Leu Ile Tyr Lys Val Ser Asn Arg Phe Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Leu Gly Val Tyr Tyr Cys Phe Gln
                 85                  90                  95

Gly Ser His Val Pro Pro Thr Phe Gly Gly Gly Thr Asn Leu Glu Ile
                100                 105                 110

Lys Arg Ala Asp Ala Ala Pro Thr Val Ser Ile Phe Pro Pro Ser Ser
                115                 120                 125

Glu Gln Leu Thr Ser Gly Gly Ala Ser Val Val Cys Phe Leu Asn Asn
130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
                180                 185                 190

Glu Arg His Asn Ser Tyr Thr Cys Glu Ala Thr His Lys Thr Ser Thr
                195                 200                 205

Ser Pro Ile Val Lys Ser Phe Asn Arg Asn Glu Cys
210                 215                 220

<210> SEQ ID NO 56
<211> LENGTH: 660
<212> TYPE: DNA
<213> ORGANISM: Mus musculus

<400> SEQUENCE: 56
gatgttgtga tgacccaatc tccactctcc ctgcctgtca gtcttggaga tcaagcctcc      60
atctcttgca gatctagtca gagcatagta catagtaatg gaaacaccta tttagaatgg     120
tacctgcaga aaccaggcca gtctccaaag ctcctgatct acaaagtttc caaccgattt     180
tctggggtcc cagataggtt cagtggcagt ggatcaggga cagatttcac actcaagatc     240
agcagagtgg aggctgagga tctgggagtt tattactgct ttcaaggttc acatgttcct     300
cccacgttcg gagggggggac caacctggaa ataaaacggg ctgatgctgc accaactgta     360
tccatcttcc caccatccag tgagcagtta acatctggag gtgcctcagt cgtgtgcttc     420
ttgaacaact tctaccccaa agacatcaat gtcaagtgga agattgatgg cagtgaacga     480
caaaatggcg tcctgaacag ttggactgat caggacagca agacagcac ctacagcatg     540 agcagcaccc tcacgttgac caaggacgag tatgaacgac ataacagcta cctgtgagag     600 ccactcaca agacatcaac ttcacccatt gtcaagagct caacaggaa tgagtgttaa     660

<210> SEQ ID NO 57
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 57
gccggtacca tggattttgg gctgattttt tttattg                              37

<210> SEQ ID NO 58
<211> LENGTH: 36
```

```
<212> TYPE: DNA
<213> ORGANISM: Artificial Sequence
<220> FEATURE:
<223> OTHER INFORMATION: Synthetic polynucleotide

<400> SEQUENCE: 58
gcagcggccg cttatttacc cggagacagg gagagg                              36

<210> SEQ ID NO 59
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 59
ccacggtcac cgtctcctca gccgcctcca ccaagggccc atcggtcttc               50

<210> SEQ ID NO 60
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 60
gaagaccgat gggcccttgg tggaggcggc tgaggagacg gtgaccgtgg               50

<210> SEQ ID NO 61
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 61
gcatggtacc accatgttct cactagctct tctcctcag                           39

<210> SEQ ID NO 62
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 62
gcagcggccg cttaacactc tcccctgttg aag                                 33

<210> SEQ ID NO 63
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 63 gggggggacca agctggaaat aaaaactgtg gctgcaccat ctgtcttc                48

<210> SEQ ID NO 64
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 64
gccggtacca tggtgttaag tcttctgtac ctg                                 33
```

<210> SEQ ID NO 65
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 65
gcagcggccg cttatttacc cggagacagg gagagg                           36

<210> SEQ ID NO 66
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 66
cagtcaccgt ctcctcagcc gcctccacca agggcccatc ggtcttc               47

<210> SEQ ID NO 67
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 67
gaagaccgat gggcccttgg tggaggcggc tgaggagacg gtgactg               47

<210> SEQ ID NO 68
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 68
ggcgaattca ccatggagac acagtctcag gtcttc                           36

<210> SEQ ID NO 69
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 69
gcagcggccg cttaacactc tcccctgttg aag                              33

<210> SEQ ID NO 70
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 70 gagggggac caagctggaa ataagaactg tggctgcacc atctgtcttc              50

<210> SEQ ID NO 71
<211> LENGTH: 6
<212> TYPE: PRT
<213> ORGANISM: Artificial Sequence
<220> FEATURE:
<223> OTHER INFORMATION: Synthetic peptide

<400> SEQUENCE: 71

His His His His His His
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic peptide

<400> SEQUENCE: 72

Asp Tyr Lys Asp Asp Asp Asp Lys
1               5

<210> SEQ ID NO 73
<211> LENGTH: 326
<212> TYPE: PRT
<213> ORGANISM: Homo sapiens

<400> SEQUENCE: 73

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

```
Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 74
<211> LENGTH: 329
<212> TYPE: PRT
<213> ORGANISM: Homo sapiens

<400> SEQUENCE: 74

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Val Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

<210> SEQ ID NO 75
<211> LENGTH: 327
<212> TYPE: PRT
<213> ORGANISM: Homo sapiens

<400> SEQUENCE: 75

| Ala | Ser | Phe | Lys | Gly | Pro | Ser | Val | Phe | Pro | Leu | Val | Pro | Cys | Ser | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Thr | Ser | Glu | Ser | Thr | Ala | Ala | Leu | Gly | Cys | Leu | Val | Lys | Asp | Tyr |
|     |     |     | 20  |     |     |     |     | 25  |     |     |     |     | 30  |     |     |

| Phe | Pro | Glu | Pro | Val | Thr | Val | Ser | Trp | Asn | Ser | Cys | Ala | Leu | Thr | Ser |
|     |     | 35  |     |     |     |     | 40  |     |     |     |     | 45  |     |     |     |

| Gly | Val | His | Thr | Phe | Pro | Ala | Val | Leu | Gln | Ser | Ser | Gly | Leu | Tyr | Ser |
|     | 50  |     |     |     |     | 55  |     |     |     |     | 60  |     |     |     |     |

| Leu | Ser | Ser | Val | Val | Thr | Val | Pro | Ser | Ser | Ser | Leu | Gly | Thr | Lys | Thr |
| 65  |     |     |     |     | 70  |     |     |     |     | 75  |     |     |     |     | 80  |

| Tyr | Thr | Cys | Asn | Val | Asp | His | Lys | Pro | Ser | Asn | Thr | Lys | Val | Asp | Lys |
|     |     |     |     | 85  |     |     |     |     | 90  |     |     |     |     | 95  |     |

| Arg | Val | Glu | Ser | Lys | Tyr | Gly | Pro | Pro | Cys | Pro | Ser | Cys | Pro | Ala | Pro |
|     |     |     | 100 |     |     |     |     | 105 |     |     |     |     | 110 |     |     |

| Glu | Phe | Leu | Gly | Gly | Pro | Ser | Val | Phe | Leu | Phe | Pro | Pro | Lys | Pro | Lys |
|     |     | 115 |     |     |     |     | 120 |     |     |     |     | 125 |     |     |     |

| Asp | Thr | Leu | Met | Ile | Ser | Arg | Thr | Pro | Glu | Val | Thr | Cys | Val | Val | Val |
|     | 130 |     |     |     |     | 135 |     |     |     |     | 140 |     |     |     |     |

| Asp | Val | Ser | Gln | Glu | Asp | Pro | Glu | Val | Gln | Phe | Asn | Trp | Tyr | Val | Asp |
| 145 |     |     |     |     | 150 |     |     |     |     | 155 |     |     |     |     | 160 |

| Gly | Val | Glu | Val | His | Asn | Ala | Lys | Thr | Lys | Pro | Arg | Glu | Glu | Gln | Phe |
|     |     |     |     | 165 |     |     |     |     | 170 |     |     |     |     | 175 |     |

| Asn | Ser | Thr | Tyr | Arg | Val | Val | Arg | Val | Leu | Thr | Val | Leu | His | Gln | Asp |
|     |     |     | 180 |     |     |     |     | 185 |     |     |     |     | 190 |     |     |

| Trp | Leu | Asn | Gly | Lys | Glu | Tyr | Lys | Cys | Lys | Val | Ser | Asn | Lys | Gly | Leu |
|     |     | 195 |     |     |     |     | 200 |     |     |     |     | 205 |     |     |     |

| Pro | Ser | Ser | Ile | Glu | Lys | Thr | Ile | Ser | Lys | Ala | Lys | Gly | Gln | Pro | Arg |
|     | 210 |     |     |     |     | 215 |     |     |     |     | 220 |     |     |     |     |

| Glu | Pro | Gln | Val | Tyr | Thr | Leu | Pro | Pro | Ser | Gln | Glu | Glu | Met | Thr | Lys |
| 225 |     |     |     |     | 230 |     |     |     |     | 235 |     |     |     |     | 240 |

| Asn | Gln | Val | Ser | Leu | Thr | Cys | Leu | Val | Lys | Gly | Phe | Tyr | Pro | Ser | Asp |
|     |     |     |     | 245 |     |     |     |     | 250 |     |     |     |     | 255 |     |

| Ile | Ala | Val | Glu | Trp | Glu | Ser | Asn | Gly | Gln | Pro | Glu | Asp | Asn | Tyr | Lys |
|     |     |     | 260 |     |     |     |     | 265 |     |     |     |     | 270 |     |     |

| Thr | Thr | Pro | Pro | Val | Leu | Asp | Ser | Asp | Gly | Ser | Phe | Phe | Leu | Tyr | Ser |
|     |     | 275 |     |     |     |     | 280 |     |     |     |     | 285 |     |     |     |

| Arg | Leu | Thr | Val | Asp | Lys | Ser | Arg | Trp | Gln | Glu | Gly | Asn | Val | Phe | Ser |
|     | 290 |     |     |     |     | 295 |     |     |     |     | 300 |     |     |     |     |

| Cys | Ser | Val | Met | His | Glu | Ala | Leu | His | Asn | His | Tyr | Thr | Gln | Lys | Ser |
| 305 |     |     |     |     | 310 |     |     |     |     | 315 |     |     |     |     | 320 |

| Leu | Ser | Leu | Ser | Pro | Gly | Lys |
|     |     |     |     | 325 |     |     |

<210> SEQ ID NO 76
<211> LENGTH: 325
<212> TYPE: PRT
<213> ORGANISM: Mus musculus

<400> SEQUENCE: 76

-continued

```
Lys Thr Thr Pro Pro Ser Val Tyr Pro Leu Ala Pro Gly Ser Ala Ala
  1               5                  10                  15

Gln Thr Asn Ser Met Val Thr Leu Gly Cys Leu Val Lys Gly Tyr Phe
             20                  25                  30

Pro Glu Pro Val Thr Val Thr Trp Asn Ser Gly Ser Leu Ser Ser Gly
         35                  40                  45

Val His Thr Phe Pro Ala Val Leu Glu Ser Asp Leu Tyr Thr Leu Ser
     50                  55                  60

Ser Ser Val Thr Val Pro Ser Ser Pro Arg Pro Ser Glu Thr Val Thr
 65                  70                  75                  80

Cys Asn Val Ala His Pro Ala Ser Ser Thr Lys Val Asp Lys Lys Ile
                 85                  90                  95

Val Pro Arg Asp Cys Gly Cys Lys Pro Cys Ile Cys Thr Val Pro Glu
             100                 105                 110

Val Ser Ser Val Phe Ile Phe Pro Pro Lys Pro Lys Asp Val Leu Thr
         115                 120                 125

Ile Thr Leu Thr Pro Lys Val Thr Cys Val Val Val Asp Ile Ser Lys
     130                 135                 140

Asp Asp Pro Glu Val Gln Phe Ser Trp Phe Val Asp Asp Val Glu Val
145                 150                 155                 160

His Thr Ala Gln Thr Gln Pro Arg Glu Glu Gln Phe Asn Ser Thr Phe
                 165                 170                 175

Arg Ser Val Ser Glu Leu Pro Ile Met His Gln Asp Trp Leu Asn Gly
             180                 185                 190

Lys Glu Phe Lys Cys Arg Val Asn Ser Ala Ala Phe Pro Ala Pro Ile
         195                 200                 205

Glu Lys Thr Ile Ser Lys Thr Lys Gly Arg Pro Lys Ala Pro Gln Val
     210                 215                 220

Tyr Thr Ile Pro Pro Lys Glu Gln Met Ala Lys Asp Lys Val Ser
225                 230                 235                 240

Leu Thr Cys Met Ile Thr Asp Phe Phe Pro Glu Asp Ile Thr Val Glu
                 245                 250                 255

Trp Gln Trp Asn Gly Gln Pro Ala Glu Asn Tyr Lys Asn Thr Gln Pro
             260                 265                 270

Ile Met Asn Thr Asn Gly Ser Tyr Phe Val Tyr Ser Lys Leu Asn Val
         275                 280                 285

Gln Lys Ser Asn Trp Glu Ala Gly Asn Thr Phe Thr Cys Ser Val Leu
     290                 295                 300

His Glu Gly Leu His Asn His His Thr Glu Lys Ser Leu Ser His Ser
305                 310                 315                 320

Pro Gly Lys Gly Lys
                325
```

<210> SEQ ID NO 77
<211> LENGTH: 330
<212> TYPE: PRT
<213> ORGANISM: Mus musculus

<400> SEQUENCE: 77

```
Lys Thr Thr Ala Pro Ser Val Tyr Pro Leu Ala Pro Val Cys Gly Asp
  1               5                  10                  15

Thr Thr Gly Ser Ser Val Thr Leu Gly Cys Leu Val Lys Gly Tyr Phe
             20                  25                  30

Pro Glu Pro Val Thr Leu Thr Trp Asn Ser Gly Ser Leu Ser Ser Gly
         35                  40                  45
```

```
Val His Thr Phe Pro Ala Val Leu Gln Ser Asp Leu Tyr Thr Leu Ser
    50                  55                  60

Ser Ser Val Thr Val Thr Ser Ser Thr Trp Pro Ser Gln Ser Ile Thr
65                  70                  75                  80

Cys Asn Val Ala His Pro Ala Ser Ser Thr Lys Val Asp Lys Lys Ile
                85                  90                  95

Glu Pro Arg Gly Pro Thr Ile Lys Pro Cys Pro Pro Cys Lys Cys Pro
            100                 105                 110

Ala Pro Asn Leu Leu Gly Gly Pro Ser Val Phe Ile Phe Pro Pro Lys
            115                 120                 125

Ile Lys Asp Val Leu Met Ile Ser Leu Ser Pro Ile Val Thr Cys Val
        130                 135                 140

Val Val Asp Val Ser Glu Asp Asp Pro Asp Val Gln Ile Ser Trp Phe
145                 150                 155                 160

Val Asn Asn Val Glu Val His Thr Ala Gln Thr Gln Thr His Arg Glu
                165                 170                 175

Asp Tyr Asn Ser Thr Leu Arg Val Val Ser Ala Leu Pro Ile Gln His
            180                 185                 190

Gln Asp Trp Met Ser Gly Lys Glu Phe Lys Cys Lys Val Asn Asn Lys
            195                 200                 205

Asp Leu Pro Ala Pro Ile Glu Arg Thr Ile Ser Lys Pro Lys Gly Ser
        210                 215                 220

Val Arg Ala Pro Gln Val Tyr Val Leu Pro Pro Glu Glu Glu Met
225                 230                 235                 240

Thr Lys Lys Gln Val Thr Leu Thr Cys Met Val Thr Asp Phe Met Pro
                245                 250                 255

Glu Asp Ile Tyr Val Glu Trp Thr Asn Asn Gly Lys Thr Glu Leu Asn
            260                 265                 270

Tyr Lys Asn Thr Glu Pro Val Leu Asp Ser Asp Gly Ser Tyr Phe Met
        275                 280                 285

Tyr Ser Lys Leu Arg Val Glu Lys Lys Asn Trp Val Glu Arg Asn Ser
    290                 295                 300

Tyr Ser Cys Ser Val Val His Glu Gly Leu His Asn His His Thr Thr
305                 310                 315                 320

Lys Ser Phe Ser Arg Thr Pro Gly Lys Val
                325                 330

<210> SEQ ID NO 78
<211> LENGTH: 336
<212> TYPE: PRT
<213> ORGANISM: Mus musculus

<400> SEQUENCE: 78

Lys Thr Thr Pro Pro Ser Val Tyr Pro Leu Ala Pro Gly Cys Gly Asp
1               5                   10                  15

Thr Thr Gly Ser Ser Val Thr Leu Gly Cys Leu Val Lys Gly Tyr Phe
            20                  25                  30

Pro Glu Ser Val Thr Val Thr Trp Asn Ser Gly Ser Leu Ser Ser Ser
        35                  40                  45

Val His Thr Phe Pro Ala Leu Leu Gln Ser Gly Leu Tyr Thr Met Ser
    50                  55                  60

Ser Ser Val Thr Val Pro Ser Ser Thr Trp Pro Ser Gln Thr Val Thr
65                  70                  75                  80

Cys Ser Val Ala His Pro Ala Ser Ser Thr Thr Val Asp Lys Lys Leu
                85                  90                  95
```

```
Glu Pro Ser Gly Pro Ile Ser Thr Ile Asn Pro Cys Pro Pro Cys Lys
                100                 105                 110

Glu Cys His Lys Cys Pro Ala Pro Asn Leu Glu Gly Gly Pro Ser Val
            115                 120                 125

Phe Ile Phe Pro Pro Asn Ile Lys Asp Val Leu Met Ile Ser Leu Thr
130                 135                 140

Pro Lys Val Thr Cys Val Val Asp Val Ser Glu Asp Asp Pro Asp
145                 150                 155                 160

Val Gln Ile Ser Trp Phe Val Asn Asn Val Glu Val His Thr Ala Gln
                165                 170                 175

Thr Gln Thr His Arg Glu Asp Tyr Asn Ser Thr Ile Arg Val Val Ser
            180                 185                 190

Thr Leu Pro Ile Gln His Gln Asp Trp Met Ser Gly Lys Glu Phe Lys
        195                 200                 205

Cys Lys Val Asn Asn Lys Asp Leu Pro Ser Pro Ile Glu Arg Thr Ile
    210                 215                 220

Ser Lys Ile Lys Gly Leu Val Arg Ala Pro Gln Val Tyr Ile Leu Pro
225                 230                 235                 240

Pro Pro Ala Glu Gln Leu Ser Arg Lys Asp Val Ser Leu Thr Cys Leu
                245                 250                 255

Val Val Gly Phe Asn Pro Gly Asp Ile Ser Val Glu Trp Thr Ser Asn
            260                 265                 270

Gly His Thr Glu Glu Asn Tyr Lys Asp Thr Ala Pro Val Leu Asp Ser
        275                 280                 285

Asp Gly Ser Tyr Phe Ile Tyr Ser Lys Leu Asn Met Lys Thr Ser Lys
    290                 295                 300

Trp Glu Lys Thr Asp Ser Phe Ser Cys Asn Val Arg His Glu Gly Leu
305                 310                 315                 320

Lys Asn Tyr Tyr Leu Lys Lys Thr Ile Ser Arg Ser Pro Gly Lys Val
                325                 330                 335

<210> SEQ ID NO 79
<211> LENGTH: 107
<212> TYPE: PRT
<213> ORGANISM: Artificial sequence
<220> FEATURE:
<223> OTHER INFORMATION: Polypeptide expressed from a recombinant DNA
      construct

<400> SEQUENCE: 79

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 80
<211> LENGTH: 107
```

```
<212> TYPE: PRT
<213> ORGANISM: Mus musculus

<400> SEQUENCE: 80

Arg Ala Asp Ala Ala Pro Thr Val Ser Ile Phe Pro Pro Ser Ser Glu
 1               5                  10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
            35                  40                  45

Gln Asn Gly Val Leu Asn Ser Trp Thr Asp Gln Asp Ser Lys Asp Ser
        50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```